(12) United States Patent
Shukla et al.

(10) Patent No.: US 9,227,919 B2
(45) Date of Patent: Jan. 5, 2016

(54) ARYLALKYLAMINE COMPOUNDS AS CALCIUM SENSING RECEPTOR MODULATORS

(71) Applicant: Lupin Limited, Mumbai (IN)

(72) Inventors: Manojkumar Ramprasad Shukla, Pune (IN); Vinod Dinkar Chaudhari, Pune (IN); Ankush Gangaram Sarde, Pune (IN); Ramesh Dattatraya Phadtare, Pune (IN); Mahadeo Bhaskar Tryambake, Pune (IN); Dronamraju Prameela, Pune (IN); Sanjeev Anant Kulkarni, Pune (IN); Rajender Kumar Kamboj, Pune (IN); Venkata P. Palle, Pune (IN)

(73) Assignee: Lupin Limited, Pune (IN)

( * ) Notice: Subject to any disclaimer, the term of this patent is extended or adjusted under 35 U.S.C. 154(b) by 0 days.

(21) Appl. No.: 14/422,373

(22) PCT Filed: Aug. 23, 2013

(86) PCT No.: PCT/IB2013/056840
§ 371 (c)(1),
(2) Date: Feb. 19, 2015

(87) PCT Pub. No.: WO2014/033604
PCT Pub. Date: Mar. 6, 2014

(65) Prior Publication Data
US 2015/0239827 A1    Aug. 27, 2015

(30) Foreign Application Priority Data

Aug. 27, 2012  (IN) .............................. 988/KOL/2012
Sep. 10, 2012  (IN) .............................. 1031/KOL/2012

(51) Int. Cl.
| | | |
|---|---|---|
| *C07D 215/12* | (2006.01) | |
| *C07C 227/02* | (2006.01) | |
| *C07C 229/38* | (2006.01) | |
| *A61K 31/135* | (2006.01) | |
| *A61K 31/136* | (2006.01) | |
| *A61K 31/47* | (2006.01) | |
| *C07C 303/26* | (2006.01) | |

(52) U.S. Cl.
CPC ............. *C07C 229/38* (2013.01); *C07C 227/02* (2013.01); *C07C 303/26* (2013.01); *C07D 215/12* (2013.01)

(58) Field of Classification Search
None
See application file for complete search history.

(56) References Cited

U.S. PATENT DOCUMENTS

2003/0199497 A1   10/2003   Ruat

FOREIGN PATENT DOCUMENTS

WO   2014/033604 A1   3/2014

OTHER PUBLICATIONS

Shao L. et al.: "Synthesis and Pharmacological Evaluation of 4-(3,4-dichlorophenyl)-N-methyls-1,2,3,4-te  trahydronaphthalenyl amines as triple reuptake inhibitors", Bioorganic Y Medicinal Chemistry, Pergamon, GB, vol. 19, No. 1, Jan. 1, 2011, pp. 663-676.
International Search Report & Written Opinion dated Feb. 11, 2014; Appln. No. PCT/IB2013/056840.

*Primary Examiner* — Michael Barker
(74) *Attorney, Agent, or Firm* — The Dobrusin Law Firm, PC

(57) ABSTRACT

The present invention provides arylalkylamine compounds as calcium sensing receptor modulators (CaSR). In particular, the compounds described herein are useful for treating, managing, and/or lessening the severity of diseases, disorders, syndromes and/or conditions associated with the modulation of calcium sensing receptors (CaSR). The invention also provides herein the pharmaceutical compositions thereof, and methods for treating, managing, and/or lessening the severity of diseases, disorders, syndromes and/or conditions associated with the modulation of CaSR. The invention also relates to process for the preparation of the compounds of the invention.

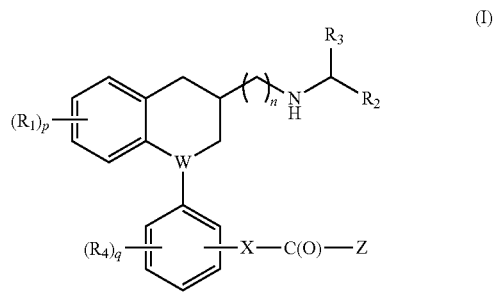

16 Claims, No Drawings

ARYLALKYLAMINE COMPOUNDS AS CALCIUM SENSING RECEPTOR MODULATORS

RELATED APPLICATIONS

The present application claims the benefit of priority to Indian Provisional Patent Application Nos. 988/KOL/2012, filed on Aug. 27, 2012 and 1031/KOL/2012 filed on Sep. 10, 2012.

FIELD OF THE INVENTION

The present invention relates to arylalkylamine compounds, pharmaceutically acceptable salts thereof and pharmaceutical compositions for the treatment, management, and/or lessening the severity of diseases, disorders, syndromes or conditions associated with the modulation of calcium sensing receptors (CaSR). The invention also relates to method of treating, managing and/or lessening the severity of diseases disorders, syndromes or conditions associated with the modulation of calcium sensing receptors (CaSR). The invention also relates to processes for the preparation of the compounds of the invention.

BACKGROUND OF THE INVENTION $Ca^{2+}$ is known to be an intracellular second messenger, with the molecular identification of an extracellular calcium sensing receptor (CaSR), it has further opened the possibility that $Ca^{2+}$ might also function as a messenger outside the cells. Information about the local changes in extracellular concentration of $Ca^{2+}$ is conveyed to the interior of many types of cells through this unique receptor.

Calcium-sensing receptor (CaSR) is a G-protein-coupled receptor (GPCR) that signals through the activation of phospholipase C, increasing levels of inositol 1,4,5-triphosphate and cytosolic calcium. The CaSR belongs to the subfamily C of the GPCR superfamily Structurally, CaSR has an exceptionally large amino-terminal extracellular (ECD) domain (about 600 amino acids), a feature that is shared by all of the members of the family C GPCRs.

In mammals, the expression of CaSR is quite ubiquitous and its presence in the parathyroid gland plays an important role in the secretion of parathyroid hormone (PTH). The reduction in serum calcium leads to the secretion of PTH. Consequently, PTH secretion leads to conservation of serum $Ca^{2+}$ by increasing kidney retention and intestinal absorption of $Ca^{2+}$. This happens indirectly through the PTH-induced synthesis of the active vitamin D metabolite, 25-dihydroxy vitamin D. In addition, the pulsatile action of PTH has anabolic effects on bone development and its sustained levels can lead to catabolic effects, in which the bones breakdown releasing $Ca^{2+}$ as in the case of osteoporosis. All these systems converge in maintenance of baseline serum $Ca^{2+}$ and it involves a tight regulation between serum PTH and extracellular calcium which is mediated by the remarkable receptor CaSR.

In conditions such as primary and secondary hyperparathyroidism, there is excessive secretion of parathyroid hormone due to hyperplasia of the glands. The most common cause of primary hyperparathyroidism (PHPT) is parathyroid adenoma resulting from clonal mutations (~97%) and associated hypercalcemia. In the case of secondary hyperparathyroidism (SHPT), it is most commonly seen in patients with chronic renal failure. The kidneys fail to convert enough vitamin D to its active form and also does not adequately excrete phosphorous. Excess phosphorous further depletes serum calcium by forming calcium phosphate (kidney stones) leading to hypocalcemia.

Small molecules that are positive allosteric modulators called calcimimetics modulate and improve the receptors sensitivity to the already existing milieu of extracellular ionic calcium. This would eventually translate in lowering plasma PTH levels thereby improving conditions of hyperparathyroidism, calcium homeostasis and bone metabolism. WO 2012/127388, WO 2012/120476, WO 2012/127385, WO 2012/069421, WO 2012/069419, WO 2012/069402, US 2011/0028452, WO 2010/150837, WO 2010/136037, WO 2010/042642, WO 2010/038895, WO 2009/065406, WO 2008/059854, WO 2006/123725, WO 2004/106280, WO 2004/069793, WO 2002/012181 and US 2003/0199497 applications disclose the compounds related to calcium sensing receptors (CaSR) for the treatment of various diseases mediated by CaSR. And also *J. Med. Chem.* (2006), 49, 5119-5128 discloses the compounds related to calcium sensing receptors (CaSR).

SUMMARY OF THE INVENTION

In accordance with one aspect, the invention provides compounds having the structure of Formula (I),

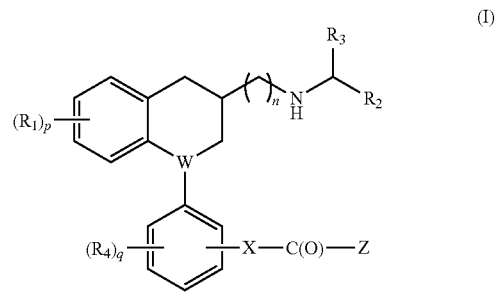

wherein,

W is CH or N;

$R_1$, which may be same or different at each occurrence, is independently selected from halogen, nitro, cyano, substituted or unsubstituted alkyl, substituted or unsubstituted haloalkyl, substituted or unsubstituted cycloalkyl, —C(O)OR$_5$, —(CR$_a$R$_b$)$_r$—C(O)OR$_5$, —O—C(O)OR$_5$, —O(CR$_a$R$_b$)$_r$—C(O)OR$_5$, —NR$_6$R$_7$, —C(O)R$_8$, —C(O)NR$_6$R$_7$, —NR$_6$C(O)R$_8$, —S(O)$_{0-2}$R$_5$, —S(O)$_2$NR$_6$R$_7$, and —NR$_6$S(O)$_2$R$_8$;

$R_2$ is substituted or unsubstituted aryl;

$R_3$ is substituted or unsubstituted alkyl;

$R_4$, which may be same or different at each occurrence, is independently selected from halogen, cyano, substituted or unsubstituted alkyl, substituted or unsubstituted haloalkyl, —OR$_5$, —NR$_6$R$_7$, —C(O)R$_8$, —C(O)NR$_6$R$_7$, —NR$_6$C(O)R$_8$, —S(O)$_{0-2}$R$_5$, —S(O)$_2$NR$_6$R$_7$, and —NR$_5$S(O)$_2$R$_8$;

X is selected from a bond, —(CR$_a$R$_b$)$_r$—, —O—, —NR$_7$—, —O(CR$_a$R$_b$)$_r$—, —C(O)NR$_7$—, —C(O)NR$_7$(CR$_a$R$_b$)$_r$—, —(CR$_a$R$_b$)$_r$cycloalkylene-, cycloalkylene, cycloalkylene-(CR$_a$R$_b$)$_r$—, and —O-cycloalkylene;

$R_a$ and $R_b$, which may be same or different at each occurrence, are independently selected from hydrogen, halogen, hydroxy, cyano, substituted or unsubstituted alkyl, substituted or unsubstituted haloalkyl and substituted or unsubstituted cycloalkyl; or $R_a$ and $R_b$, together with the carbon atom to which they are attached, may form a substituted or unsubstituted 3 to 7 membered saturated carbocyclic ring;

Z is —OR$_5$ or —NR$_6$R$_7$;

R$_5$, which may be same or different at each occurrence, is independently selected from hydrogen, substituted or unsubstituted alkyl, substituted or unsubstituted haloalkyl, and substituted or unsubstituted aryl;

R$_6$ and R$_7$, which may be same or different at each occurrence, are independently selected from hydrogen, substituted or unsubstituted alkyl, —(CR$_a$R$_b$)$_r$—C(O)OR$_5$, substituted or unsubstituted cycloalkyl, substituted or unsubstituted cycloalkylalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, and substituted or unsubstituted heterocyclylalkyl; or R$_6$ and R$_7$, together with the nitrogen atom to which they are attached, may form a substituted or unsubstituted, saturated or unsaturated 3 to 10 membered cyclic ring, wherein the unsaturated cyclic ring may have one or two double bonds;

at each occurrence, R$_8$ is substituted or unsubstituted alkyl or substituted or unsubstituted aryl;

'n' is an integer ranging from 0 to 3, both inclusive;
'p' is an integer ranging from 0 to 3, both inclusive;
'q' is an integer ranging from 0 to 3, both inclusive; and
'r' is an integer ranging from 1 to 3, both inclusive;
or a pharmaceutically acceptable salt thereof.

According to one embodiment, there are provided compounds of the Formula (II):

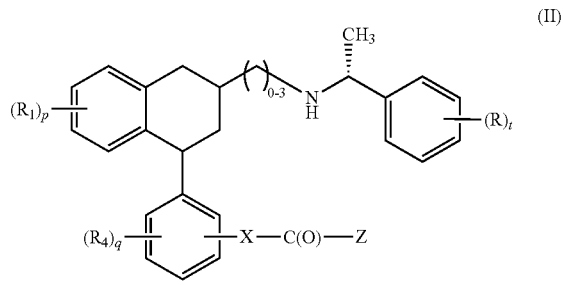

(II)

or its pharmaceutically acceptable salt thereof;
wherein,

R, which may be same or different at each occurrence, is independently selected from halogen, hydroxy, substituted or unsubstituted alkyl, substituted or unsubstituted haloalkyl, and substituted or unsubstituted alkoxy;

't' is an integer ranging from 0 to 3, both inclusive;

R$_1$, R$_4$, X, Z, 'p' and 'q' are as defined in Formula (I).

According to one embodiment, there are provided compounds of the Formula (III):

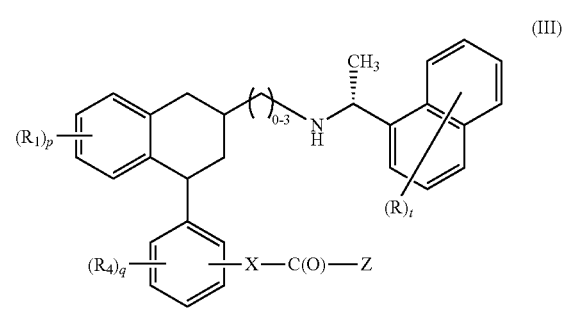

(III)

or its pharmaceutically acceptable salt thereof;

wherein,
R, which may be same or different at each occurrence, is independently selected from hydroxy, substituted or unsubstituted alkyl, substituted or unsubstituted haloalkyl, and substituted or unsubstituted alkoxy;

't' is an integer ranging from 0 to 3, both inclusive;

R$_1$, R$_4$, X, Z, 'p' and 'q' are as defined in Formula (I).

According to one embodiment, there are provided compounds of the Formula (IV):

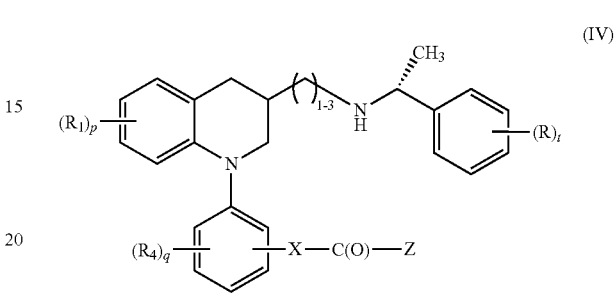

(IV)

or its pharmaceutically acceptable salt thereof;
wherein,

R, which may be same or different at each occurrence, is independently selected from halogen, hydroxy, substituted or unsubstituted alkyl, substituted or unsubstituted haloalkyl, and substituted or unsubstituted alkoxy;

't' is an integer ranging from 0 to 3, both inclusive;

R$_1$, R$_4$, X, Z, 'p' and 'q' are as defined in Formula (I).

According to another embodiment, there are provided compounds of the Formula (V):

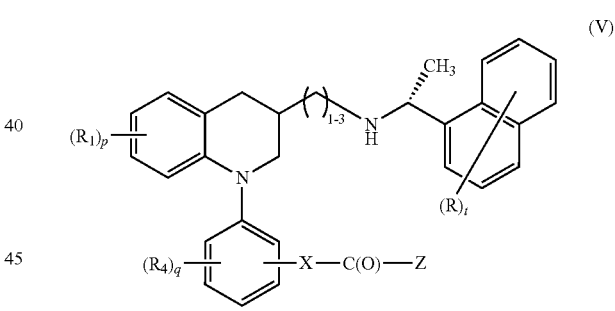

(V)

or its pharmaceutically acceptable salt thereof;
wherein,

R, which may be same or different at each occurrence, is independently selected from halogen, hydroxy, substituted or unsubstituted alkyl, substituted or unsubstituted haloalkyl, and substituted or unsubstituted alkoxy;

't' is an integer ranging from 0 to 3, both inclusive;

R$_1$, R$_4$, X, Z, 'p' and 'q' are as defined in Formula (I).

It should be understood that the Formula (I), Formula (II), Formula (III), Formula (IV), and/or Formula (V) structurally encompasses all tautomers, stereoisomers, enantiomers and diastereomers, including isotopes wherever applicable and pharmaceutically acceptable salts that may be contemplated from the chemical structure of the genera described herein.

The details of one or more embodiments of the invention set forth in the below are illustrative in nature only and not intended to limit to the scope of the invention. Other features, objects and advantages of the inventions will be apparent from the description and claims According to one embodiment, there are provided compounds of Formula (I) in which 'n' is 0.

According to another embodiment, there are provided compounds of Formula (I) in which 'n' is 1.

According to another embodiment, there are provided compounds of Formula (I) in which 'n' is 2.

According to another embodiment, there are provided compounds of Formula (I) in which 'n' is 3.

According to another embodiment, there are provided compounds of Formula (I), in which 'q' is 0, 1 or 2.

According to another embodiment, there are provided compounds of Formula (I), (II), (III), (IV) and/or (V) in which $R_1$ is selected from halogen, cyano, substituted or unsubstituted alkyl, and substituted or unsubstituted haloalkyl; and 'p' is 0, 1 or 2.

According to another embodiment, there are provided compounds of Formula (I) in which $R_2$ is substituted or unsubstituted aryl. In this embodiment $R_2$ is substituted or unsubstituted phenyl or substituted or unsubstituted naphthyl wherein the substituent(s) may be one or more, same or different and are independently selected from halogen, hydroxy, substituted or unsubstituted alkyl, substituted or unsubstituted haloalkyl, and substituted or unsubstituted alkoxy.

According to another embodiment, there are provided compounds of Formula (I), (II), (III), (IV) and/or (V) in which X is bond, —($CR_aR_b$)$_r$—, —O—, —O($CR_aR_b$)$_r$—, —C(O)NR$_7$—, —C(O)NR$_7$($CR_aR_b$)$_r$—, —($CR_aR_b$)$_r$cycloalkylene-, cycloalkylene, cycloalkylene-($CR_aR_b$)$_r$—, and —O-cycloalkylene; wherein $R_a$ and $R_b$ are independently a hydrogen or substituted or unsubstituted alkyl; $R_7$ is a hydrogen or substituted or unsubstituted alkyl; and 'r' is 1 or 2.

According to another embodiment, there are provided compounds of Formula (I), (II), (III), (IV) and/or (V) in which Z is —OR$_5$ where $R_5$ is hydrogen or substituted or unsubstituted alkyl.

According to another embodiment, there are provided compounds of Formula (I), (II), (III), (IV) and/or (V) in which Z is —NR$_6$R$_7$ where $R_6$ and $R_7$ are independently a hydrogen or substituted or unsubstituted alkyl.

According to another embodiment, there are provided compounds of Formula (I), (II), (III), (IV) and/or (V) in which $R_4$ is halogen, cyano, substituted or unsubstituted alkyl, substituted or unsubstituted haloalkyl or —OR$_5$ where $R_5$ is hydrogen or substituted or unsubstituted alkyl and 'q' is 0, 1 or 2.

According to another embodiment, there are provided compounds of the Formula (V):

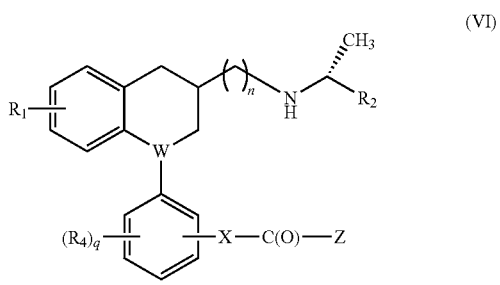

(VI)

wherein,
W is CH or N;
$R_1$ is hydrogen or halogen;

$R_2$ is substituted or unsubstituted aryl wherein the aryl is substituted or unsubstituted phenyl or substituted or unsubstituted naphthyl and the substituents are halogen or substituted or unsubstituted alkoxy;

$R_4$ is halogen, or substituted or unsubstituted alkyl;

X is selected from a bond, —$CR_aR_b$—, —O—$CR_aR_b$—, and —C(O)NR$_7$—$CR_aR_b$—;

$R_a$ and $R_b$ are hydrogen, substituted or unsubstituted alkyl;

Z is —OR$_5$ or —NR$_6$R$_7$;

$R_5$ is hydrogen or substituted or unsubstituted alkyl;

$R_6$ and $R_7$ are independently a hydrogen or substituted or unsubstituted alkyl 'n' is an integer ranging from 0 to 3, both inclusive; and 'q' is an integer ranging from 0 to 2, both inclusive;

or a pharmaceutically acceptable salt thereof.

Below are the representative compounds, which are illustrative in nature only and are not intended to limit to the scope of the invention.

3-(3-((((R)-1-(Naphthalen-1-yl)ethyl)amino)methyl)-1,2,3,4-tetrahydronaphthalen-1-yl)benzoic acid hydrochloride, 2-Fluoro-5-(3-((((R)-1-(naphthalen-1-yl)ethyl)amino)methyl)-1,2,3,4-tetrahydronaphthalen-1-yl)benzoic acid hydrochloride, 2-Methyl-5-(3-((((R)-1-(naphthalen-1-yl)ethyl)amino)methyl)-1,2,3,4-tetrahydronaphthalen-1-yl)benzoic acid hydrochloride, 3-Methyl-5-(3-((((R)-1-(naphthalen-1-yl)ethyl)amino)methyl)-1,2,3,4-tetrahydronaphthalen-1-yl)benzoic acid hydrochloride, 2,6-Dimethyl-3-(3-((((R)-1-(naphthalen-1-yl)ethyl)amino)methyl)-1,2,3,4-tetrahydronaphthalen-1-yl)benzoic acid hydrochloride, 2-Methyl-4-((3S)-3-((((R)-1-(naphthalen-1-yl)ethyl)amino)methyl)-1,2,3,4-tetrahydronaphthalen-1-yl)benzoic acid hydrochloride, 4-Methyl-3-((3S)-3-((((R)-1-(naphthalen-1-yl)ethyl)amino)methyl)-1,2,3,4-tetrahydronaphthalen-1-yl)benzoic acid hydrochloride, 5-((3S)-3-((((R)-1-(4-Fluoro-3-methoxyphenyl)ethyl)amino)methyl)-1,2,3,4-tetrahydronaphthalen-1-yl)-2-methylbenzoic acid hydrochloride, 3-((3S)-3-((((R)-1-(4-Fluoro-3-methoxyphenyl)ethyl)amino)methyl)-1,2,3,4-tetrahydronaphthalen-1-yl)-2,6-dimethylbenzoic acid hydrochloride, 5-((3S)-3-((((R)-1-(4-Fluoronaphthalen-1-yl)ethyl)amino)methyl)-1,2,3,4-tetrahydronaphthalen-1-yl)-2-methylbenzoic acid hydrochloride, 2-Methyl-5-(3-(((R)-1-(naphthalen-1-yl)ethyl)amino)-1,2,3,4-tetrahydronaphthalen-1-yl)benzoic acid hydrochloride, 2-Methyl-4-(3-(((R)-1-(naphthalen-1-yl)ethyl)amino)-1,2,3,4-tetrahydronaphthalen-1-yl)benzoic acid hydrochloride, 5-((3S)-3-(2-(((R)-1-(4-Fluoronaphthalen-1-yl)ethyl)amino)ethyl)-1,2,3,4-tetrahydronaphthalen-1-yl)-2-methylbenzoic acid hydrochloride, 2-Methyl-5-((3S)-3-(2-(((R)-1-(naphthalen-1-yl)ethyl)amino)ethyl)-1,2,3,4-tetrahydronaphthalen-1-yl)benzoic acid hydrochloride, 5-((3S)-3-(3-(((R)-1-(4-fluoronaphthalen-1-yl)ethyl)amino)propyl)-1,2,3,4-tetrahydronaphthalen-1-yl)-2-methylbenzoic acid hydrochloride, 2-Methyl-5-((3R)-3-(3-(((R)-1-(naphthalen-1-yl)ethyl)amino)propyl)-1,2,3,4-tetrahydronaphthalen-1-yl)benzoic acid hydrochloride, 5-((3S)-3-(3-(((R)-1-(4-Fluoro-3-methoxyphenyl)ethyl)amino)propyl)-1,2,3,4-tetrahydronaphthalen-1-yl)-2-methylbenzoic acid hydrochloride, 2-Methyl-5-(3-((((R)-1-(naphthalen-1-yl)ethyl)amino)methyl)-3,4-dihydroquinolin-1(2H)-yl)benzoic acid hydrochloride, 4-Methyl-3-(3-((((R)-1-(naphthalen-1-yl)ethyl)amino)methyl)-3,4-dihydroquinolin-1(2H)-yl)benzoic acid hydrochloride, 2,6-Dimethyl-3-(3-((((R)-1-(naphthalen-1-yl)ethyl)amino)methyl)-3,4-dihydroquinolin-1(2H)-yl)benzoic acid hydrochloride, 5-(3-((((R)-1-(4-Fluoro naphthalen-1-yl)ethyl)amino)methyl)-3,4-dihydroquinolin-1(2H)-yl)-2-methylbenzoic acid hydrochloride, 5-(3-((((R)-1-(4-Fluoro-3-methoxyphenyl)ethyl)amino)methyl)-3,4-dihydroquinolin-1(2H)-yl)-2-methylbenzoic acid hydrochloride, 2-Methyl-4-(3-((((R)-1-(naphthalen-1-yl)ethyl)amino)methyl)-3,4-dihydroquinolin-1(2H)-yl)benzoic acid hydrochloride, 5-(6-Fluoro-3-((((R)-1-(naphthalen-1-yl)ethyl)amino)methyl)-3,4-dihydroquinolin-1(2H)-yl)-2-methyl benzoic acid hydrochloride, 2-Methyl-5-(3-(2-(((R)-1-(naphthalen-1-yl)ethyl)amino)ethyl)-3,4-dihydroquinolin-1(2H)-yl)benzoic acid hydrochloride, 2-(2-methyl-5-(3-(2-(((R)-1-(naphthalen-1-yl)ethyl)amino)ethyl)-3,4-dihydroquinolin-1(2H)-yl)phenoxy)acetic acid hydrochloride, 2-Methyl-5-(3-(3-(((R)-1-(naphthalen-1-yl)ethyl)amino)propyl)-3,4-dihydroquinolin-1(2H)-yl)benzoic acid hydrochloride, 3-(3-(3-(((R)-1-(4-Fluoro naphthalen-1-yl)ethyl)amino)propyl)-3,4-dihydroquinolin-1(2H)-yl)-2-methyl benzoic acid hydrochloride, 2-(2-Methyl-5-(3-(3-(((R)-1-(naphthalen-1-yl)ethyl)amino)propyl)-3,4-dihydroquinolin-1(2H)-yl)phenoxy)acetic acid hydrochloride, 2-Methyl-3-(3-((((R)-1-(naphthalen-1-yl)ethyl)amino)methyl)-1,2,3,4-tetrahydronaphthalen-1-yl)benzoic acid hydrochloride, 2,4-Dimethyl-5-(3-((((R)-1-(naphthalen-1-yl)ethyl)amino)methyl)-1,2,3,4-tetrahydronaphthalen-1-yl)benzoic acid hydrochloride, 2-Fluoro-3-(3-((((R)-1-(naphthalen-1-yl)ethyl)amino)methyl)-1,2,3,4-tetrahydronaphthalen-1-yl)benzoic acid hydrochloride, 4-Fluoro-3-(3-((((R)-1-(naphthalen-1-yl)ethyl)amino)methyl)-1,2,3,4-tetrahydronaphthalen-1-yl)benzoic acid hydrochloride, 2,3-Dimethyl-5-(3-((((R)-1-(naphthalen-1-yl)ethyl)amino)methyl)-1,2,3,4-tetrahydronaphthalen-1-yl)benzoic acid hydrochloride, 2-(3-(3-((((R)-1-(Naphthalen-1-yl)ethyl)amino)methyl)-1,2,3,4-tetrahydronaphthalen-1-yl)benzamido)acetic acid hydrochloride, 2-Fluoro-5-(3-(2-(((R)-1-(naphthalen-1-yl)ethyl)amino)ethyl)-1,2,3,4-tetrahydronaphthalen-1-yl)benzoic acid hydrochloride, 3-Methyl-5-(3-(2-(((R)-1-(naphthalen-1-yl)ethyl)amino)ethyl)-1,2,3,4-tetrahydronaphthalen-1-yl)benzoic acid hydrochloride, 2,6-Dimethyl-3-(3-(2-(((R)-1-(naphthalen-1-yl)ethyl)amino)ethyl)-1,2,3,4-tetrahydronaphthalen-1-yl)benzoic acid hydrochloride, 2-Methyl-3-(3-(2-(((R)-1-(naphthalen-1-yl)ethyl)amino)ethyl)-1,2,3,4-tetrahydronaphthalen-1-yl)benzoic acid hydrochloride, 4-Methyl-3-(3-(2-(((R)-1-(naphthalen-1-yl)ethyl)amino)ethyl)-1,2,3,4-tetrahydronaphthalen-1-yl)benzoic acid hydrochloride, 2,4-Dimethyl-5-(3-(2-(((R)-1-(naphthalen-1-yl)ethyl)amino)ethyl)-1,2,3,4-tetrahydronaphthalen-1-yl)benzoic acid hydrochloride, 2-Methyl-4-(3-(2-(((R)-1-(naphthalen-1-yl)ethyl)amino)ethyl)-1,2,3,4-tetrahydronaphthalen-1-yl)benzoic acid hydrochloride, 5-(3-(2-(((R)-1-(4-Fluoro-3-methoxyphenyl)ethyl)amino)ethyl)-1,2,3,4-tetrahydronaphthalen-1-yl)-2-methylbenzoic acid hydrochloride, 2,3-Dimethyl-5-(3-(2-(((R)-1-(naphthalen-1-yl)ethyl)amino)ethyl)-1,2,3,4-tetrahydronaphthalen-1-yl)benzoic acid hydrochloride, 3-Methyl-5-(3-(3-(((R)-1-(naphthalen-1-yl)ethyl)amino)propyl)-1,2,3,4-tetrahydronaphthalen-1-yl)benzoic acid hydrochloride, 2,6-Dimethyl-3-(3-(3-(((R)-1-(naphthalen-1-yl)ethyl)amino)propyl)-1,2,3,4-tetrahydronaphthalen-1-yl)benzoic acid hydrochloride, 2-Methyl-3-(3-(3-(((R)-1-(naphthalen-1-yl)ethyl)amino)propyl)-1,2,3,4-tetrahydronaphthalen-1-yl)benzoic acid hydrochloride, 4-Methyl-3-(3-(3-(((R)-1-(naphthalen-1-yl)ethyl)amino)propyl)-1,2,3,4-tetrahydronaphthalen-1-yl)benzoic acid hydrochloride, 2,4-Dimethyl-5-(3-(3-(((R)-1-(naphthalen-1-yl)ethyl)amino)propyl)-1,2,3,4-tetrahydronaphthalen-1-yl)benzoic acid hydrochloride, 2-Methyl-4-(3-(3-(((R)-1-(naphthalen-1-yl)ethyl)amino)propyl)-1,2,3,4-tetrahydronaphthalen-1-yl)benzoic acid hydrochloride, 5-(3-(3-(((R)-1-(4-Fluoro-3-methoxyphenyl)ethyl)amino)propyl)-1,2,3,4-tetrahydronaphthalen-1-yl)-2-methylbenzoic acid hydrochloride and 2,3-Dimethyl-5-(3-(3-(((R)-1-(naphthalen-1-yl)ethyl)amino)propyl)-1,2,3,4-tetrahydronaphthalen-1-yl)benzoic acid hydrochloride or a pharmaceutically acceptable salt thereof, or their stereoisomers thereof.

In another aspect of the invention, there is provided a compound of Formula (I) useful in treating, managing and/or lessening the severity of diseases, disorders, syndromes or conditions associated with calcium sensing receptor (CaSR) modulators.

In another aspect, the invention provides a pharmaceutical composition comprising at least one compound of Formula (I) and at least one pharmaceutically acceptable excipient.

In another aspect, the invention provides a pharmaceutical composition of compound of Formula (I) useful in treating, managing and/or lessening the severity of the diseases disorders, syndromes or conditions associated with calcium sensing receptor (CaSR) modulators in a subject, in need thereof by administering to the subject, one or more compounds described herein in a therapeutically effective amount to cause modulation of such receptor.

In another aspect, the invention provides a pharmaceutical composition comprising a compound of Formula (I) or a pharmaceutically acceptable salt thereof together with a pharmaceutically acceptable excipient.

In another aspect, there are provided processes for the preparation compounds of Formula (Ia):

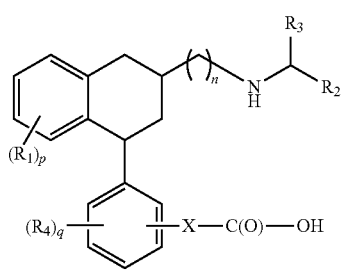

(Ia)

wherein, $R_1$, $R_2$, $R_3$, $R_4$, X, 'p' and 'q' are as defined in herein above;

the process comprising the steps:

a) converting a keto group in Formula (6a, 6b, 6c) where 'n' is 1, 2, or 3, into enol-triflate using 1,1,1-trifluoro-N-phenyl-N-((trifluoromethyl)sulfonyl)methanesulfonamide in presence of potassium bis(trimethylsilyl)amide (KHMDS) to give compound of Formula (20);

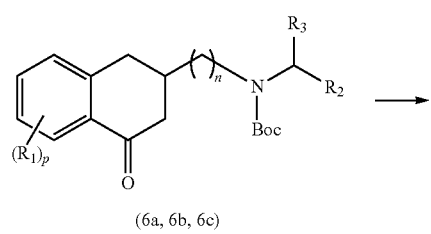

(6a, 6b, 6c)
'n' is 1, 2, 3;

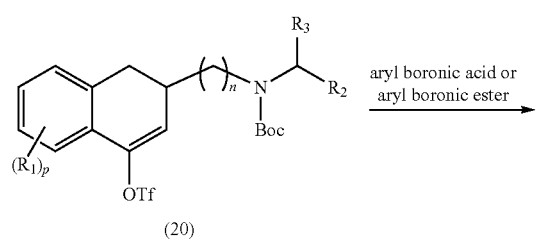

(20)

b) coupling of enol-triflate of compound of Formula (20) with suitable aryl boronic acids or aryl boronic ester in presence of a base and tetrakis(triphenylphosphine)palladium(0) to give compound of Formula (21);

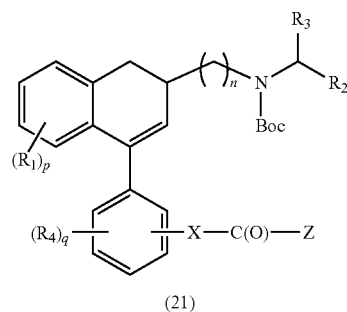

(21)

c) reducing a compound of Formula (21) using palladium on carbon (10%) to give compound of Formula (22);

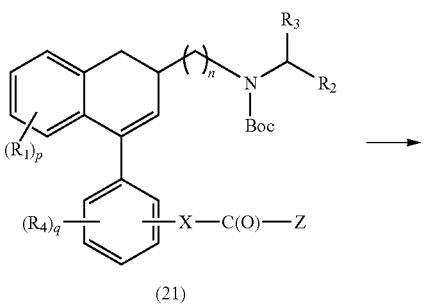

(21)

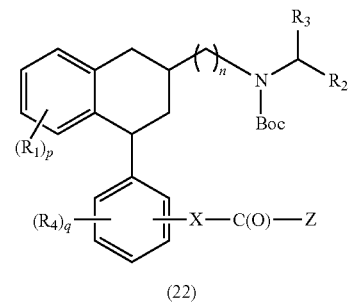

(22)

d) deprotecting a Boc functional group using HCl in suitable solvent to get compound of Formula (23)

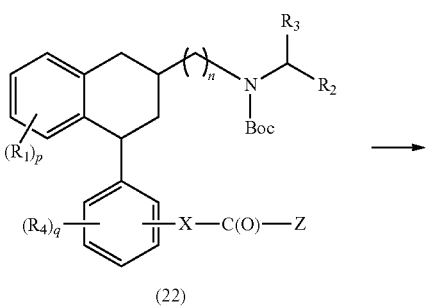

(22)

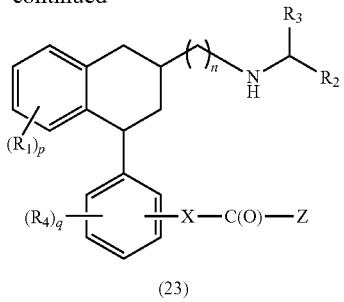

(23)

e) hydrolyzing an ester group of compound of Formula (23) (when Z is -o-alkyl or O-benzyl) using base to afford corresponding acid compound of Formula (Ia)

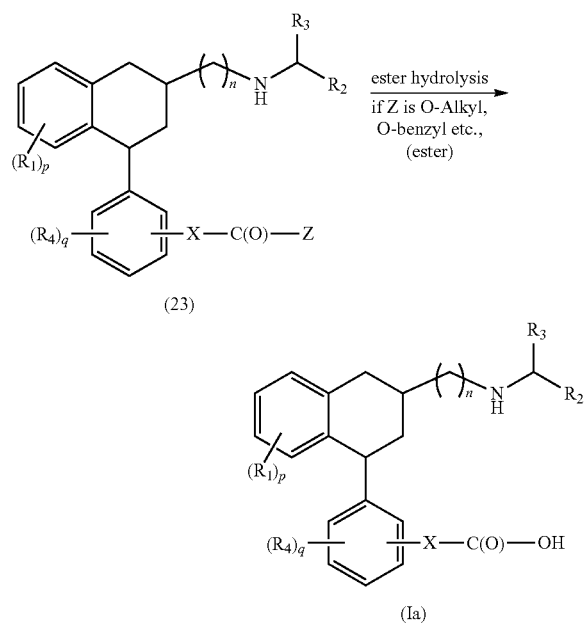

DETAILED DESCRIPTION OF THE INVENTION

Definitions

Unless otherwise stated, the following terms used in the specification and claims have the meanings given below.

For purposes of interpreting the specification and claims, the following definitions will apply and whenever appropriate, terms used in the singular will also include the plural and vice versa.

The terms "halogen" or "halo" means fluorine, chlorine, bromine, or iodine.

The term "alkyl" refers to an alkane derived hydrocarbon radical that includes solely carbon and hydrogen atoms in the backbone, contains no unsaturation, has from one to six carbon atoms, and is attached to the remainder of the molecule by a single bond, e.g., methyl, ethyl, n-propyl, 1-methylethyl (isopropyl), n-butyl, n-pentyl, 1,1-dimethylethyl (t-butyl) and the like. Unless set forth or recited to the contrary, all alkyl groups described or claimed herein may be straight chain or branched, substituted or unsubstituted.

The term "alkenyl" refers to a hydrocarbon radical containing from 2 to 10 carbon atoms and including at least one carbon-carbon double bond. Non-limiting examples of alkenyl groups include ethenyl, 1-propenyl, 2-propenyl (allyl), iso-propenyl, 2-methyl-1-propenyl, 1-butenyl, 2-butenyl and the like. Unless set forth or recited to the contrary, all alkenyl groups described or claimed herein may be straight chain or branched, substituted or unsubstituted.

The term "alkynyl" refers to a hydrocarbon radical containing 2 to 10 carbon atoms and including at least one carbon-carbon triple bond. Non-limiting examples of alkynyl groups include ethynyl, propynyl, butynyl and the like. Unless set forth or recited to the contrary, all alkynyl groups described or claimed herein may be straight chain or branched, substituted or unsubstituted.

The term "alkoxy" refers to an alkyl group attached via an oxygen linkage. Non-limiting examples of such groups are methoxy, ethoxy and propoxy and the like. Unless set forth or recited to the contrary, all alkoxy groups described or claimed herein may be straight chain or branched, substituted or unsubstituted.

The term "haloalkyl" refers to an alkyl group as defined above that is substituted by one or more halogen atoms as defined above. Preferably, the haloalkyl may be monohaloalkyl, dihaloalkyl or polyhaloalkyl including perhaloalkyl. A monohaloalkyl can have one iodine, bromine, chlorine or fluorine atom. Dihaloalkyl and polyhaloalkyl groups can be substituted with two or more of the same halogen atoms or a combination of different halogen atoms. Preferably, a polyhaloalkyl is substituted with up to 12 halogen atoms. Non-limiting examples of a haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl and the like. A perhaloalkyl refers to an alkyl having all hydrogen atoms replaced with halogen atoms. Unless set forth or recited to the contrary, all haloalkyl groups described or claimed herein may be straight chain or branched, substituted or unsubstituted.

The term "cycloalkyl" refers to a non-aromatic mono or multicyclic ring system having 3 to 12 carbon atoms, such as cyclopropyl, cyclobutyl, cyclopentyl, cyclohexyl and the like. Examples of multicyclic cycloalkyl groups include, but are not limited to, perhydronapthyl, adamantyl and norbornyl groups, bridged cyclic groups or spirobicyclic groups, e.g., spiro(4,4)non-2-yl and the like. Unless set forth or recited to the contrary, all cycloalkyl groups described or claimed herein may be substituted or unsubstituted.

The term "cycloalkylene" refers to a saturated divalent cyclic hydrocarbon radical that includes solely carbon and hydrogen atoms in the backbone. In particular, "$C_3$-$C_7$ cycloalkylene" means a saturated divalent cyclic hydrocarbon radical with 3 to 7 carbon atoms e.g. cyclopropylene, cyclobutylene, cyclopentylene, cyclohexylene and the like. Unless set forth or recited to the contrary, all cycloalkylene groups described or claimed herein may be substituted or unsubstituted.

The term "cycloalkenyl" refers to a non-aromatic mono or multicyclic ring system having 3 to 12 carbon atoms and including at least one carbon-carbon double bond, such as cyclopentenyl, cyclohexenyl, cycloheptenyl and the like. Unless set forth or recited to the contrary, all cycloalkenyl groups described or claimed herein may be substituted or unsubstituted.

The term "cycloalkylalkyl" refers to a cycloalkyl group as defined above, directly bonded to an alkyl group as defined above, e.g., cyclopropylmethyl, cyclobutylmethyl, cyclopentylmethyl, cyclohexylmethyl, cyclohexylethyl, etc. Unless set forth or recited to the contrary, all cycloalkylalkyl groups described or claimed herein may be substituted or unsubstituted.

The term "aryl" refers to an aromatic radical having 6- to 14-carbon atoms, including monocyclic, bicyclic and tricyclic aromatic systems, such as phenyl, naphthyl, tetrahydronaphthyl, indanyl, and biphenyl and the like. Unless set forth or recited to the contrary, all aryl groups described or claimed herein may be substituted or unsubstituted. The term "arylalkyl" refers to an aryl group as defined above directly bonded to an alkyl group as defined above, e.g., —$CH_2C_6H_5$ and —$C_2H_4C_6H_5$. Unless set forth or recited to the contrary, all arylalkyl groups described or claimed herein may be substituted or unsubstituted.

A "carbocyclic ring" or "carbocycle" as used herein refers to a 3- to 10-membered saturated or unsaturated, monocyclic, fused bicyclic, spirocyclic or bridged polycyclic ring containing carbon atoms, which may optionally be substituted, for example, carbocyclic rings include but are not limited to cyclopropyl, cyclobutyl, cyclopentyl, cyclohexyl, cyclopropylene, cyclohexanone, aryl, naphthyl, adamantyl etc. Unless set forth or recited to the contrary, all carbocyclic groups or rings described or claimed herein may be aromatic or non-aromatic.

A "3 to 7" membered saturated carbocyclic ring" as used herein refers to a monocyclic non aromatic ring systems.

A "3 to 10" membered cyclic ring" as used herein refers to a monocyclic, bicyclic, polycyclic heteroaryl or heterocyclic ring systems.

The term "heterocyclic ring" or "heterocyclyl ring" or "heterocyclyl", unless otherwise specified, refers to substituted or unsubstituted non-aromatic 3- to 15-membered ring which consists of carbon atoms and with one or more heteroatom(s) independently selected from N, O or S. The heterocyclic ring may be a mono-, bi- or tricyclic ring system, which may include fused, bridged or spiro ring systems and the nitrogen, carbon, oxygen or sulfur atoms in the heterocyclic ring may be optionally oxidized to various oxidation states. In addition, the nitrogen atom may be optionally quaternized, the heterocyclic ring or heterocyclyl may optionally contain one or more olefinic bond(s), and one or two carbon atoms(s) in the heterocyclic ring or heterocyclyl may be interrupted with —$CF_2$—, —C(O)—, —S(O)—, $S(O)_2$, —C(=N-alkyl)-, or —C(=N-cycloalkyl), etc. In addition heterocyclic ring may also be fused with aromatic ring. Non-limiting examples of heterocyclic rings include azetidinyl, benzopyranyl, chromanyl, decahydroisoquinolyl, indanyl, indolinyl, isoindolinyl, isochromanyl, isothiazolidinyl, isoxazolidinyl, morpholinyl, oxazolinyl, oxazolidinyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisoquinolyl, tetrahydrofuryl, tetrahydropyranyl, thiazolinyl, thiazolidinyl, thiamorpholinyl, thiamorpholinyl sulfoxide, thiamorpholinyl sulfone indoline, benzodioxole, tetrahydroquinoline, tetrahydrobenzopyran and the like. The heterocyclic ring may be attached by any atom of the heterocyclic ring that results in the creation of a stable structure. Unless set forth or recited to the contrary, all heterocyclyl groups described or claimed herein may be substituted or unsubstituted; substituents may be on same or different ring atom.

The term "heteroaryl" unless otherwise specified, refers to a substituted or unsubstituted 5- to 14-membered aromatic heterocyclic ring with one or more heteroatom(s) independently selected from N, O or S. The heteroaryl may be a mono-, bi- or tricyclic ring system. The heteroaryl ring may be attached by any atom of the heteroaryl ring that results in the creation of a stable structure. Non-limiting examples of a heteroaryl ring include oxazolyl, isoxazolyl, imidazolyl, furyl, indolyl, isoindolyl, pyrrolyl, triazolyl, triazinyl, tetrazolyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl, phthalazinyl and the like. Unless set forth or recited to the contrary, all heteroaryl groups described or claimed herein may be substituted or unsubstituted.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure. Unless set forth or recited to the contrary, all heterocyclylalkyl groups described or claimed herein may be substituted or unsubstituted.

The term "heteroarylalkyl" refers to a heteroaryl ring radical directly bonded to an alkyl group. The heteroarylalkyl radical may be attached to the main structure at any carbon atom in the alkyl group that results in the creation of a stable structure. Unless set forth or recited to the contrary, all heteroarylalkyl groups described or claimed herein may be substituted or unsubstituted.

Unless otherwise specified, the term "substituted" as used herein refers to a group or moiety having one or more substituents attached to the structural skeleton of the group or moiety. Such substituents include, but are not limited to hydroxy, halogen, carboxyl, cyano, nitro, oxo (=O), thio (=S), alkyl, haloalkyl, alkenyl, alkynyl, aryl, arylalkyl, cycloalkyl, cycloalkylalkyl, cycloalkenyl, heteroaryl, heterocyclic ring, heterocyclylalkyl, heteroarylalkyl, —C(O)$OR^x$, —C(O)$R^x$, —C(S)$R^x$, —C(O)$NR^xR^y$, —$NR^xC(O)NR^yR^z$, —N($R^x$)S(O)$R^y$, —N($R^x$)S(O)$_2R^y$, —$NR^xR^y$, —$NR^xC(O)$ $R^y$, —$NR^xC(S)R^y$, —$NR^xC(S)NR^yR^z$, —S(O)$_2NR^xR^y$, —$OR^x$, —OC(O)$R^x$, —OC(O)$NR^xR^y$, —($CR^xR^y$)$_{0-2}$C(O) $OR^x$, —($CR^xR^y$)$_{0-2}$C(O)$NR^yR^z$, —($CR^xR^y$)$_{0-2}$C(O)$R^y$, —$SR^x$, and —S(O)$_2R^x$; wherein each occurrence of $R^xR^y$ and $R^z$ are independently selected from hydrogen, halogen, alkyl, haloalkyl, alkenyl, alkynyl, aryl, arylalkyl, cycloalkyl, cycloalkenyl, heteroaryl, heterocyclic ring, heterocyclylalkyl and heteroarylalkyl. The aforementioned "substituted" groups cannot be further substituted. For example, when the substituent on "substituted alkyl" is "aryl" or "alkenyl", the aryl or alkenyl cannot be substituted aryl or substituted alkenyl, respectively.

The compounds of the present invention may have one or more chiral centers. The absolute stereochemistry at each chiral center may be 'R' or 'S'. The compounds of the invention include all diastereomers and enantiomers and mixtures thereof. Unless specifically mentioned otherwise, reference to one stereoisomer applies to any of the possible stereoisomers. Whenever the stereoisomeric composition is unspecified, it is to be understood that all possible stereoisomers are included.

The term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. The terms "racemate" or "racemic mixture" refer to a mixture of equal parts of enantiomers.

A "tautomer" refers to a compound that undergoes rapid proton shifts from one atom of the compound to another atom of the compound. Some of the compounds described herein may exist as tautomers with different points of attachment of hydrogen. The individual tautomers as well as mixture thereof are encompassed with compounds of Formula (I).

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; c) lessening the severity of a disease disorder or condition or at least one of its clinical or subclinical symptoms or (d) relieving the disease, i.e., causing regression of the state, disorder or condition or at least one of its clinical or subclinical symptoms.

The term "modulate" or "modulating" or "modulation" or "modulator" refers to an increase in the amount, quality, or effect of a particular activity or function of the receptor. By way of illustration and not limitation, it includes agonists, partial agonists, and allosteric modulators of calcium sensing receptor (CaSR) of the present invention. Such modulation may be contingent on the occurrence of a specific event, such as activation of a signal transduction pathway.

The term "allosteric modulators of calcium-sensing receptor", refers to the ability of a compound that binds to calcium sensing receptors and induces a conformational change that reduces the threshold for calcium sensing receptor activation by the endogenous ligand $Ca^{2+}$ depending on the concentration of the compound exposed to the calcium-sensing receptor.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a disease, disorder, syndrome or condition, is sufficient to cause the effect in the subject which is the purpose of the administration. The "therapeutically effective amount" will vary depending on the compound, the disease and its severity and the age, weight, physical condition and responsiveness of the subject to be treated.

Pharmaceutically Acceptable Salts:

The compounds of the invention may form salts with acid or base. The compounds of invention may be sufficiently basic or acidic to form stable nontoxic acid or base salts, administration of the compound as a pharmaceutically acceptable salt may be appropriate. Non-limiting examples of pharmaceutically acceptable salts are inorganic, organic acid addition salts formed by addition of acids including hydrochloride salts. Non-limiting examples of pharmaceutically acceptable salts are inorganic, organic base addition salts formed by addition of bases. The compounds of the invention may also form salts with amino acids. Pharmaceutically acceptable salts may be obtained using standard procedures well known in the art, for example by reacting a sufficiently basic compound such as an amine with a suitable acid affording a physiologically acceptable anion.

With respect to the overall compounds described by the Formula (I), the invention extends to these stereoisomeric forms and to mixtures thereof. To the extent prior art teaches synthesis or separation of particular stereoisomers, the different stereoisomeric forms of the invention may be separated from one another by a method known in the art, or a given isomer may be obtained by stereospecific or asymmetric synthesis or chiral HPLC (high performance liquid chromatography. Tautomeric forms and mixtures of compounds described herein are also contemplated.

Screening of compounds of invention for calcium sensing receptor (CaSR) modulation activity can be achieved by using various in vitro and in vivo protocols mentioned herein below or methods known in the art.

Pharmaceutical Compositions

The invention relates to pharmaceutical compositions containing the compounds of the Formula (I) disclosed herein. In particular, pharmaceutical compositions containing a therapeutically effective amount of at least one compound of Formula (I) described herein and at least one pharmaceutically acceptable excipient (such as a carrier or diluent). Preferably, the contemplated pharmaceutical compositions include the compound(s) described herein in an amount sufficient to modulate calcium sensing receptor (CaSR) mediated diseases described herein when administered to a subject.

The subjects contemplated include, for example, a living cell and a mammal, including human mammal. The compound of the invention may be associated with a pharmaceutically acceptable excipient (such as a carrier or a diluent) or be diluted by a carrier, or enclosed within a carrier which can be in the form of a capsule, sachet, paper or other container. The pharmaceutically acceptable excipient includes pharmaceutical agent that does not itself induce the production of antibodies harmful to the individual receiving the composition, and which may be administered without undue toxicity.

Examples of suitable carriers or excipients include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, salicylic acid, fatty acids, fatty acid amines, fatty acid monoglycerides and diglycerides, pentaerythritol fatty acid esters, polyoxyethylene, hydroxymethylcellulose and polyvinylpyrrolidone.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared by conventional techniques known in the art. For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, caplets, orally disintegrating tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Solid oral Formulations include, but are not limited to, tablets, caplets, capsules (soft or hard gelatin), orally disintegrating tablets, dragees (containing the active ingredient in powder or pellet form), troches and lozenges. Tablets, dragees, or capsules having talc and/or a carbohydrate carrier or binder or the like are particularly suitable for oral application. Liquid Formulations include, but are not limited to, syrups, emulsions, suspensions, solutions, soft gelatin and sterile injectable liquids, such as aqueous or non-aqueous liquid suspensions or solutions. For parenteral application, particularly suitable are injectable solutions or suspensions, preferably aqueous solutions with the active compound dissolved in polyhydroxylated castor oil.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as pocketed tablets, capsules, and powders in vials or ampoules. Also, the unit dosage form can be a capsule, tablet, caplet, cachet, or lozenge itself, or it can be the appropriate number of any of these in packaged form.

For administration to subject patients, the total daily dose of the compounds of the invention depends, of course, on the mode of administration. For example, oral administration may require a higher total daily dose, than an intravenous (direct into blood). The quantity of active component in a unit dose preparation may be varied or adjusted from 0.1 mg to 10000 mg according to the potency of the active component or mode of administration.

Suitable doses of the compounds for use in treating the diseases and disorders described herein can be determined by those skilled in the relevant art. Therapeutic doses are generally identified through a dose ranging study in subject based on preliminary evidence derived from the animal studies. Doses must be sufficient to result in a desired therapeutic benefit without causing unwanted side effects for the patient. For example, the daily dosage of the CaSR modulator can range from about 0.1 to about 30.0 mg/kg. Mode of administration, dosage forms, suitable pharmaceutical excipients, diluents or carriers can also be well used and adjusted by those skilled in the art. All changes and modifications are envisioned within the scope of the invention.

Methods of Treatment

In another aspect, the invention provides compounds and pharmaceutical compositions thereof that are useful in treating, managing and/or lessening the severity of diseases, disorders, syndromes or conditions modulated by calcium sensing receptor (CaSR). The invention further provides method of treating diseases, disorders, syndromes or conditions modulated by CaSR in a subject in need thereof by administering to the subject a therapeutically effective amount of a compound or a pharmaceutical composition of the invention.

In another aspect of the invention, the methods provided are also useful for diagnosis of conditions that can be treated by modulating CaSR for determining if a patient will be responsible to therapeutic agents.

In another aspect, the invention provides a method for the treatment of diseases, disorders or conditions through modulating CaSR. In this method, a subject in need of such treatment is administered a therapeutically effective amount of a compound of Formula (I) described herein.

The compound and pharmaceutical composition of the present invention is useful to a subject in need of the treatment having a disease, disorder, syndrome or condition characterized by one or more of the following: (a) abnormal calcium ion homeostasis, (b) an abnormal level of a messenger whose production or secretion is affected by the calcium sensing receptor (CaSR) activity or (c) an abnormal level of activity of a messenger whose function is affected by the calcium sensing receptor activity. In one aspect, the patient has a disease, disorder, syndrome or condition characterized by an abnormal level of one or more calcium sensing receptor-regulated components and the compound is active on a CaSR of a cell including parathyroid cell, bone cells (pre-osteoclast, osteoclast, pre-osteoblast, osteoblast), juxtaglomerular kidney cell, kidney messengial cell, glomerular kidney cell, proximal tubule kidney cell, distal tubule kidney cell, cell of the thick ascending limb of Henle's loop and/or collecting duct, Para follicular cell in the thyroid (C-cell), intestinal cell, platelet, vascular smooth muscle cell, gastrointestinal tract cell, pituitary cell or hypothalamic cell. The messenger of the calcium sensing receptor is Calcium.

The compound of Formula (I), being modulators of CaSR, is potentially useful in treating, managing and/or lessening the severity, morbidity/mortality or complications of diseases, disorders, syndromes or conditions include but are not limited to primary hyperparathyroidism, secondary hyperparathyroidism, tertiary hyperparathyroidism, chronic renal failure (with or without dialysis), chronic kidney disease (with or without dialysis) parathyroid adenoma, parathyroid hyperplasia, parathyroid carcinoma, vascular & valvular calcification, abnormal calcium homeostasis such as hypercalcemia, abnormal phosphorous homeostasis such as hypophosphatemia, bone related diseases or complications arising due to hyperparathyroidism, chronic kidney disease or parathyroid carcinoma, bone loss post renal transplantation, osteitis fibrosa cystica, adynamic bone disease, renal bone diseases, cardiovascular complications arising due to hyperparathyroidism or chronic kidney disease, certain malignancies in which $(Ca^{2+})_e$ ions are abnormally high, cardiac, renal or intestinal dysfunctions, podocyte-related diseases, abnormal intestinal motility, diarrhea, augmenting gastrin or gastric acid secretion to directly or indirectly benefit in atrophic gastritis or to improve absorption of pharmacological compounds, drugs or supplements from gastro-intestinal tract by augmenting gastric acidity.

Primary hyperparathyroidism, is a disorder of one or more of the parathyroid glands, resulting from a hyper function of the parathyroid glands themselves (acquired sporadically or familial) resulting in PTH over secretion which could be due to single or double adenoma, hyperplasia, multigland disease or rarely, carcinoma of the parathyroid glands. As a result, the blood calcium rises to a level that is higher than normal (called hypercalcemia). This elevated calcium level can cause many short-term and long-term complications.

Secondary hyperparathyroidism occurs when a decrease in circulating levels of $Ca^{2+}$ level stimulates PTH secretion. One cause of secondary hyperparathyroidism is chronic renal insufficiency (also referred to as chronic kidney disease or CKD), such as that in renal polycystic disease or chronic pyelonephritis, or chronic renal failure, such as that in hemodialysis patients (also referred to as end stage renal disease or ESRD). Excess PTH may be produced in response to hypocalcemia resulting from low calcium intake, GI disorders, renal insufficiency, vitamin D deficiency, magnesium deficiency and renal hypercalciuria. Tertiary hyperparathyroidism may occur after a long period of secondary hyperparathyroidism and hypercalcemia.

In one aspect, the compound and composition of the present invention can be used in treating, managing and/or lessening the vascular or valvular calcification in a subject. In one aspect, administration of the compound of the invention retards or reverses the formation, growth or deposition of extracellular matrix hydroxyapatite crystal deposits. In another aspect of the invention, administration of the compound of the invention prevents the formation, growth or deposition of extracellular matrix hydroxyapatite crystal deposits. In one aspect, the compounds of the invention may also be used to prevent or treat atherosclerotic calcification and medial calcification and other conditions characterized by vascular calcification. In one aspect, vascular calcification may be associated with chronic renal insufficiency or end-stage renal disease or excess calcium or PTH itself. In another aspect, vascular calcification may be associated with pre- or post-dialysis or uremia. In a further aspect, vascular calcification may be associated with diabetes mellitus I or II. In yet another aspect, vascular calcification may be associated with a cardiovascular disorder.

Abnormal calcium homeostasis such as hyperparathyroidism related diseases can be characterized as described in standard medical textbooks, but not limited to Harrison's Principles of Internal Medicine. The compound and composition of the present invention can be used, in particular, to participate in a reduction of the serum levels in the parathyroid hormone known as PTH: these products could thus be useful for the treatment of diseases such as hyperparathyroidism.

Abnormal phosphorous homeostasis such as hypophosphatemia can be characterized as described in standard medical textbooks, but not limited to Harrison's Principles of Internal Medicine. The compound and composition of the present invention can be used, in particular, to participate in a reduction of the serum levels in the parathyroid hormone known as PTH: these products could thus be useful for the treatment of diseases such as hypophosphatemia.

In one aspect, the podocyte diseases or disorders treated by methods of the present invention stem from the perturbations in one or more functions of podocytes. These functions of podocytes include: (i) a size barrier to protein; (ii) charge barrier to protein; (iii) maintenance of the capillary loop shape; (iv) counteracting the intraglomerular pressure; (v) synthesis and maintenance of the glomerular basement membrane (GMB); (vi) production and secretion of vascular endothelial growth factor (VEGF) required for the glomerular endothelial cell (GEN) integrity. Such disorders or diseases include but are not limited to loss of podocytes (podocytopenia), podocyte mutation, an increase in foot process width, or a decrease in slit diaphragm length. In one aspect, the podocyte-related disease or disorder can be effacement or a diminution of podocyte density. In one aspect, the diminution of podocyte density could be due to a decrease in a podocyte number, for example, due to apoptosis, detachment, lack of proliferation, DNA damage or hypertrophy.

In one aspect, the podocyte-related disease or disorder can be due to a podocyte injury. In one aspect, the podocyte injury can be due to mechanical stress such as high blood pressure, hypertension, or ischemia, lack of oxygen supply, a toxic substance, an endocrinologic disorder, an infection, a contrast agent, a mechanical trauma, a cytotoxic agent (cis-platinum, adriamycin, puromycin), calcineurin inhibitors, an inflammation (e.g., due to an infection, a trauma, anoxia, obstruction, or ischemia), radiation, an infection (e.g., bacterial, fungal, or viral), a dysfunction of the immune system (e.g., an autoimmune disease, a systemic disease, or IgA nephropathy), a genetic disorder, a medication (e.g., anti-bacterial agent, anti-viral agent, anti-fungal agent, immunosuppressive agent, anti-inflammatory agent, analgestic or anticancer agent), an organ failure, an organ transplantation, or uropathy. In one aspect, ischemia can be sickle-cell anemia, thrombosis, transplantation, obstruction, shock or blood loss. In one aspect, the genetic disorders may include congenital nephritic syndrome of the Finnish type, the fetal membranous nephropathy or mutations in podocyte-specific proteins.

In one aspect, the compounds of the invention can be used for treating abnormal intestinal motilities disorders such as diarrhea. The methods of the invention comprise administering to the subject a therapeutically effective amount of the compounds of Formula I. In a further aspect, diarrhea can be exudative diarrhea, i.e., resulting from direct damage to the small or large intestinal mucosa. This type of diarrhea can be caused by infectious or inflammatory disorders of the gut. In one aspect, exudative diarrhea can be associated with gastrointestinal or abdominal surgery, chemotherapy, radiation treatment, inflammation or toxic traumatic injury. In another aspect, diarrhea can be secretary, means that there is an increase in the active secretion, or there is an inhibition of absorption. There is little to no structural damage. The most common cause of this type of diarrhea is cholera. In another aspect, diarrhea can be due to acceleration of intestinal transit (rapid transit diarrhea). Such condition may occur because the rapid flow-through impairs the ability of the gut to absorb water.

The compound and composition of the present invention can be used, in particular, to participate in an augmenting gastrin or gastric acid secretion to directly or indirectly benefit certain medical conditions such as but not limited to atrophic gastritis or to improve absorption of pharmacological compounds, drugs or supplements from gastro-intestinal tract by augmenting gastric acidity.

All of the patent, patent application and non-patent publications referred to in this specification are incorporated herein by reference in their entireties.

General Methods of Preparation

The compounds described herein may be prepared by techniques known in the art. In addition, the compounds described herein may be prepared by following the reaction sequence as depicted in Scheme-1 to Scheme-5. Further, in the following schemes, where specific bases, acids, reagents, solvents, coupling agents, etc., are mentioned, it is understood that other bases, acids, reagents, solvents, coupling agents etc., known in the art may also be used and are therefore included within the scope of the present invention. Variations in reaction conditions, for example, temperature and/or duration of the reaction, which may be used as known in the art, are also within the scope of the present invention. All the isomers of the compounds described in these schemes, unless otherwise specified, are also encompassed within the scope of this invention.

Scheme-1a

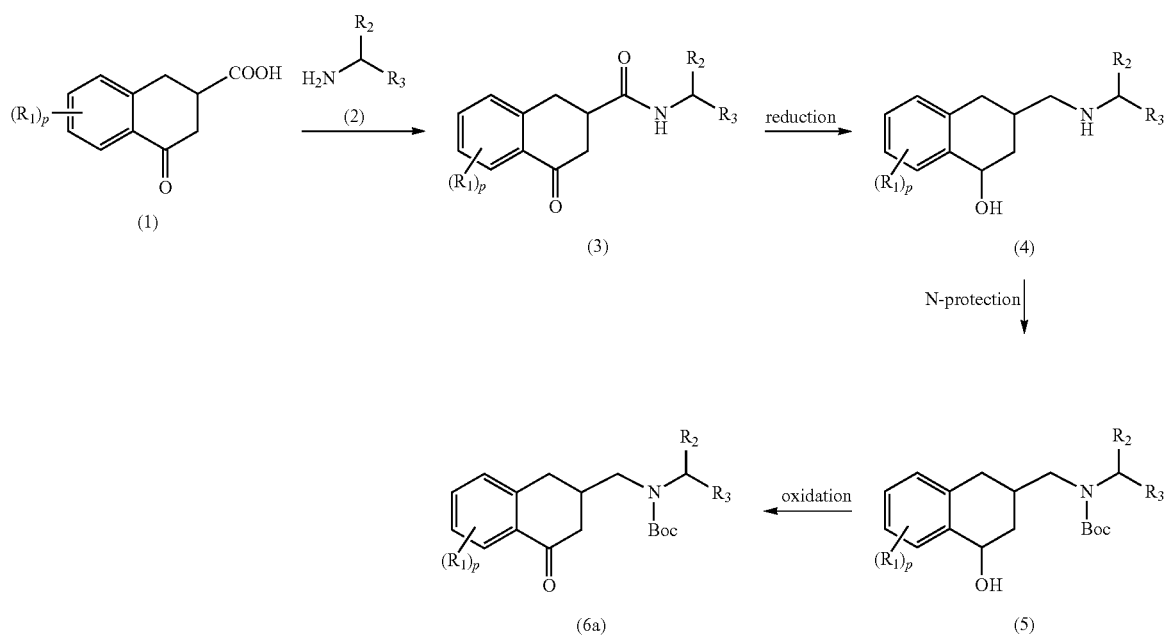

The compound of Formula (6a), Formula (6b) and Formula (6c), where $R_1$, $R_2$, $R_3$ and 'p' are as defined herein above, can be prepared by following the procedure as depicted in Scheme-1a, Scheme-1b and Scheme-1c respectively.

The acid compound of Formula (1) and amine compound of Formula (2) undergoes amide coupling reaction using suitable amide coupling reagents to give compound of Formula (3) (*Tetrahedron: Asymmetry* 14, 2003, 3689; *Journal of Medicinal Chemistry* 25, 1982, 535). This compound of Formula (3) undergoes reduction using suitable reducing agents to give compound of Formula (4) which further undergoes N-Boc protection to give compound of Formula (5). The hydroxy group in Formula (5) is oxidized to give compound of Formula (6a).

Scheme-1b

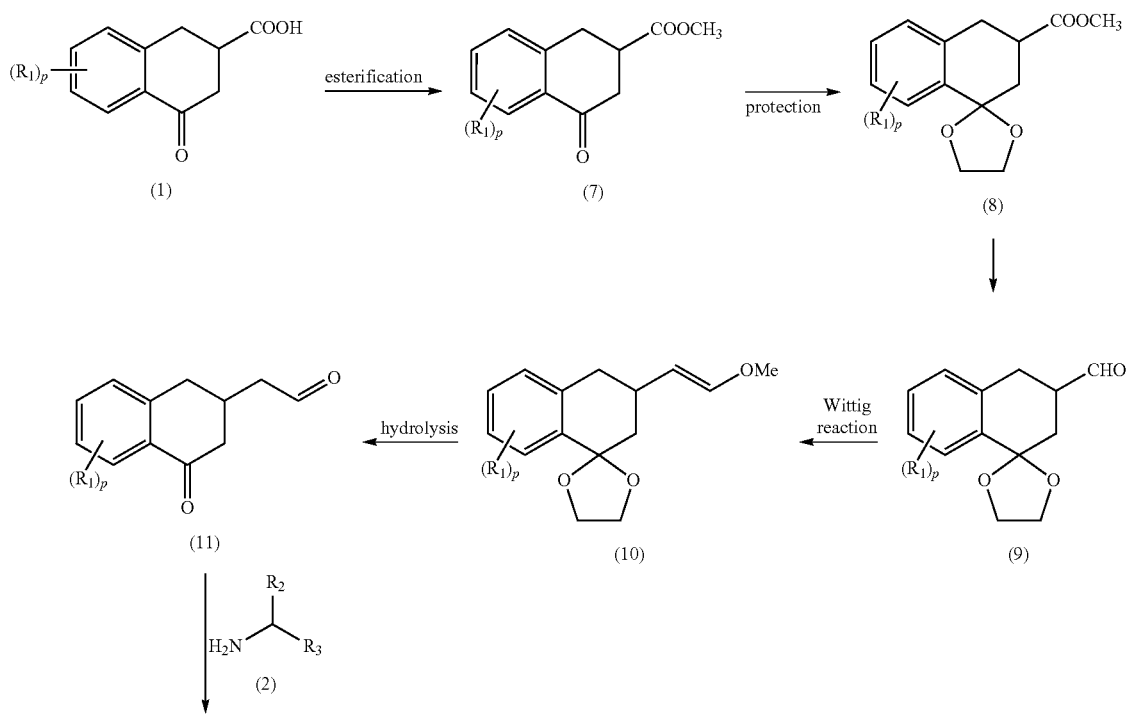

-continued

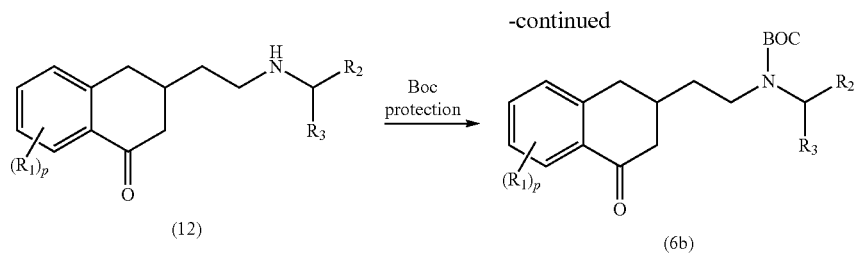

Similarly, the compound of Formula (6b) can be prepared from compound of Formula (1) thus, first the acid group in Formula (1) is converted to corresponding ester of Formula (7) then the keto group in the ring is protected using ethylene glycol to give compound of Formula (8). This ester compound of Formula (8) is converted to aldehyde of Formula (9) which further condensed with appropriate Wittig salt of Chloromethyl methyl ether, ($CH_3OCH_2Cl$) and base like potassium t-butoxide to give compound of Formula (10). This further undergoes acid hydrolysis to give compound of Formula (11). This compound of Formula (11) undergoes reductive amination with compound of Formula (2) using suitable reductive amination reagents to give compound of Formula (12) which further protected as N-Boc to give compound of Formula (6b).

Also, the compound of Formula (6c), can be prepared from the aldehyde compound of Formula (9) which further condensed with appropriate Wittig reagent (ethyl 2-(triphenylphosphoranylidene)acetate) to give compound of Formula (13). The alkenyl ester compound of Formula (13) is first undergoes hydrogenation followed by ester hydrolysis and deprotection to give compound of Formula (14). This acid compound of Formula (14) is coupled with amine of Formula (2) in presence of suitable amide coupling reagents to give compound of Formula (15) after that it is transformed to give compound of Formula (16) by reduction followed by N-protection with $(Boc)_2O$ to give compound of Formula (17), which was further oxidized to give compound of Formula (6c).

Scheme-1c

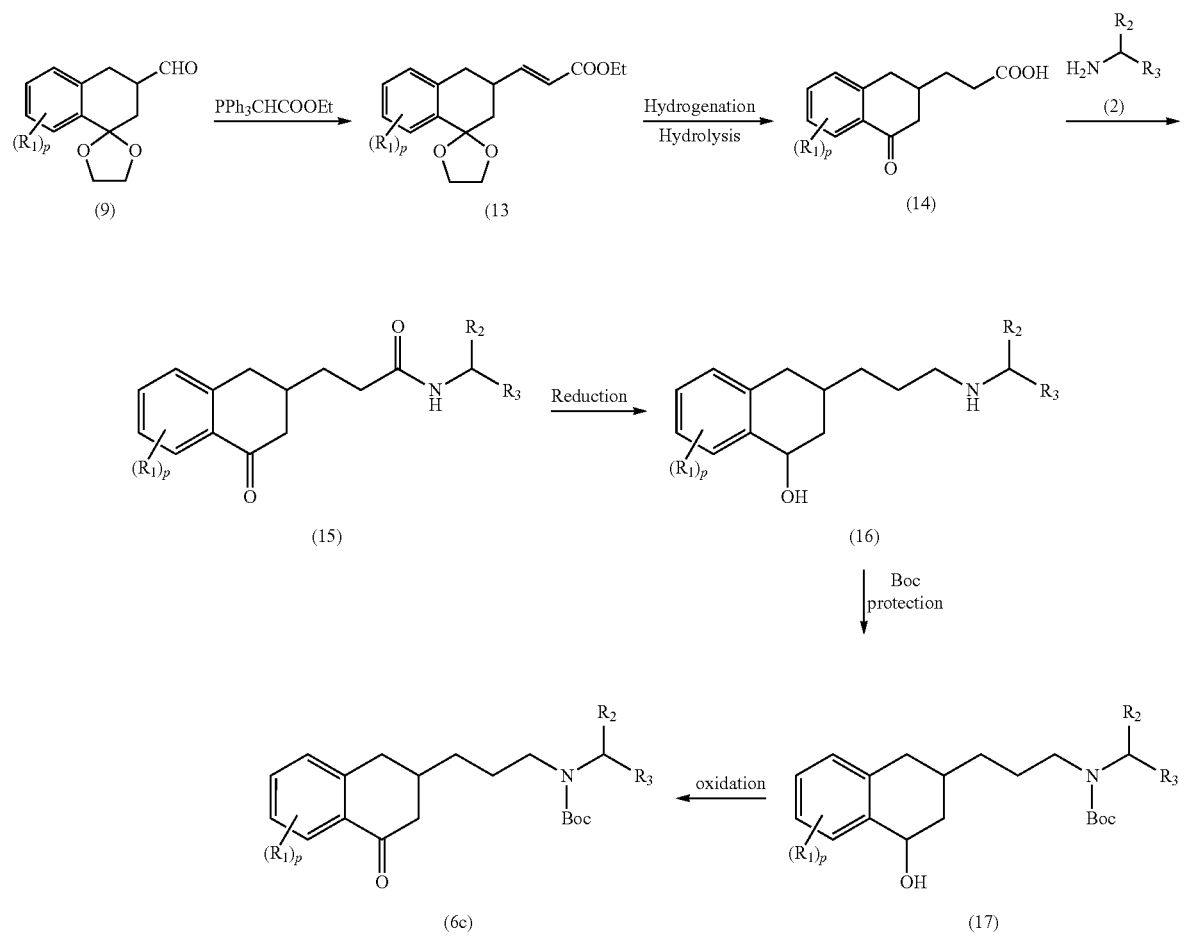

Scheme-2

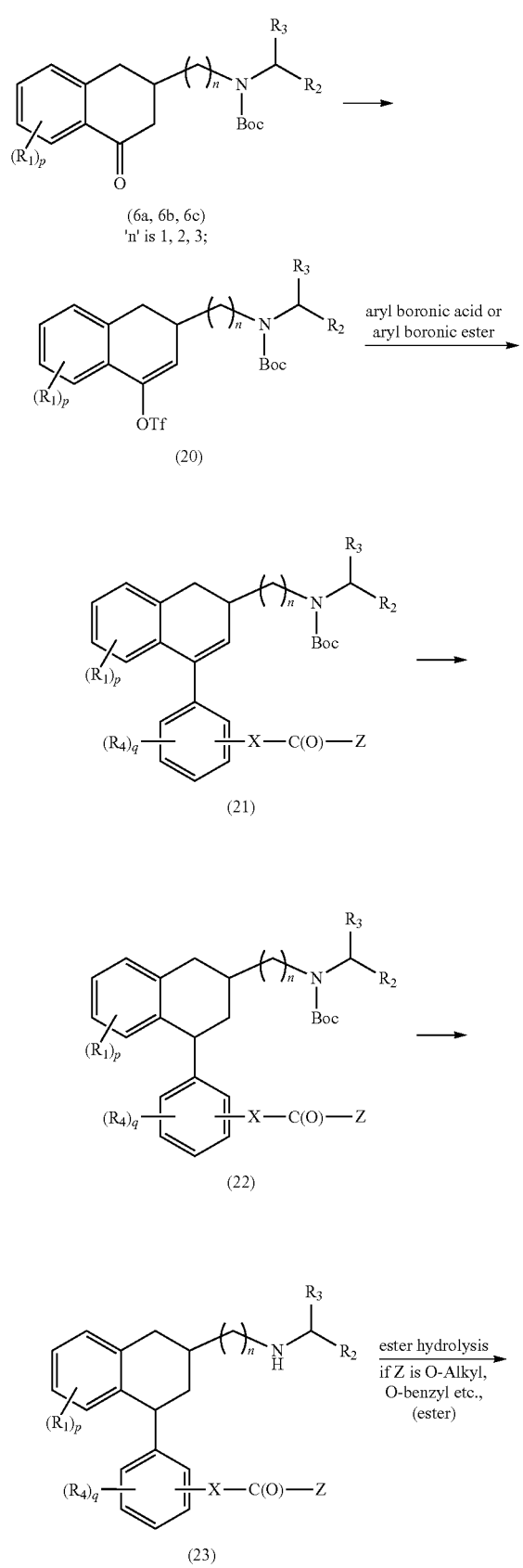

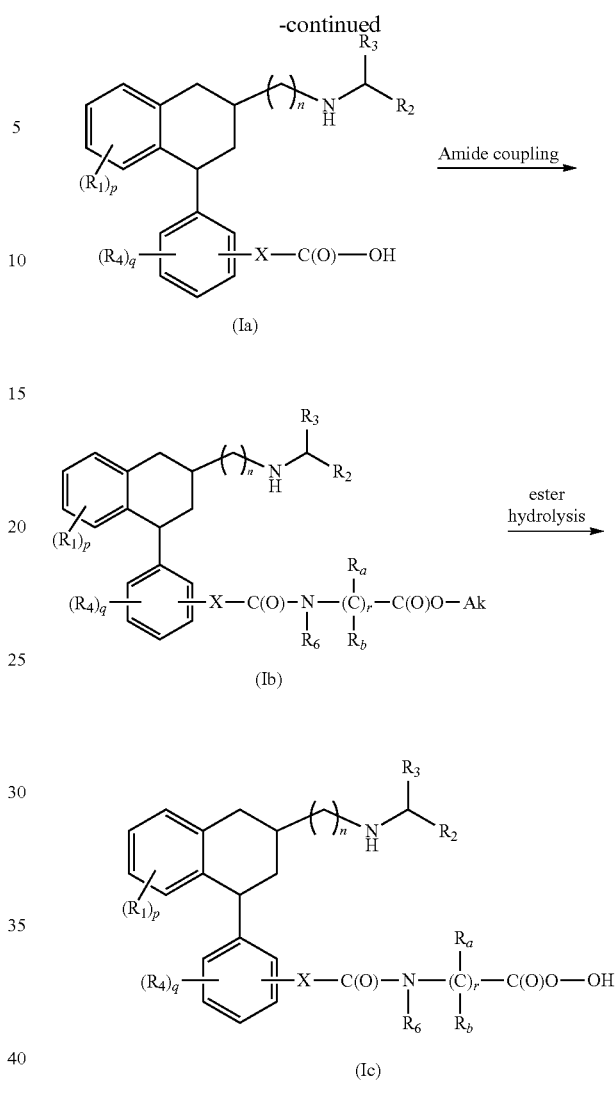

n = 1 to 3;
r = 1 to 3;

The compound of Formula (23), (Ia), (Ib), (Ic) and (Id), where X, Z, $R_1$, $R_2$, $R_3$, $R_4$, $R_6$, $R_a$, $R_b$, 'p' and 'q' are defined herein above can be prepared as depicted in Scheme-2.

The keto group in Formula (6a, 6b, 6c) where 'n' is 1, 2 or 3 respectively, are converted into enol triflate in presence of suitable reaction conditions to give compound of Formula (20). This enol triflate compound of Formula (20) undergoes coupling reaction with suitable aryl boronic acids or aryl boronic ester to give compound of Formula (21). Further, compound of Formula (21) is converted to compound Formula (23) by reduction of double bond followed by N-Boc deprotection reactions. If the compound of Formula (23) is an ester where Z is O-alkyl, O-benzyl etc., it further undergoes ester hydrolysis to give corresponding acid compound of Formula (Ia). The acid compound of Formula (Ia) is converted to corresponding amide in presence of suitable amide coupling reagents to give an amide-ester of Formula (Ib) (where Ak is alkyl) which further undergoes hydrolysis to give acid compound of Formula (Ic). Further hydrochloride salt(s) of compound of Formula (Ia) and Formula (Ic) can be prepared by using hydrochloric acid in suitable solvent.

Scheme-3

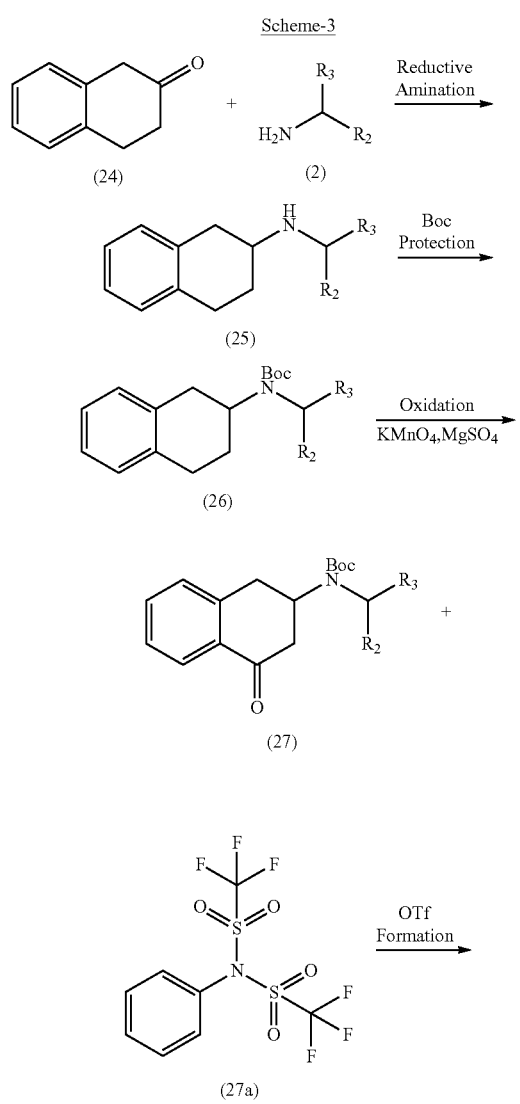

The compound of Formula (Id) and (Ie) where X, Z, $R_1$, $R_2$, $R_3$, $R_4$, 'p' and 'q' are defined herein above is prepared by following the procedure as depicted in Scheme-3. Compound of Formula (24) is reacted with compound of Formula (2) by reductive amination, to obtain compound of Formula (25) which is BOC protected to afford the compound of Formula (26). The compound of Formula (26) is oxidized with suitable oxidizing agent like $KMnO_4$, to get compound of Formula (27) which is treated with reagent of formula (27a) to get the O-triflate derivative of Formula (28). The compound of Formula (28) is reacted with arylboronic acid or aryl boranic ester to give compound of Formula (29). The compound of Formula (29) is hydrogenated with suitable reducing agent to get compound of Formula (30). The compound of Formula (30) is BOC deprotected to get compound of Formula (Id) (if Z is O-alkyl or O-benzyl) it further undergoes hydrolysis to give corresponding acid of Formula (Ie). Further hydrochloride salt(s) of compound of Formula (Ie) can be prepared by using hydrochloric acid in suitable solvent.

Scheme-4a

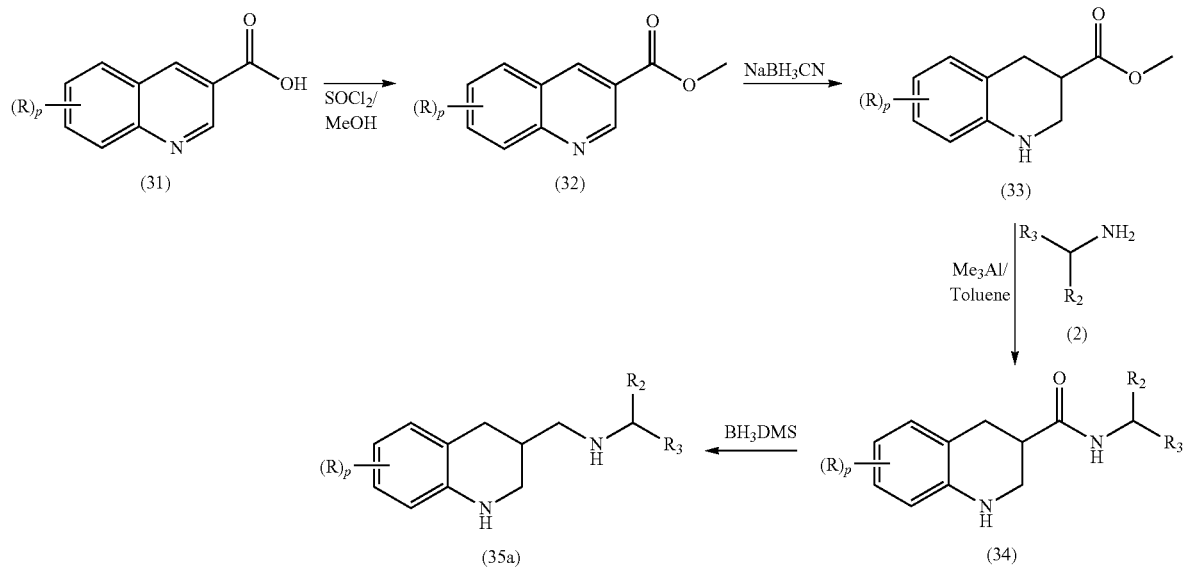

The compound of Formula (35a) is prepared by following the procedure as depicted in Scheme-4a, thus starting from commercially available 3-quinolinecarboxylic acid (31) is reacted with $SOCl_2$ in presence of alcohol to give corresponding ester Formula (32) which undergoes reduction with $NaBH_3CN$ to give compound of Formula (33) (*Tetrahedron: Asymmetry* 2010, vol. 21, 18, 2307-2313). The compound of Formula (33) is reacted with amine of Formula (2) in presence of trimethyl aluminium to obtain compound of Formula (34). This compound of Formula (34) undergoes reduction using suitable reducing agents to give compound of Formula (35a).

Scheme-4b

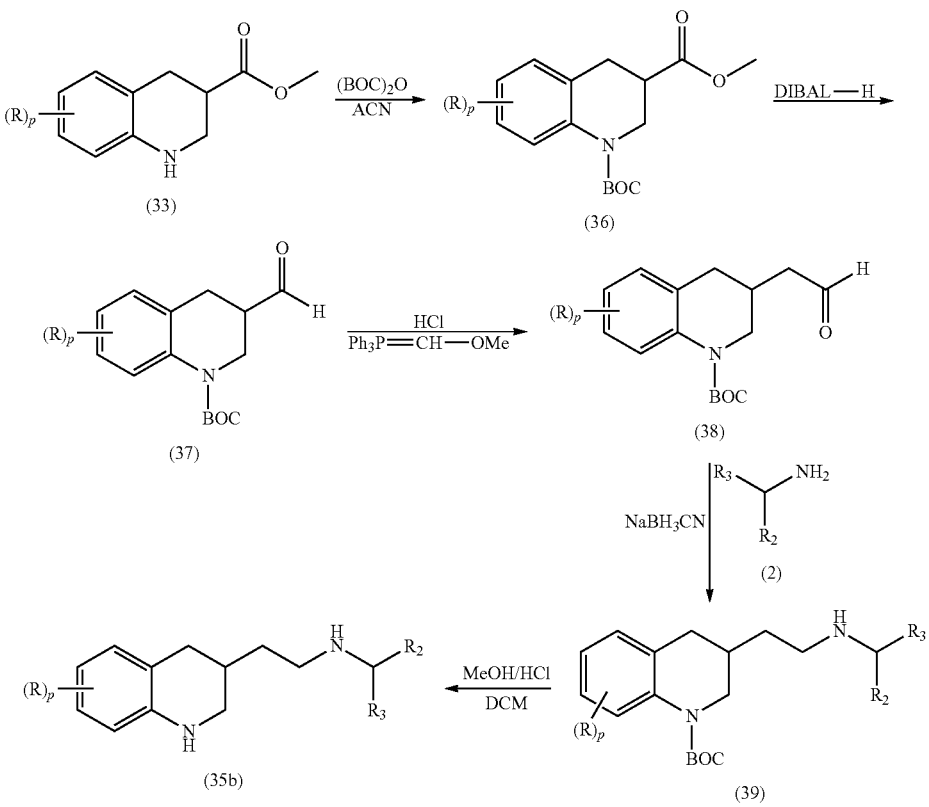

The compound of Formula (35b) is prepared from Formula (33) thus, amine compound of Formula (33) is protected with BOC anhydride in solvent like acetonitrile, DMF, DCM etc. to give corresponding BOC protected Formula (36). Compound of Formula (36) is reduced to give aldehyde of Formula (37). The compound of Formula (37) undergoes Wittig reaction followed by hydrolysis with dilute hydrochloric acid to afford compound of Formula (38). The compound of Formula (38) undergoes reductive amination with amine of Formula (2) to give compound of Formula (39). Compound of Formula (39) is BOC-deprotected with methanolic hydrochloric acid to afford compound of Formula (35b).

Scheme-4c

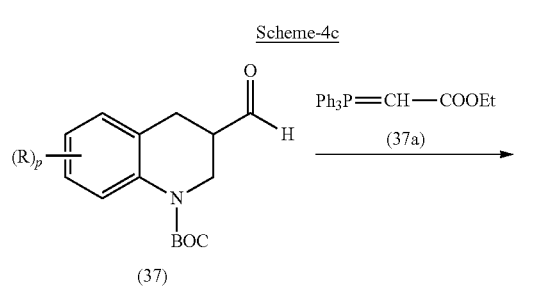

(37)

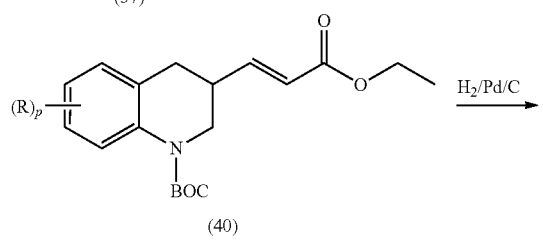

(40)

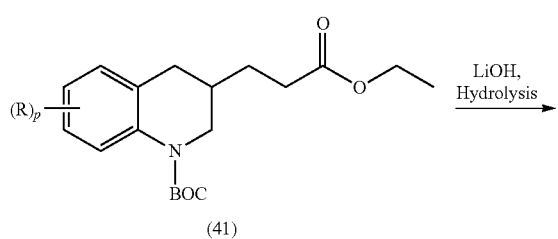

(41)

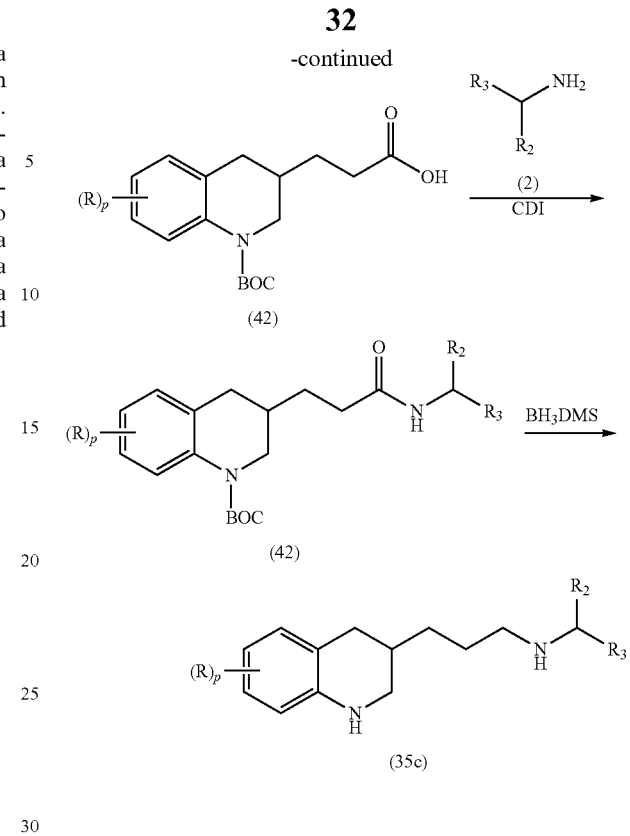

Similarly, the compound of Formula (35c) is prepared from Formula (37) which undergoes Wittig reaction with Formula (37a) to give corresponding alkenes of Formula (40). Compound of Formula (40) is reduced to give ester compound of Formula (41) which further carried-out ester hydrolysis to give acid compound of Formula (42) using suitable base such as NaOH, LiOH, etc. The compound of Formula (42) reacting with amine of Formula (2) using suitable reagents such as CDI to give compound of Formula (43). The compound of Formula (43) undergoes reduction using suitable reducing agents to give compound of Formula (35c).

Scheme-5

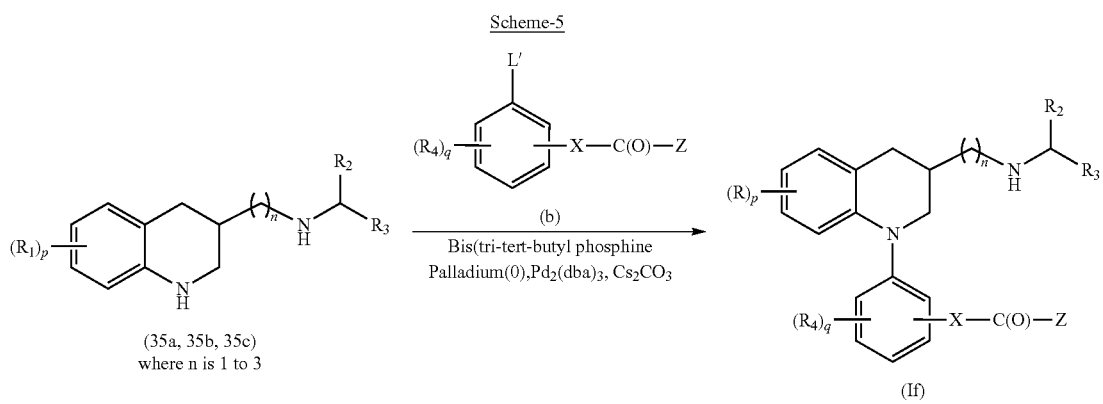

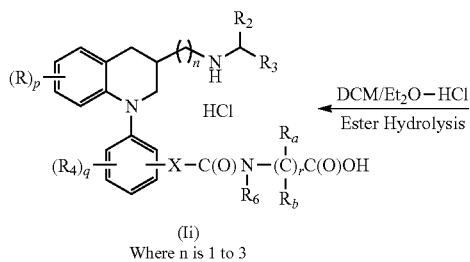 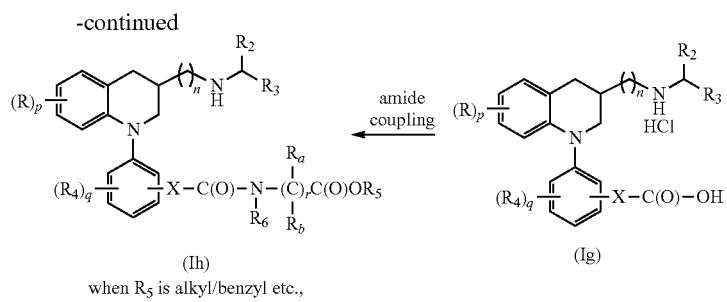

(Ii)
Where n is 1 to 3

(Ih)
when R$_5$ is alkyl/benzyl etc., (Ig)

The compound of Formula (If), (Ig), (Ih) and (Ii), where X, Z, R$_1$, R$_2$, R$_3$, R$_4$, R$_6$, R$_a$, R$_b$, 'p' 'q', and 'r' are defined herein above, can be prepared by following the procedure as depicted in Scheme-5. This compounds of Formula (35a, 35b, 35c) undergoes carbon-nitrogen (C—N) coupling reaction with Formula (b) where L' is leaving group by following the methods known in the art for example Buchwald coupling reaction using suitable reagents known in the art, is carried out by using suitable base for example TEA, DIPEA or K$_2$CO$_3$ etc., and in suitable solvent for example toluene, DME etc., to give compound of Formula (If). If the compound of Formula (If) is an ester where Z is O-alkyl, O-benzyl etc., it further undergoes hydrolysis by using suitable base such as NaOH, LiOH, KOH etc., followed by hydrochloride salt preparation using hydrochloric acid to give corresponding acid of Formula (Ig) which further converted to amide of Formula (Ih) by reacting with suitable amines with suitable amide coupling agents. Further, if these compounds of Formula (Ih) is an esters then it can further hydrolyzed to give corresponding acid compound Formula (Ii) using suitable base such as NaOH, LiOH, KOH etc., followed by hydrochloride salt preparation using hydrochloric acid.

EXPERIMENTAL

The invention is further illustrated by the following examples which are provided merely to be exemplary of the invention and do not limit the scope of the invention. The examples set forth below demonstrate the synthetic procedures for the preparation of the representative compounds. Certain modifications and equivalents will be apparent to those skilled in the art and are intended to be included within the scope of the invention. Unless otherwise stated, work-up implies the following operations: distribution of the reaction mixture between the organic and aqueous phase, separation of layers, drying the organic layer over sodium sulfate, filtration and evaporation of the organic solvent. Purification, unless otherwise mentioned, implies purification by silica gel chromatographic techniques, generally using ethyl acetate/petroleum ether mixture of a suitable polarity as the mobile phase.

Intermediates
Intermediate-1

3-(((tert-Butoxycarbonyl)((R)-1-(naphthalen-1-yl)ethyl)amino)methyl)-3,4-dihydro naphthalen-1-yl trifluoromethanesulfonate

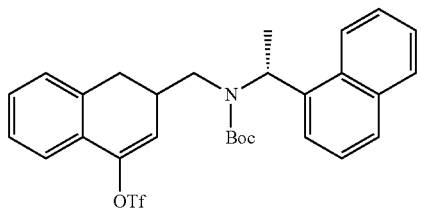 [SMILES: C[C@H](c1cccc2ccccc12)N(CC1C=C(OS(=O)(=O)C(F)(F)F)c2ccccc2C1)C(=O)OC(C)(C)C]

Step-1: N—((R)-1-(Naphthalen-1-yl)ethyl)-4-oxo-1,2,3,4-tetrahydronaphthalene-2-carboxamide To a mixture of 4-oxo-1,2,3,4-tetrahydronaphthalene-2-carboxylic acid (4.6 g, 24.19 mmol) (*Tetrahedron: Asymmetry* 14, 2003, 3689; *Journal of Medicinal Chemistry* 25, 1982, 535), in DMF (20 mL), CDI (3.92 g, 24.19 mmol) was added. The reaction mixture was stirred at room temperature (RT) for 2 h. Then (R)-1-(naphthalen-1-yl)ethanamine (5.40 g, 31.5 mmol) was added and the reaction mixture was stirred at RT overnight. After completion of reaction, ice was added to the reaction mixture, solid precipitated out was filtered on Buchner funnel, washed with DM water (50 mL) and dried to get crude compound. Compound was further purified by flash chromatography (biotage) using eluent 15% ethyl acetate:hexane to yield the title compound (8 g, 96%); m/z 344.

Step-2: 3-((((R)-1-(Naphthalen-1-yl)ethyl)amino)methyl)-1,2,3,4-tetrahydro naphthalen-1-ol Step-1 intermediate (300 mg, 0.874 mmol) was added to a suspension of LAH (166 mg, 4.37 mmol) in dioxane (10 mL) at 0° C. The reaction mixture was stirred for 30 minutes at 25° C. then heated to 100° C. and further maintained for 12 h. The mixture was allowed to RT, further cooled to 0° C. and slowly quenched with ethyl acetate (2 mL) followed by water (2 mL). Reaction mixture was extracted with ethyl acetate (30 mL), washed with brine solution (20 mL) and dried over Na$_2$SO$_4$ and concentrated to get crude compound which was used as it is in next reaction; m/z 332.1.

Step-3: tert-Butyl ((4-hydroxy-1,2,3,4-tetrahydronaphthalen-2-yl)methyl)((R)-1-(naphthalen-1-yl)ethyl)carbamate To a mixture of Step-2 intermediate (290 mg, 0.875 mmol) and triethylamine (TEA) (0.305 mL, 2.187 mmol) in acetonitrile (10 mL), Boc$_2$O (0.244 mL, 1.050 mmol) was added at 25° C. The reaction mixture was heated to 55° C. and further maintained for 12 h. To this reaction mixture, water was added (15 mL) and extracted with ethyl acetate (2×15 mL). The organic phase was washed with brine solution (10 mL), dried over Na$_2$SO$_4$ and filtered. The clear organic phase was evaporated in vacuo to get crude compound. This crude compound was used as it is in next reaction. m/z 431.79.

Step-4: tert-Butyl((R)-1-(naphthalen-1-yl)ethyl)((4-oxo-1,2,3,4-tetrahydro naphthalen-2-yl)methyl)carbamate To a stirred solution of Step-3 intermediate (270 mg, 0.626 mmol) dichloromethane (DCM) (20 mL), pyridinium chlorochromate (142 mg, 0.657 mmol) was added and stirred for 1 h at 25° C. The reaction mixture was filtered through celite bed and concentrated to get crude compound. This crude compound was purified by column chromatography (Biotage) using eluent (1:9, ethyl acetate:n-hexane) to get the title compound (210 mg). m/z 430.48.

Step-5: 3-(((tert-Butoxycarbonyl)((R)-1-(naphthalen-1-yl)ethyl)amino)methyl)-3,4-dihydronaphthalen-1-yl trifluoromethanesulfonate Solid Potassium bis(trimethylsilyl)amide (KHMDS) (121 mg, 0.605 mmol) is added to a solution of step-4 intermediate (200 mg, 0.466 mmol) in tetrahydrofuran (THF) (10 ml) at −78° C. Reaction mixture was stirred for 30 minutes and solid 1,1,1-trifluoro-N-phenyl-N-((trifluoromethyl)sulfonyl) methanesulfonamide (233 mg, 0.652 mmol) was added at −78° C. under nitrogen atmosphere and further stirred for 2 h at −78° C. Then the reaction mixture was quenched with water (5 mL), extracted with diethylether (2×25 mL), dried over Na$_2$SO$_4$ and concentrated to get crude compound. This crude compound was further purified by flash chromatography (Biotage) using eluent hexane/Ethyl acetate 90:10 to get the title compound (210 mg, 80%); m/z-Boc 461.9

Intermediate-2

(R)-3-(((tert-Butoxycarbonyl)((R)-1-(naphthalen-1-yl)ethyl)amino)methyl)-3,4-dihydronaphthalen-1-yl trifluoromethanesulfonate

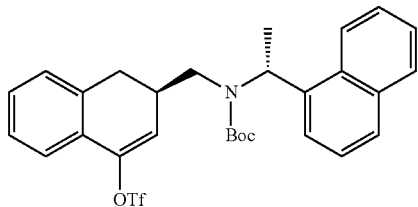 [SMILES: C[C@H](c1cccc2ccccc12)N(C[C@H]1C=C(OS(=O)(=O)C(F)(F)F)c2ccccc2C1)C(=O)OC(C)(C)C]

The title compound was prepared by following the similar procedure as described in Step-1 to Step-5 of Intermediate-1 by using (R)-4-oxo-1,2,3,4-tetrahydronaphthalene-2-carboxylic acid and (R)-1-(naphthalen-1-yl)ethanamine.

Intermediate-3

(R)-3-(((tert-Butoxycarbonyl)((R)-1-(4-fluoro-3-ethoxyphenyl)ethyl)amino)methyl)-3,4-dihydronaphthalen-1-yl trifluoromethanesulfonate

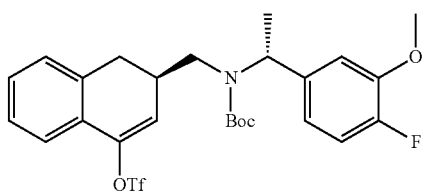 [SMILES: COc1cc([C@@H](C)N(C[C@H]2C=C(OS(=O)(=O)C(F)(F)F)c3ccccc3C2)C(=O)OC(C)(C)C)ccc1F]

The title compound was prepared by following the similar procedure as described in Step-1 to Step-5 of Intermediate-1 by using (R)-4-oxo-1,2,3,4-tetrahydronaphthalene-2-carboxylic acid and (R)-1-(4-fluoro-3-methoxyphenyl)ethanamine; m/z-Boc 460.7.

Intermediate-4

(R)-3-(((tert-Butoxycarbonyl)((R)-1-(4-fluoronaphthalen-1-yl)ethyl)amino)methyl)-3,4-dihydronaphthalen-1-yl trifluoromethanesulfonate

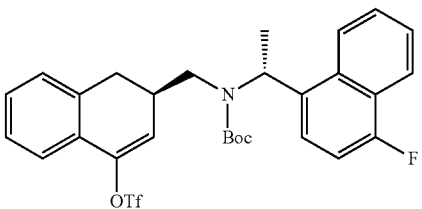 [SMILES: C[C@H](c1ccc(F)c2ccccc12)N(C[C@H]1C=C(OS(=O)(=O)C(F)(F)F)c2ccccc2C1)C(=O)OC(C)(C)C]

The title compound was prepared by following the similar procedure as described in Step-1 to Step-5 of Intermediate-1 by using (R)-4-oxo-1,2,3,4-tetrahydronaphthalene-2-carboxylic acid and (R)-1-(4-Fluoronaphthalen-1-yl)ethanamine; m/z-Boc 480.93.

Intermediate-5

3-((tert-Butoxycarbonyl)((R)-1-(naphthalen-1-yl)ethyl)amino)-3,4-dihydro naphthalen-1-yl-trifluoromethanesulfonate

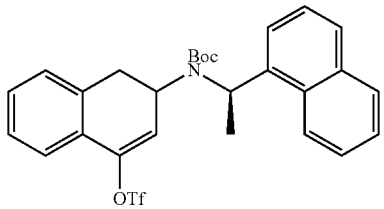 [SMILES: C[C@H](c1cccc2ccccc12)N(C(=O)OC(C)(C)C)C1C=C(OS(=O)(=O)C(F)(F)F)c2ccccc2C1]

Step-1: N—((R)-1-(Naphthalen-1-yl)ethyl)-1,2,3,4-tetrahydronaphthalen-2-amine

To a stirred solution of (R)-1-(naphthalen-1-yl)ethanamine (4.77 ml, 29.5 mmol) in methanol (50 mL) was added 3,4-dihydronaphthalen-2(1H)-one (4.80 g, 32.8 mmol) at 0° C. Acetic acid (2.349 mL, 41.0 mmol) was added and the reaction was stirred for 5 min. After that the reaction was warmed to RT and further stirred for 20 minutes. Again reaction was cooled to 0° C. and sodium cyanoborohydride (3.09 g, 49.2 mmol) was added stirred overnight at RT. After completion of reaction, —NaHCO$_3$ solution (20 mL) and water (50 mL) were added and the mixture was extracted with ethyl acetate (50 mL×2). The extract was washed with saturated brine, dried over anhydrous Na$_2$SO$_4$ and evaporated under reduced pressure to get the crude compound. This was used directly in the next reaction (11.1 g, 36.8 mmol); m/z 302.65.

Step-2: tert-Butyl((R)-1-(naphthalen-1-yl)ethyl)(1,2, 3,4-tetrahydronaphthalen-2-yl)carbamate To a stirred solution of Step-1 intermediate (11.1 g, 36.8 mmol) in DCM (40 mL) was added triphosgene (8.12 g, 27.4 mmol) at 0° C. The reaction was allowed to RT and stirred for 2 h. Reaction mixture was then diluted with DCM (100 mL) and washed with water (100 mL), dried over sodium sulphate and concentrated to get crude compound. To this crude, triethylamine (20.35 ml, 146 mmol), DIPEA (0.496 ml, 2.85 mmol) t-butanol (34.8 ml, 365 mmol) were added, heated to reflux and further maintained for 6 hours. The mixture was allowed to RT, t-Butanol was evaporated, reaction mixture was diluted with water (25 mL) and the resulting mixture was extracted with ethyl acetate (25 mL). The organic extract was washed with saturated brine solution (10 mL). The organic phase was dried (Na$_2$SO$_4$), filtered and the solvent evaporated in vacuo to get 15 g of crude compound. This crude compound was further purified by flash chromatography (biotage) using eluent 20% ethyl acetate in hexane to get the title compound (4.2 g, 28.7% yield); m/z 402.0.

Step-3: tert-Butyl((R)-1-(naphthalen-1-yl)ethyl)(4-oxo-1,2,3,4-tetrahydro naphthalen-2-yl)carbamate To a mixture of Step-2 intermediate (4.2 g, 10.46 mmol) in acetone (40 mL) and water (20. mL), MgSO$_4$ (3.02 g, 25.1 mmol) was added at RT. The reaction mixture was cooled to 0° C. To this cooled solution, KMnO$_4$ (3.31 g, 20.92 mmol) was added in portions wise while maintaining at 0° C. The reaction was then warmed to RT and stirred overnight. The crude was filtered through Buckner funnel with a filter paper. The solid residue was washed repeatedly with dichloromethane (3 times) and the collective organic layer was combined and evaporated. The residue was then dissolved in ethyl acetate, and was treated with saturated sodium sulphite solution. The organic layer was separated and washed with saturated brine solution, dried over Na$_2$SO$_4$ and concentrated to get 5.4 g of crude compound. This crude compound was purified by flash chromatography (Biotage) using eluent 7% ethyl acetate:hexane to get the title compound (1 g, 23.01% yield); m/z 315.7.

Step-4: 3-((tert-Butoxycarbonyl)((R)-1-(naphthalen-1-yl)ethyl)amino)-3,4-dihydro naphthalen-1-yl trifluoromethanesulfonate Solid KHMDS (0.624 g, 3.13 mmol) was added to a solution of Step-3 intermediate (1.0 g, 2.407 mmol) in tetrahydrofuran (20 mL) at −78° C. Reaction mixture was stirred for 30 min and solid 1,1,1-trifluoro-N-phenyl-N-((trifluoromethyl)sulfonyl)methanesulfonamide (1.204 g, 3.37 mmol) was added at −78° C. under nitrogen atmosphere and stirred for 2 h at the same temperature. After that the reaction mixture was quenched with H$_2$O, extracted with diethyl ether, dried over Na$_2$SO$_4$ and concentrated to get crude compound. This crude compound was purified by flash chromatography (Biotage) using eluent hexane/ethyl acetate 95:5 to get the title compound (500 mg, 37.9% yield).

Intermediate-6

(S)-3-(2-((tert-Butoxycarbonyl)((R)-1-(4-fluoronaphthalen-1-yl)ethyl)amino)ethyl)-3,4-dihydronaphthalen-1-yl trifluoromethanesulfonate

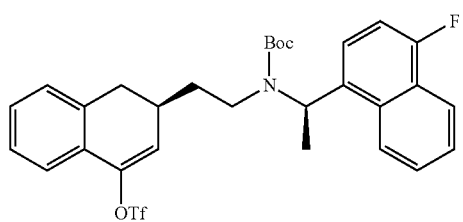 [SMILES: C[C@H](c1ccc(F)c2ccccc12)N(CC[C@H]1C=C(OS(=O)(=O)C(F)(F)F)c2ccccc2C1)C(=O)OC(C)(C)C]

Step-1: (R)-Methyl 4-oxo-1,2,3,4-tetrahydronaphthalene-2-carboxylate

To the stirred solution of (R)-4-oxo-1,2,3,4-tetrahydronaphthalene-2-carboxylic acid (5.0 g, 26.3 mmol), K$_2$CO$_3$ (10.90 g, 79 mmol) and methyl iodide (6.58 ml, 105 mmol) was added in DMF (50 mL) and stirred for overnight at 25° C. Water was added (130 mL) and extracted with ethyl acetate (2×30 mL). The organic phase was washed with aq. Sodium bicarbonate solution (2×20 mL), dried over Na$_2$SO$_4$ and filtered. The clear organic phase was evaporated in vacuo to get title compound (4.5 g) m/z 204.09.

Step-2: (R)-Methyl 3',4'-dihydro-2'H-spiro[[1,3]dioxolane-2,1'-naphthalene]-3'-carboxylate To a stirred solution of (R)-methyl 4-oxo-1,2,3,4-tetrahydronaphthalene-2-carboxylate (4.5 g, 22.03 mmol) in benzene (40 mL), ethane-1,2-diol (3.69 mL, 66.1 mmol) and a catalytic amount of p-toluenesulfonic acid was added. The reaction mixture was heated to reflux temperature and further maintained for 20 hours. Then, reaction mixture was allowed to RT, concentrated under vacuum to yield 12 g of crude compound. This crude material was purified by flash chromatography (Biotage) using 7% ethyl acetate in hexane to give title compound (4.7 g) m/z 248.6.

Step-3: (R)-3',4'-Dihydro-2'H-spiro[[1,3]dioxolane-2,1'-naphthalene]-3'-carbaldehyde To a stirred solution of (R)-methyl 3',4'-dihydro-2'H-spiro[[1,3]dioxolane-2,1'-naphthalene]-3'-carboxylate (4.7 g, 18.93 mmol) in toluene (50 mL) and CH$_2$Cl$_2$ (12.50 mL) to these solution of DIBAL-H (Diisobutylaluminum hydride) (22.72 mL, 22.72 mmol) was added drop-wise at −78° C. under argon, and the mixture was stirred for 2 h at this temperature.

Reaction mixture was quenched with aqueous NH$_4$Cl solution at −78° C. and allowed to RT, filtered through celite, diluted with water (25 mL) and extracted with DCM (2×25 mL), dried over Na$_2$SO$_4$, filtered and concentrated to get the title compound (4.1 g) as an oily mass.

Step-4: (R)-3'-(2-Methoxyvinyl)-3',4'-dihydro-2'H-spiro[[1,3]dioxolane-2,1'-naphthalene]

To a stirred solution of (methoxymethylene)triphenylphosphorane (6.74 g, 21.99 mmol) in tetrahydrofuran (30 mL) was added drop-wise a solution of potassium tert-butoxide (3.08 g, 27.5 mmol) in THF at −30° C. under argon, and the mixture was stirred for 30 min. Then a solution of (R)-3',4'-dihydro-2'H-spiro[[1,3]dioxolane-2,1'-naphthalene]-3'-carbaldehyde (4.0 g, 18.33 mmol) in THF was added drop-wise and reaction was stirred for 1 h at −30° C. Reaction was monitored by TLC. Reaction mixture quenched with water at −30° C. and allowed to RT, diluted with water (25 mL) and extracted with ethyl acetate (2×50 mL), dried over Na₂SO₄, filtered and concentrated to give crude product (8 g). The crude compound was purified with silica gel flash column chromatography (Biotage) to give (R)-3'-(2-methoxyvinyl)-3',4'-dihydro-2'H-spiro[[1,3]dioxolane-2,1'-naphthalene] (3.5 g, 14.21 mmol, 78% yield) as colourless liquid; m/z 246.6.

Step-5: (S)-2-(4-Oxo-1,2,3,4-tetrahydronaphthalen-2-yl)acetaldehyde

To a stirred solution of (R)-3'-(2-methoxyvinyl)-3',4'-dihydro-2'H-spiro[[1,3]dioxolane-2,1'-naphthalene] (step-4) (3.5 g, 14.21 mmol) in tetrahydrofuran (20 mL) was added HCl (2.159 mL, 71.1 mmol) at 25° C. and reaction was stirred for 16 h. Reaction was monitored by TLC. After completion solvent was evaporated at reduced pressure. Crude obtained was purified by column chromatography (Biotage) using eluent 30% ethyl acetate/hexane to give (S)-2-(4-oxo-1,2,3,4-tetrahydronaphthalen-2-yl)acetaldehyde (1.8 g, 9.56 mmol, 67.3% yield) as colourless sticky compound; GCMS 188.10.

Step-6: (S)-3-(2-(((R)-1-(4-Fluoronaphthalen-1-yl)ethyl)amino)ethyl)-3,4-dihydronaphthalen-1(2H)-one To a stirred solution of (R)-1-(4-fluoronaphthalen-1-yl) ethanamine (1.206 g, 6.38 mmol) in methanol (5 mL) was added (S)-2-(4-oxo-1,2,3,4-tetrahydronaphthalen-2-yl)acetaldehyde (1.2 g, 6.38 mmol) at 0° C. Acetic acid (0.365 mL, 6.38 mmol) was added and reaction was stirred for 5 min. Reaction was warmed to RT and stirred for 20 min. Again reaction was cooled to 0° C. Sodium cyanoborohydride (0.401 g, 6.38 mmol) was added to the reaction mixture and stirred for overnight (16 h). To the reaction solution were added NaHCO₃ solution (5 mL) and water (10 mL) and the mixture was extracted with ethyl acetate (20 mL×2). The extract was washed with saturated brine solution, dried over anhydrous Na₂SO₄ and evaporated under reduced pressure to get crude title compound (2.0 g, 5.53 mmol, 87% yield).

Step-7: tert-Butyl((R)-1-(4-fluoronaphthalen-1-yl)ethyl)(2-((S)-4-oxo-1,2,3,4-tetrahydronaphthalen-2-yl)ethyl)carbamate To a mixture of step-6 intermediate (2 g, 5.53 mmol) and triethylamine (0.727 mL, 5.53 mmol) in acetonitrile (20 mL), Boc-anhydride (2.54 mL, 11.07 mmol) was added at 25° C. to the reaction mixture. The reaction was stirred for overnight 15 hrs. To the reaction mixture was added water (20 mL) and the resulting mixture was extracted with ethyl acetate (50 mL). The organic extract was washed with saturated brine solution (30 mL). The organic phase was dried with Na₂SO₄, filtered and the solvent evaporated in vacuo to get crude compound. Compound was purified on flash chromatography (biotage) using eluent 10% ethyl acetate in hexane to give title compound (1.9 g, 74.4% yield) as sticky compound; m/z-Boc 362.1.

Step-8: (S)-3-(2-((tert-Butoxycarbonyl)((R)-1-(4-fluoronaphthalen-1-yl)ethyl)amino)ethyl)-3,4-dihydronaphthalen-1-yl trifluoromethanesulfonate KHMDS (5.88 ml, 5.35 mmol) was added to a solution of step-7, intermediate (1.9 g, 4.12 mmol) in tetrahydrofuran (30 mL) at −78° C. Reaction mixture was stirred for 60 min and solution of 1,1,1-trifluoro-N-phenyl-N-((trifluoromethyl)sulfonyl)methanesulfonamide (2.059 g, 5.76 mmol) in THF was added at −78° C. under nitrogen and stirred for 3 h at −78° C. Reaction was monitored by TLC. It was quenched with H₂O, extracted with diethyl ether and dried with Na₂SO₄ and concentrated. Compound was purified by flash chromatography (Biotage) using eluent hexane/ethyl acetate 90:10 to give title compound (1.2 g, 49.1% yield); m/z 615.7 (M+Na).

Intermediate-7

(S)-3-(2-((tert-Butoxycarbonyl)((R)-1-(naphthalen-1-yl)ethyl)amino)ethyl)-3,4-dihydro naphthalen-1-yl trifluoromethanesulfonate

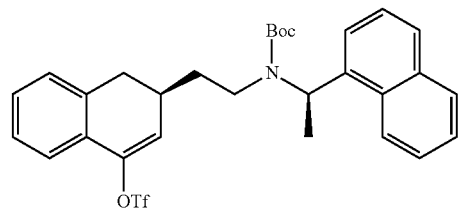 [SMILES: C[C@H](c1cccc2ccccc12)N(CC[C@H]1C=C(OS(=O)(=O)C(F)(F)F)c2ccccc2C1)C(=O)OC(C)(C)C]

The title compound was prepared by following the similar procedures as described in Step-1 to Step-8 of Intermediate-6 by using (S)-2-(4-oxo-1,2,3,4-tetrahydronaphthalen-2-yl)acetaldehyde and (R)-1-(naphthalen-1-yl)ethanamine.

Intermediate-8

(R)-3-(3-((tert-Butoxycarbonyl)((R)-1-(4-fluoronaphthalen-1-yl)ethyl)amino)propyl)-3,4-dihydronaphthalen-1-yl trifluoromethanesulfonate

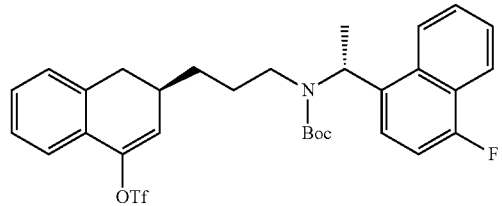 [SMILES: C[C@H](c1ccc(F)c2ccccc12)N(CCC[C@H]1C=C(OS(=O)(=O)C(F)(F)F)c2ccccc2C1)C(=O)OC(C)(C)C]

Step-1: (R)-Methyl 4-oxo-1,2,3,4-tetrahydronaphthalene-2-carboxylate

To the stirred solution of (R)-4-oxo-1,2,3,4-tetrahydronaphthalene-2-carboxylic acid (5.0 g, 26.3 mmol), K₂CO₃ (10.90 g, 79 mmol) and methyl iodide (6.58 mL, 105 mmol) was added in DMF (50 mL) and stirred for overnight at 25° C. Water was added (130 mL) and extracted with ethyl acetate (2×30 mL). The organic phase was washed with aq. Sodium bicarbonate solution (2×20 mL), dried over Na₂SO₄ and filtered. The clear organic phase was evaporated in vacuo to get pure title compound (4.5 g) m/z 204.09.

Step-2: (R)-Methyl 3',4'-dihydro-2'H-spiro[[1,3]dioxolane-2,1'-naphthalene]-3'-carboxylate To the stirred solution of (R)-methyl 4-oxo-1,2,3,4-tetrahydronaphthalene-2-carboxylate (4.5 g, 22.03 mmol) in benzene (40 mL), ethane-1,2-diol (3.69 mL, 66.1 mmol) and a catalytic amount of p-toluenesulfonic acid was added. The reaction mixture was heated to reflux temperature and further maintained for 20 hours. After 20 hours, the reaction mixture was allowed to RT, concentrated under vacuum to yield 12 g of crude compound. Crude material was purified by flash chromatography (Biotage) using 7% ethyl acetate:hexane get title compound (4.7 g) m/z 248.6.

Step-3: (R)-3',4'-Dihydro-2'H-spiro[[1,3]dioxolane-2,1'-naphthalene]-3'-carbaldehyde To a stirred solution of (R)-methyl 3',4'-dihydro-2'H-spiro[[1,3]dioxolane-2,1'-naphthalene]-3'-carboxylate (4.7 g, 18.93 mmol) in toluene (50 mL) and DCM (12.50 mL) to these solution of DIBAL-H (22.72 mL, 22.72 mmol) was added drop-wise at −78° C. under argon, and the mixture was stirred for 2 h at this temperature. Reaction mixture was quenched with aqueous $NH_4Cl$ solution at −78° C. and allowed to RT, filtered through celite, diluted with water (25 mL) and extracted with DCM (2×25 mL), dried over $Na_2SO_4$, filtered and concentrated to get the title compound (4.1 g) as an oil.

Step-4: (R)-Ethyl 3-(3',4'-dihydro-2'H-spiro[[1,3]dioxolane-2,1'-naphthalen]-3'-yl)acrylate To the stirred solution of (R)-3',4'-dihydro-2'H-spiro[[1,3] dioxolane-2,1'-naphthalene]-3'-carbaldehyde (4.1 g, 18.79 mmol) in DCM (10 mL), ethyl 2-(triphenyl phosphoranylidene)acetate (7.85 g, 22.54 mmol) was added and reaction mixture was stirred at RT for 16 h. After completion of reaction, reaction mixture was concentrated under vacuum to get 5.5 g of crude compound. This crude compound was further purified by flash chromatography (Biotage) using eluent hexane/ethyl acetate 80:20 to get the title compound (2.5 g, 46.2% yield); m/z 288.34

Step-5: (R)-Ethyl 3-(3',4'-dihydro-2'H-spiro[[1,3]dioxolane-2,1'-naphthalen]-3'-yl)propanoate To a stirred solution of Pd/C (0.535 g, 0.251 mmol) in ethyl acetate (25 mL), (R)-ethyl 3-(3',4'-dihydro-2'H-spiro[[1,3] dioxolane-2,1'-naphthalen]-3'-yl)acrylate (2.5 g, 8.67 mmol) was added under nitrogen. Reaction mixture was stirred for 2 h under hydrogen balloon. After completion of reaction, reaction mixture was filtered through celite, concentrated to get the crude compound. This crude compound was used directly in next reaction (2.3 g, 91%); m/z 290.7

Step-6: (R)-3-(4-Oxo-1,2,3,4-tetrahydronaphthalen-2-yl)propanoic acid

To a stirred solution of (R)-ethyl 3-(3',4'-dihydro-2'H-spiro [[1,3]dioxolane-2,1'-naphthalen]-3'-yl)propanoate (2.3 g, 7.92 mmol) in THF (10 mL) and water (1 mL) in round bottom flask. LiOH (1.328 g, 55.4 mmol) was added and reaction mixture was stirred at 25° C. for 2 h. Reaction mixture was concentrated and acidified with dilute HCl, stirred for 1 h at RT. Extracted with ethyl acetate (2×30 mL), dried over sodium sulphate, concentrated to get crude title compound (1.6 g, 93%); m/z 262.7

Step-7: N—((R)-1-(4-Fluoronaphthalen-1-yl)ethyl)-3-((S)-4-oxo-1,2,3,4-tetrahydronaphthalen-2-yl)propanamide To the stirred solution of (R)-3-(4-oxo-1,2,3,4-tetrahydronaphthalen-2-yl)propanoic acid (0.8 g, 3.67 mmol) (Crude) in dry DMF (15 mL), CDI (0.713 g, 4.40 mmol) was added. The reaction mixture was stirred at RT for 0.5 h. Then (R)-1-(4-fluoronaphthalen-1-yl)ethanamine (0.832 g, 4.40 mmol) was added and the reaction mixture was stirred at RT for 2 h. After completion of reaction ice was added to reaction mixture, solid precipitated out was filtered through Buchner funnel to get title compound (830 mg, 58.1%); m/z 390.54. Crude was taken without purification for next reaction.

Step-8: (3R)-3-(3-(((R)-1-(4-Fluoronaphthalen-1-yl)ethyl)amino)propyl)-1,2,3,4-tetrahydronaphthalen-1-ol N—((R)-1-(4-Fluoronaphthalen-1-yl)ethyl)-3-((R)-4-oxo-1,2,3,4-tetrahydronaphthalen-2-yl)propanamide (830 mg, 2.131 mmol) was added to a suspension of LAH (162 mg, 4.26 mmol) in dioxane (15 mL) at 0° C. The reaction mixture was stirred for 30 minutes at 25° C. and heated at 100° C. and further maintained for 12 h. The mixture was allowed to RT, cooled to 0° C. and slowly quenched with ethyl acetate (5 mL) followed by water (5 mL). Reaction mixture was extracted with ethyl acetate (30 mL), washed with brine solution (20 mL) and dried over $Na_2SO_4$ and concentrated to get crude compound which was used as it is in next reaction; m/z 378.6.

Step-9: tert-Butyl((R)-1-(4-fluoronaphthalen-1-yl)ethyl)(3-((2R)-4-hydroxy-1,2,3,4-tetrahydronaphthalen-2-yl)propyl)carbamate To a mixture of (3R)-3-(3-(((R)-1-(4-fluoronaphthalen-1-yl)ethyl)amino)propyl)-1,2,3,4-tetrahydronaphthalen-1-ol (800 mg, 2.119 mmol) and TEA (0.738 mL, 5.30 mmol) in acetonitrile (10 mL), $Boc_2O$ (0.590 mL, 2.54 mmol) was added at 25° C. The reaction mixture was heated to 55° C. and further maintained for 12 h. To this reaction mixture, water was added (15 mL) and extracted with ethyl acetate (2×15 mL). The organic phase was washed with brine solution (10 mL), dried over $Na_2SO_4$ and filtered. The clear organic phase was evaporated in vacuo to get crude compound. This crude compound was used as it is in next reaction. (886 mg, 88% yield).

Step-10: tert-Butyl((R)-1-(4-fluoronaphthalen-1-yl)ethyl)(3-((R)-4-oxo-1,2,3,4-tetrahydronaphthalen-2-yl)propyl)carbamate To a stirred solution of tert-Butyl((R)-1-(4-fluoronaphthalen-1-yl)ethyl)(3-((2R)-4-hydroxy-1,2,3,4-tetrahydronaphthalen-2-yl)propyl)carbamate (886 mg, 1.855 mmol) DCM (8 mL), PCC (304 mg, 2.226 mmol) was added at 0° C. and stirred for 1 h at 25° C. The reaction mixture was filtered through celite bed and the filtrate concentrated to get the crude compound. This crude compound was purified by column chromatography (Biotage) using eluent (1:9, ethyl acetate:n-hexane) to get the title compound (500 mg). m/z 476.42.

Step-11: (R)-3-(3-((tert-Butoxycarbonyl)((R)-1-(4-fluoronaphthalen-1-yl)ethyl)amino)propyl)-3,4-dihydronaphthalen-1-yl trifluoromethanesulfonate The Step-11 compound was prepared by following the similar procedure as described in step-8 of Intermediate-6; m/z 607.2.

Intermediate-9

(S)-3-(3-((tert-Butoxycarbonyl)((R)-1-(naphthalen-1-yl)ethyl)amino)propyl)-3,4-dihydronaphthalen-1-yl trifluoromethanesulfonate

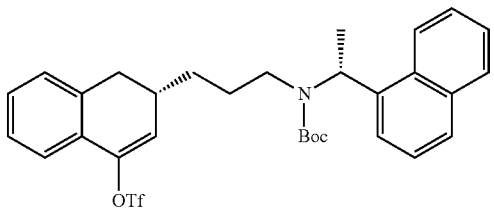 [SMILES: C[C@H](c1cccc2ccccc12)N(CCC[C@@H]1C=C(OS(=O)(=O)C(F)(F)F)c2ccccc2C1)C(=O)OC(C)(C)C]

The title compound was prepared by following the similar procedure as described in step-7 of Intermediate-7 followed by step-8 and step-10 of Intermediate-8 in sequential manner by using (S)-3-(4-oxo-1,2,3,4-tetrahydronaphthalen-2-yl) propanoic acid and (R)-1-(naphthalen-1-yl)ethanamine; m/z 590.58.

Intermediate-10

(R)-3-(3-((tert-Butoxycarbonyl)((R)-1-(4-fluoro-3-methoxyphenyl)ethyl)amino)propyl)-3,4-dihydronaphthalen-1-yl trifluoromethanesulfonate

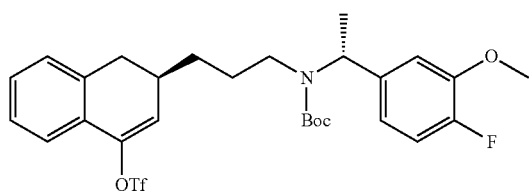 [SMILES: COc1cc([C@@H](C)N(CCC[C@H]2C=C(OS(=O)(=O)C(F)(F)F)c3ccccc3C2)C(=O)OC(C)(C)C)ccc1F]

The title compound was prepared by following the similar procedure as described in step-7 of Intermediate-7 followed by step-8 and step-10 of Intermediate-8 in sequential manner by using (R)-3-(4-oxo-1,2,3,4-tetrahydro naphthalen-2-yl) propanoic acid and (R)-1-(4-fluoro-3-methoxyphenyl)ethanamine.

Intermediate-11

Methyl quinoline-3-carboxylate

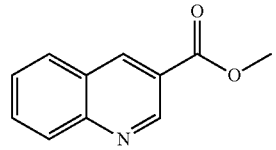

The solution of quinoline-3-carboxylic acid (3 g, 17.32 mmol) in methanol (30 mL) was cooled on ice bath at 0° C. Then thionyl chloride (1.264 mL, 17.32 mmol) was added and the reaction mixture was heated to 80° C. and maintained overnight. Reaction was monitored by TLC. After completion of reaction methanol was evaporated under reduced pressure and the resultant residue was basified with saturated sodium bicarbonate to make pH (7 to 8) to get white solid which was filtered and dried to get methyl quinoline-3-carboxylate (3.2 g, yield-99%) as a white solid; m/z-187.3.

Intermediate-12

Methyl 1,2,3,4-tetrahydroquinoline-3-caroxylate

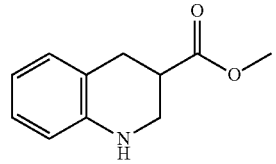

To a solution of Intermediate-11 (3 g, 16.03 mmol) in MeOH (100 mL), sodium cyanoborohydride (5.04 g, 80 mmol) and then a small amount of bromocresol green (pH indicator) was added. 4M HCl solution in dioxane (5 mL×3) in 30 min interval was added drop-wise into reaction mixture to make pH acidic (4 to 5), till reaction mixture maintained a yellow color then reaction mixture was stirred at RT for 16 h. Reaction was monitored by TLC/LCMS. After completion of reaction, the reaction mixture was quenched with sodium bicarbonate and extracted with ethyl acetate (20×3 mL). The combined organic layer was dried and concentrated under reduced pressure. The crude compound was purified by flash chromatography by using (20% ethyl acetate in hexane) to get methyl 1,2,3,4-tetrahydroquinoline-3-carboxylate (1.5 g, yield 49%) as yellow color oily mass; m/z-191.7

Intermediate-13a, 13b

N—((R)-1-(Naphthalen-1-yl)ethyl)-1,2,3,4-tetrahydroquinoline-3-carboxamide

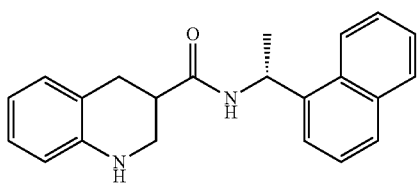 [SMILES: C[C@@H](NC(=O)C1CNc2ccccc2C1)c1cccc2ccccc12]

A solution of (R)-1-(naphthalen-1-yl)ethanamine (25.07 g, 146 mmol) and trimethyl aluminium (54.9 mL, 110 mmol) in toluene (250 mL) was heated at 55° C. for 45 min. To this reaction mixture Intermediate-12 (14 g, 73.2 mmol) was added at 55° C. and the reaction mixture was further heated to 110° C. and maintained for 20 h. The progress of reaction was monitored by TLC. The reaction mixture was cooled to 0° C. and quenched with dilute HCl. After basified with saturated $Na_2CO_3$, product extracted with ethyl acetate (100 mL×2). The organic layer was washed with water (2×50 mL) followed by brine solution (50 mL). The organic layers were combined, dried over sodium sulfate and concentrated. Crude product was purified. Further isomers were separated by flash chromatography (25% ethyl acetate/hexane) to get Intermediate-13a (8 g) and Intermediate-13b (4 g); m/z-353 as $Na^{+1}$.

Intermediate-14a, 14b (1R)-1-(Naphthalen-1-yl)-N-((1,2,3,4-tetrahydroquinolin-3-yl)methyl)ethanamine

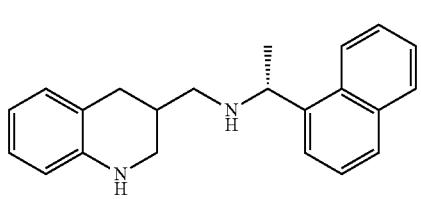 [SMILES: C[C@@H](NCC1CNc2ccccc2C1)c1cccc2ccccc12]

To a solution of Intermediate-13a (2.3 g, 6.96 mmol) in THF (20 mL) was cooled to 0° C. then added borane-methyl sulfide complex (1.74 mL, 17.40 mmol) at the same temperature. The reaction mixture was heated to 70° C. and maintained for 7 h. The progress of reaction was monitored by TLC, after completion of reaction the reaction mixture was cooled to 0° C. and added 1:1 dilute HCl solution very slowly (10 mL). The reaction mixture was heated to 90° C. and maintained for 1 h. Tetrahydrofuran was distilled off under vacuum, residue was cooled to 0° C. and basified with 2M NaOH solution [pH=10] and extracted in ethyl acetate (50 mL×2). The combined organic layer was washed with water (2×25 mL) followed by brine solution (25 mL). The organic layer was dried over anhydrous $Na_2SO_4$ and evaporated the solvent under reduced pressure to get the title compound (2 g, 90% yield) at as yellow-brown oily mass; m/z-317.1 Similarly Intermediate-14b was also prepared by using Intermediate-13b from above method.

Intermediate-15

Methyl 6-fluoroquinoline-3-carboxylate

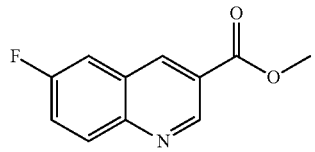

To a solution of 5-fluoro-2-nitrobenzaldehyde (5 g, 29.6 mmol), methyl 3,3-dimethoxy propanoate (10.95 g, 73.9 mmol) in ethanol (100 mL). Tin Chloride (22.43 g, 118 mmol) was slowly added in above solution. The reaction mixture was heated to 90° C. for 4 h. Reaction progress was monitored by TLC. After completion of reaction ethanol was evaporated under reduced pressure and the resultant residue was basified with saturated sodium bicarbonate. The resulting emulsion was filtered through celite, rinsed well with ethyl acetate. The remaining aqueous layer was extracted with ethyl acetate and the combined organic layers were washed with brine, dried over sodium sulfate and concentrated. The residue was purified by flash chromatography (30% ethyl acetate/hexanes) to get desired compound. (3.1 g, 51.1% yield); m/z-206.76.

Intermediate-16

(1R)—N-((6-Fluoro-1,2,3,4-tetrahydroquinolin-3-yl)methyl)-1-(naphthalen-1-yl)ethanamine

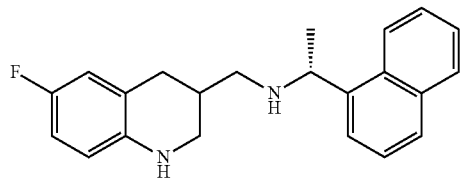 [SMILES: C[C@@H](NCC1CNc2ccc(F)cc2C1)c1cccc2ccccc12]

The title compound was prepared in three steps:

Step: 1—Intermediate-15 was carried-out reduction with sodium cyanoborohydride by following the similar procedure as described in Intermediate-12;

Step: 2—Condensation of Step-1 intermediate with (R)-1-(naphthalen-1-yl)ethanamine by following the similar procedure as described in Intermediate-13a,13b;

Step: 3—Reduction of Step-2 Intermediate using borane dimethyl sulphide complex by following the similar procedure as described in Intermediate-14a,14b; m/z: 334.8.

Intermediate-17

(1R)-1-(4-Fluoronaphthalen-1-yl)-N-((1,2,3,4-tetrahydroquinolin-3-yl)methyl)ethanamine

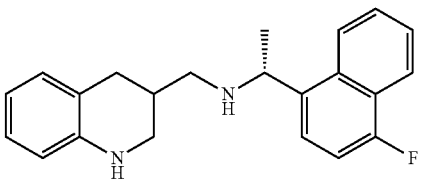 [SMILES: C[C@@H](NCC1CNc2ccccc2C1)c1ccc(F)c2ccccc12]

The title compound was prepared in two steps:

Step: 1—Intermediate-12 was reacted with corresponding (R)-1-(4-fluoronaphthalen-1-yl)ethanamine hydrochloride by following the similar procedure as described in Intermediate-13a,13b.

Step: 2—Step-1 Intermediate was undergone reduction reaction using borane dimethyl sulphide complex by following the similar procedure as described in Intermediate-14a, 14b; m/z-334.9.

Intermediate-18

(1R)-1-(4-Fluoro-3-methoxyphenyl)-N-((1,2,3,4-tetrahydroquinolin-3-yl)methyl)ethanamine

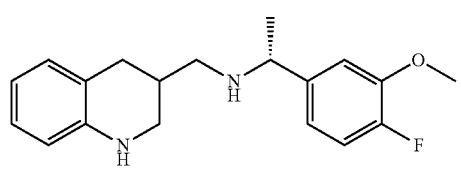 [SMILES: COc1cc([C@@H](C)NCC2CNc3ccccc3C2)ccc1F]

The title compound was prepared in two steps:

Step: 1—Intermediate-12 was reacted with corresponding (R)-1-(4-fluoro-3-methoxy phenyl)ethanamine by following the similar procedure as described in Intermediate-13a,13b.

Step: 2: Step-1 Intermediate was carried-out reduction reaction using borane dimethyl sulphide complex by following the similar procedure as described in Intermediate-14a, 14b; m/z-315.65.

Intermediate-19

1-tert-Butyl 3-methyl 3,4-dihydroquinoline-1,3(2H)-dicarboxylate

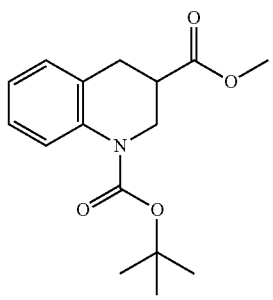 [SMILES: COC(=O)C1Cc2ccccc2N(C(=O)OC(C)(C)C)C1]

To a solution of Intermediate-12 (1 g, 5.23 mmol) in acetonitrile (10 mL), BOC-anhydride (1.457 mL, 6.28 mmol) was added at RT. The reaction mixture was heated up to 50° C. for overnight. Reaction progress was monitored by TLC. Organic solvent was removed under vacuum. Product was extracted in ethyl acetate (10 mL×2). Washed the organic layer with saturated citric acid (10 mL) followed by water (10 mL) and saturated brine solution (10 mL). Organic layer was dried over sodium sulphate, concentrated under vacuum to get crude product. Further the crude product was purified by flash chromatography (10% ethyl acetate in n-hexane and 1% NH$_4$OH) to get title compound (1.35 g, 89% yield); m/z 313.9 as Na+1.

Intermediate-20 tert-Butyl 3-formyl-3,4-dihydroquinoline-1(2H)-carboxylate

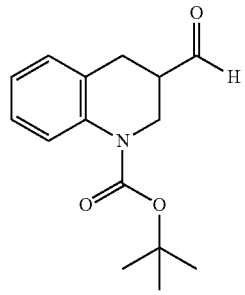 [SMILES: CC(C)(C)OC(=O)N1CC(C=O)Cc2ccccc21]

To a solution of Intermediate-19 (0.2 g, 0.686 mmol) in a mixture of dry toluene (8 mL) and DCM (2 mL) DIBAL-H (1.37 mL, 1.37 mmol, 1M) was added in drop wise manner at −78° C. Further the reaction was stirred for 2 h at the same temperature. The progress of reaction was monitored by TLC. Reaction mixture was quenched with MeOH (5 mL) at −65° C. and allowed to RT, filtered through celite, diluted with water (20 mL). It was extracted with ethyl acetate (20 mL×2) washed with water (15 mL) and brine solution (15 mL), dried over Na$_2$SO$_4$ and concentrated under reduced pressure to get the crude product. This crude product was further purified by flash chromatography (10% ethyl acetate in hexane) to give the title compound (0.12 g, 66.9%); m/z-283.5 as Na+1

Intermediate-21 tert-Butyl 3-(2-oxoethyl)-3,4-dihydroquinoline-1 (2H)-carboxylate

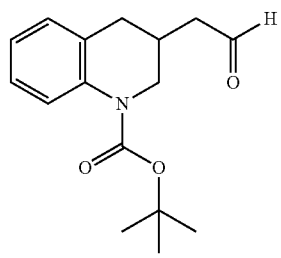 [SMILES: CC(C)(C)OC(=O)N1CC(CC=O)Cc2ccccc21]

To a solution of (methoxymethylene)triphenyl phosphorane (703 mg, 2.296 mmol) in THF (5 mL). The solution was cooled to −30° C. for 15 min and potassium tert.butoxide (322 mg, 2.87 mmol) dissolved in THF (5 mL) was added. Stirred this solution for 30 min wine red color solution observed. Intermediate-20 (500 mg, 1.913 mmol) in THF (5 mL) was added to the reaction mixture. This solution was stirred for 2 h at the same temperature. The progress of reaction was monitored by TLC. After completion of reaction, water (5 mL) was added and product was extracted with ethyl acetate (10 mL×3) followed by water (10 mL) and brine (10 mL). Organic solvent was evaporated under reduced pressure. Further it was purified by flash column chromatography (5% ethyl acetate in hexane) to get (E)-tert-butyl 3-(2-methoxyvinyl)-3,4-dihydroquinoline-1(2H)-carboxylate (225 mg, 40.6% yield); m/z-312.1 as Na+1.

To a solution of (E)-tert-butyl 3-(2-methoxyvinyl)-3,4-dihydroquinoline-1(2H)-carboxylate (225 mg, 0.778 mmol) in THF (5 mL) dilute HCl (0.2 ml, 6.58 mmol) was added. The reaction mixture was stirred overnight at RT. The progress of reaction was monitored by TLC. After completion of reaction methanol was evaporated under reduced pressure. Further it was purified by flash column chromatography (15% ethyl acetate in hexane) to get the title compound (160 mg, 30.4% yield); m/z-297.6 as Na+1.

Intermediate-22 tert-Butyl 3-(2-(((R)-1-(naphthalen-1-yl)ethyl)amino)ethyl)-3,4-dihydroquinoline-1(2H)-carboxylate

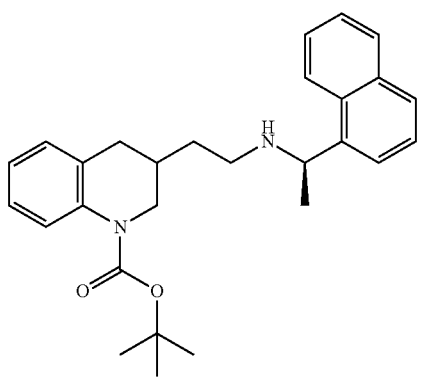 [SMILES: C[C@@H](NCCC1Cc2ccccc2N(C(=O)OC(C)(C)C)C1)c1cccc2ccccc12]

To a stirred solution of Intermediate-21 (1.15 g, 4.18 mmol) in methanol (10 mL) (R)-1-(naphthalen-1-yl)ethanamine (0.858 g, 5.01 mmol) was added at 0° C. Acetic acid (0.2 ml, 3.49 mmol) was added and reaction was stirred for 5 min. Reaction was warmed to RT and stirred for 20 min. Again reaction was cooled to 0° C. Sodium cyanoborohydride (0.525 g, 8.35 mmol) was added to the reaction mixture and stirred for overnight. Reaction progress was monitored by TLC. To the reaction NaHCO$_3$ solution (20 mL) were added and water (50 mL) and the mixture was extracted with ethyl acetate (50 mL×2). The extract was washed with saturated brine, dried over anhydrous Na$_2$SO$_4$ and evaporated under reduced pressure to get crude product. Further compound was purified by using column purification (10% ethyl acetate-hexane) to get title compound (1.2 g, 66.7% yield); m/z-431.54.

Intermediate-23

(1R)-1-(Naphthalen-1-yl)-N-(2-(1,2,3,4-tetrahydroquinolin-3-yl)ethyl)ethanamine

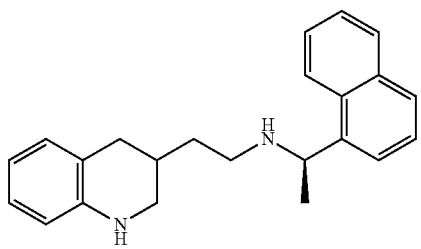 [SMILES: C[C@@H](NCCC1CNc2ccccc2C1)c1cccc2ccccc12]

Intermediate-22 (1.2 g, 2.79 mmol) was dissolved in DCM (5 mL) and MeOH/HCl (10 mL, 3N). The reaction mixture was stirred at RT overnight. The progress of reaction was monitored by TLC. The reaction was evaporated under reduced pressure then added saturated Na$_2$CO$_3$ solution (5 mL). The mixture was extracted with ethyl acetate (10 mL×2) and washed with water (5 mL×2) followed by brine solution (5 mL), dried over Na$_2$SO$_4$ and concentrated under reduced pressure. This was further purified by flash chromatography (15% ethyl acetate-hexane) to give title compound (1 g, 98% yield); m/z-331.65.

Intermediate-24

(E)-tert-Butyl3-(3-ethoxy-3-oxoprop-1-en-1-yl)-3,4-dihydroquinoline-1(2H)-carboxylate

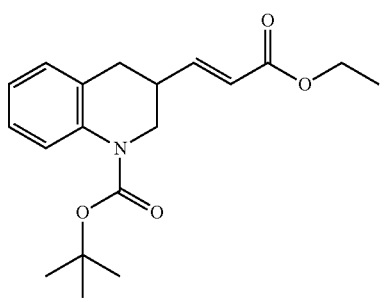 [SMILES: CCOC(=O)/C=C/C1Cc2ccccc2N(C(=O)OC(C)(C)C)C1]

The solution of Intermediate-20 (8 g, 30.6 mmol) and ethyl 2-(triphenyl phosphoranylidene) acetate (11.73 g, 33.7 mmol) in toluene (100 mL) was heated to 110° C. and maintained for 3 h. The progress of reaction was monitored by TLC. Reaction mixture was allowed to RT then diluted with water (50 mL) and extracted with ethyl acetate (50 mL×3). The combined organic layer was washed with water (50 mL) followed by brine solution (50 mL), dried over Na$_2$SO$_4$ and concentrated to give crude product. The crude product was further purified by flash chromatography (10% ethyl acetate in hexane) to give title compound (8.5 g, yield: 84%); m/z-276.58 (M-55).

Intermediate-25 tert-Butyl 3-(3-ethoxy-3-oxopropyl)-3,4-dihydroquinoline-1(2H)-carboxylate

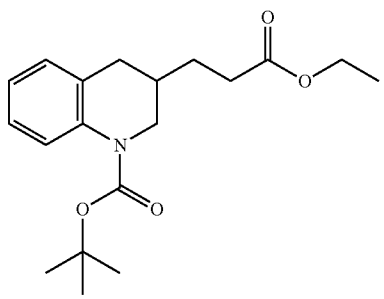 [SMILES: CCOC(=O)CCC1Cc2ccccc2N(C(=O)OC(C)(C)C)C1]

To a suspension of 10% palladium on carbon (2 g, 50% wet) in ethanol (20 mL), Intermediate-24 (9 g, 27.2 mmol) in ethanol (80 mL) was carefully added and the mixture was stirred overnight under a pressure of hydrogen balloon. The progress of reaction was monitored by TLC. Reaction mixture was filtered through celite and the filtrate concentrated to get the crude product (9 g, 99%); m/z-234.89 (M-98).

Intermediate-26

3-(1-(tert-Butoxycarbonyl)-1,2,3,4-tetrahydroquinolin-3-yl)propanoic acid

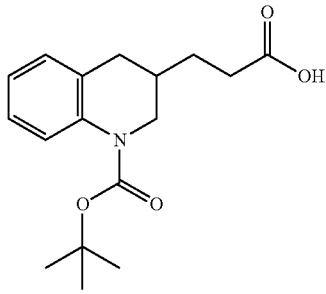 [SMILES: CC(C)(C)OC(=O)N1CC(CCC(=O)O)Cc2ccccc21]

To a solution of Intermediate-25 (9.2 g, 27.6 mmol) in THF (25 mL), MeOH (25 mL) and water (3 mL) lithium hydroxide hydrate (5.79 g, 138 mmol) was added. The reaction mixture was stirred for 2 h at RT. The progress of reaction was monitored by TLC. The reaction mixture was concentrated under vacuum then cooled to 0° C. and acidified with citric acid solution. The mixture was extracted with ethyl acetate (50 mL×2), washed with water (25 mL×2) followed by brine solution (25 mL), dried over $Na_2SO_4$ and concentrated under vacuum to get white solid. (8.22 g, 99.83%); m/z-306.59.

Intermediate-27 tert-Butyl3-(3-(((R)-1-(naphthalen-1-yl)ethyl)amino)-3-oxopropyl)-3,4-dihydro quinoline-1(2H)-carboxylate

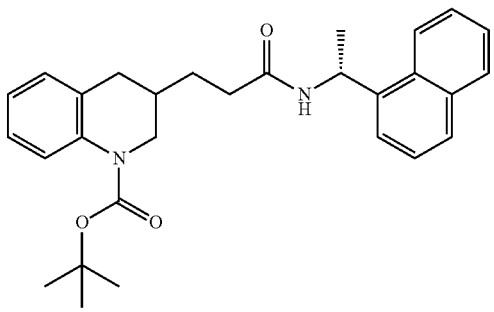 [SMILES: C[C@@H](NC(=O)CCC1Cc2ccccc2N(C(=O)OC(C)(C)C)C1)c1cccc2ccccc12]

To a solution of Intermediate-26 (2.5 g, 8.19 mmol) in DMF (10 mL) CDI (1.991 g, 12.28 mmol) was added slowly and stirred for 30 min. Then (R)-1-(naphthalen-1-yl)ethanamine (1.682 g, 9.82 mmol) was added. The reaction mixture was wormed to 35° C. and further maintained for 24 h. Reaction progress was monitored by TLC. Poured RM into water (50 mL) and product was extracted with ethyl acetate (25 mL×2). The organic layer was washed with 20% citric acid (25 mL) followed by water (25 mL×2), saturated $Na_2CO_3$ solution. Finally the organic layer was washed with water and saturated brine solution (25 mL). Dried the organic layer on $Na_2SO_4$ then evaporated under reduced pressure to get crude title compound (3.7 g, 99% yield); m/z-459.48.

Intermediate-28

N—((R)-1-(Naphthalen-1-yl)ethyl)-3-(1,2,3,4-tetrahydroquinolin-3-yl)propan-1-amine

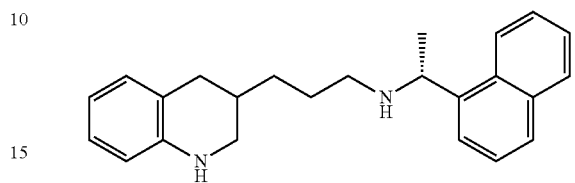

The title compound was prepared by following the similar procedure as described in Intermediate-14a,14b by taking Intermediate-27; m/z-345.66.

Intermediate-29

N—((R)-1-(4-Fluoronaphthalen-1-yl)ethyl)-3-(1,2,3,4-tetrahydroquinolin-3-yl)propan-1-amine

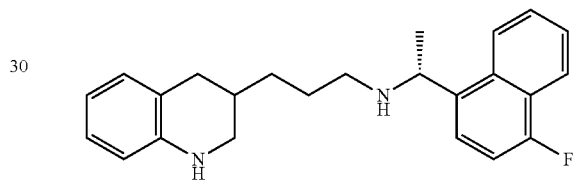

The title compound was prepared in two steps:
Step: 1—Intermediate-26 was reacted with (R)-1-(4-fluoronaphthalen-1-yl)ethanamine hydrochloride by following the similar procedure as described in Intermediate-27.
Step: 2—Step-1 Intermediate has undergone reduction using borane dimethyl sulphide complex by following the similar procedure as described in Intermediate-14a14b; m/z-363.66.

EXAMPLES

Example-1

Methyl 3-(3-((((R)-1-(Naphthalen-1-yl)ethyl)amino)methyl)-1,2,3,4-tetrahydronaphthalen-1-yl)benzoate

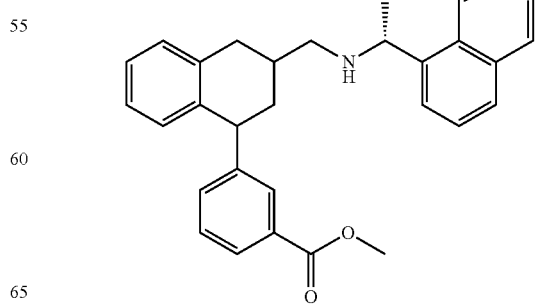

Step-1: Methyl 3-(3-(((tert-butoxycarbonyl)((R)-1-(naphthalen-1-yl)ethyl)amino)methyl)-3,4-dihydronaphthalen-1-yl)benzoate To a solution of Intermediate-1 (1 g, 1.781 mmol), methyl 3-(4,4,5,5-tetramethyl-1,3,2-dioxaborolan-2-yl)benzoate (0.467 g, 1.781 mmol) and sodium carbonate (0.321 g, 5.34 mmol) in ethanol (5 mL), toluene (5 mL) and water (2 mL) bubbled the nitrogen for 30 minutes. Tetrakis(triphenylphosphine)palladium(0) (23 mg, 0.089 mmol) was added to the reaction mixture and again nitrogen was bubbled for 10 minutes. The reaction mixture was then heated to 65° C. and further maintained for 1 h. Reaction was monitored by TLC. The resulting solid was removed by filtration through celite bed. The filtrate was extracted with ethyl acetate (2×25 mL) and washed with water (15 mL) and brine solution (15 mL). The organic layer was dried over sodium sulfate and concentrated under reduced pressure to get crude compound. This crude compound was further purified by flash chromatography (Biotage) (ethyl acetate:hexane=1:20) to give title compound (660 mg, 67.7%) m/z 548.57.

Step-2: Methyl 3-(3-(((tert-butoxycarbonyl)((R)-1-(naphthalen-1-yl)ethyl)amino)methyl)-1,2,3,4-tetrahydronaphthalen-1-yl)benzoate To a stirred solution of above step-1 intermediate (660 mg, 1.205 mmol) in MeOH (10 mL), palladium on carbon (10%) (66 mg) was carefully added and the mixture was stirred under pressure of balloon of hydrogen for 8 h. Reaction mixture was filtered through celite bed and concentrated to get the crude compound. This was used directly in next reaction (570 mg, 86%). m/z 550.57.

Step-3: Methyl 3-(3-((((R)-1-(naphthalen-1-yl)ethyl)amino)methyl)-1,2,3,4-tetra hydronaphthalen-1-yl)benzoate To a stirred solution of step-2 intermediate (570 mg, 1.092 mmol) in methanol (8 ml), HCl in methanol (2.24 mL, 7.26 mmol) was added and the reaction mixture was stirred at 25° C. overnight in closed vessel. The reaction mixture was basified with saturated sodium bicarbonate solution and extracted with ethyl acetate (2×25 mL). Organic layer was washed with brine solution (20 mL), dried over sodium sulfate and concentrated under reduced pressure to get crude compound. This crude compound was purified by reverse phase HPLC. Further the four diastereomers were separated by chiral preparative HPLC [CELLULOSE 1, 250 mm×4.6, 5µ; A: hexane/IPA (90:10, % v/v, 0.1% DEA) B:IPA(100%) A:B 80/20% v/v Flow=1.0 ml/min] Isomer 'a': $t_R$=6.28, Isomer 'b': $t_R$=8.66, Isomer 'c': $t_R$=9.40, Isomer 'd': $t_R$=12.56; m/z, 449.60. ($t_R$ is retention time).

Example-2a, 2b, 2c, 2d 3-(3-((((R)-1-(Naphthalen-1-yl)ethyl)amino)methyl)-1,2,3,4-tetrahydronaphthalen-1-yl)benzoic acid hydrochloride

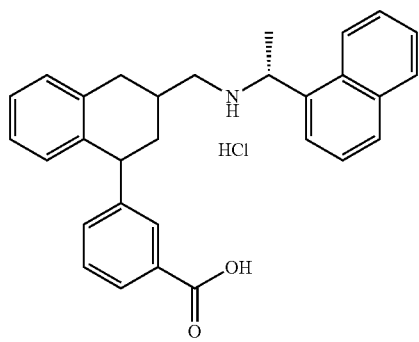 [SMILES: C[C@@H](NCC1Cc2ccccc2C(c2cccc(C(=O)O)c2)C1)c1cccc2ccccc12 ; Cl]

To a stirred solution of Isomer 'a' of Example-1 (25 mg, 0.056 mmol) in ethanol (2.0 ml), tetrahydrofuran (2.0 mL) and water (2.0 mL) in round bottom flask. LiOH (9.32 mg, 0.389 mmol) was added and reaction mixture was heated to 80° C. and further maintained for 2 h. Reaction mixture was concentrated and acidified with 6N HCl solution, solid was precipitated out. This solid was filtered, washed with DM water (20 mL) and n-pentane (20 mL) dried to get the title product (22 mg, 91%). m/z 435.98.

This solid compound was dissolved in dry DCM (1 mL), then slowly added with 2 M ethereal HCl solution (2 mL) and further maintained for few minutes. The reaction mixture was distilled off completely and further washed with diethyl ether and dried to get HCl salt of title compound.

$^1$H NMR (400 MHz, DMSO): δ 12.92 (bs, 1H), 9.43 (bs, 1H), 9.05 (bs, 1H), 8.14 (d, J=8 Hz, 1H), 8.01-7.93 (m, 3H), 7.77 (d, J=8 Hz, 1H), 7.63-7.58 (m, 3H), 7.53 (m, 1H), 7.43-7.39 (m, 1H), 7.27 (d, J=7.6 Hz, 1H), 7.18-7.17 (m, 2H), 7.09-7.08 (m, 1H), 6.83 (d, J=7.6 Hz, 1H), 5.28 (q, J=6.4 Hz, 1H), 4.40-4.37 (m, 1H), 3.21-3.16 (m, 1H), 3.00 (m, 1H), 2.72-2.67 (m, 1H), 2.33-2.18 (m, 2H), 1.92-1.89 (m, 2H), 1.65 (d, J=6.4 Hz, 3H); m/z 435.98

Similarly, Example-2b, Example-2c and Example-2d were prepared from Example-1 Isomer 'b', Example-1 Isomer 'c' and Example-1 isomer 'd' respectively.

Example-2b: $^1$H NMR (400 MHz, DMSO): δ 12.95 (bs, 1H), 9.65 (bs, 1H), 9.20 (bs, 1H), 8.26 (d, J=8.4 Hz, 1H), 8.03-7.95 (m, 3H), 7.83-7.80 (m, 1H), 7.72 (m, 1H), 7.67-7.58 (m, 4H), 7.47-7.41 (m, 2H), 7.12-7.09 (m, 2H), 7.03-7.00 (m, 1H), 5.36 (q, J=6.4 Hz, 1H), 4.14-4.18 (m, 1H), 3.73-3.40 (m, 1H), 3.06-3.04 (m, 1H), 2.88 (m, 1H), 2.68-2.65 (m, 1H), 2.38-2.33 (m, 2H), 2.28-2.23 (m, 1H), 1.72 (d, J=6.4 Hz, 3H); m/z 435.98.

Example-2c: $^1$H NMR (400 MHz, DMSO): δ 12.91 (bs, 1H), 9.47 (bs, 1H), 9.04 (bs, 1H), 8.13 (d, J=8 Hz, 1H), 8.00-7.94 (m, 3H), 7.77 (d, J=7.6 Hz, 1H), 7.62-7.57 (m, 3H), 7.52 (m, 1H), 7.43-7.39 (m, 1H), 7.27 (d, J=8 Hz, 1H), 7.17-7.16 (m, 2H), 7.08-7.07 (m, 1H), 6.82 (d, J=7.6 Hz, 1H), 5.25 (q, J=6.8 Hz, 1H), 4.36-4.33 (m, 1H), 3.14-2.82 (m, 2H), 2.73 (m, 1H), 2.67-2.54 (m, 1H), 2.22 (m, 1H), 1.97-1.93 (m, 2H), 1.65 (d, J=6.8 Hz, 3H); m/z 435.91.

Example-2d: $^1$H NMR (400 MHz, DMSO): δ 12.96 (bs, 1H), 9.73 (bs, 1H), 9.14 (bs, 1H), 8.25 (d, J=8.4 Hz, 1H), 8.02-7.97 (m, 3H), 7.82-7.80 (m, 1H), 7.71 (m, 1H), 7.64-7.59 (m, 3H), 7.45-7.44 (m, 2H), 7.11-7.10 (m, 2H), 7.02-7.00 (m, 1H), 6.58 (d, J=8.4 Hz, 1H), 5.37 (q, J=6.8 Hz, 1H), 4.20-4.15 (m, 1H), 3.09 (m, 2H), 2.91-2.78 (m, 1H), 2.78-2.41 (m, 1H), 2.69-2.62 (m, 1H), 2.33-2.30 (m, 2H), 1.76 (d, J=6.8 Hz, 3H); m/z 435.98.

The Example-3 to Example-7 and their isomers given in Table-1 were prepared by following the similar procedure as described in Step-1 to Step-3 of Example-1 by taking Intermediate-1 and appropriately substituted phenyl boronic acid/ester. Further the diastereomers were separated by similar chiral preparative HPLC method as described in Example-1a, 1b,1c,1d.

TABLE 1

| E. No | Structure | Chemical Name | Mass (m/z) |
|---|---|---|---|
| 3a, 3b, 3c | 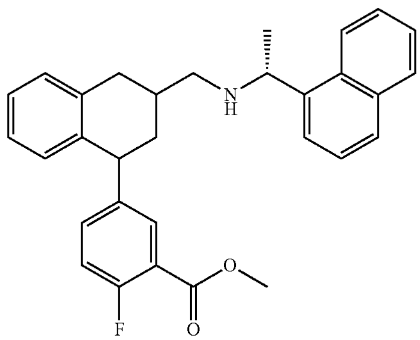 [SMILES: COC(=O)c1cc(C2CC(CN[C@H](C)c3cccc4ccccc34)Cc3ccccc32)ccc1F] | Methyl 2-fluoro-5-(3-((((R)-1-(naphthalene-1-yl)ethyl)amino)methyl)-1,2,3,4-tetrahydronaphthalen-1-yl)benzoate | 466.92 |
| 4a, 4b, 4c, 4d | 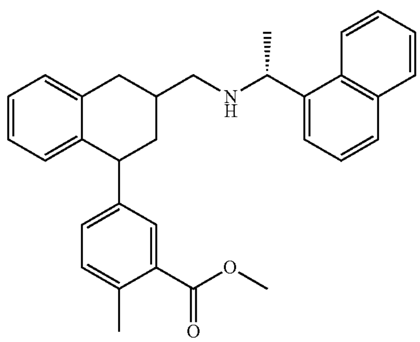 [SMILES: COC(=O)c1cc(C2CC(CN[C@H](C)c3cccc4ccccc34)Cc3ccccc32)ccc1C] | Methyl 2-methyl-5-(3-((((R)-1-(naphthalen-1-yl)ethyl)amino)methyl)-1,2,3,4-tetrahydronaphthalen-1-yl)benzoate | 464.1 |
| 5a, 5b, 5c | 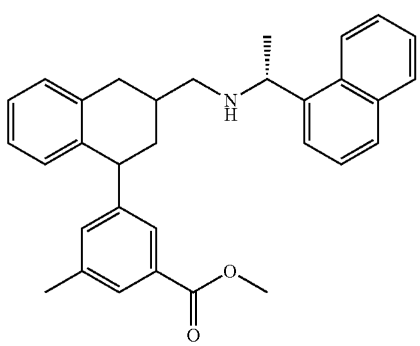 [SMILES: COC(=O)c1cc(C)cc(C2CC(CN[C@H](C)c3cccc4ccccc34)Cc3ccccc32)c1] | Methyl 3-methyl-5-(3-((((R)-1-(naphthalen-1-yl)ethyl)amino)methyl)-1,2,3,4-tetrahydronaphthalen-1-yl)benzoate | 464.1 |
| 6a, 6b, 6c | 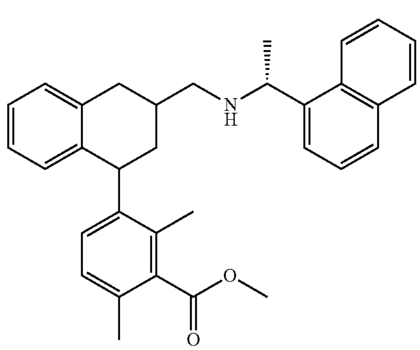 [SMILES: COC(=O)c1c(C)ccc(C2CC(CN[C@H](C)c3cccc4ccccc34)Cc3ccccc32)c1C] | Methyl 2,6-dimethyl-3-(3-((((R)-1-(naphthalen-1-yl)ethyl)amino)methyl)-1,2,3,4-tetrahydronaphthalen-1-yl)benzoate | 478.1 |

The Example-7 to Example-10 and their isomers given in Table-2 were prepared by following the similar ester hydrolysis procedure as described in Example-2a,2b,2c,2d by taking corresponding ester Example given in Table-1. Further, hydrochloride salt of these compounds were prepared by following the similar hydrochloride salt procedure as described in Example-2a,2b,2c,2d.

TABLE 2

| E. No | Structure | Chemical Name | |
|---|---|---|---|
| 7a, 7b, 7c | 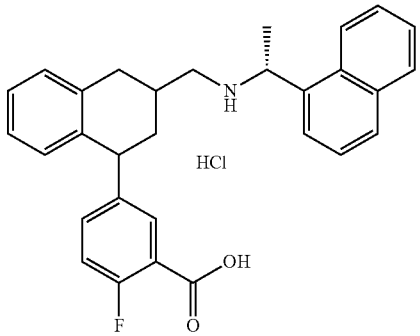 2-Fluoro-5-(3-((((R)-1-(naphthalen-1-yl)ethyl)amino)methyl)-1,2,3,4-tetrahydronaphthalen-1-yl)benzoic acid hydrochloride | 7a: $^1$H NMR (400 MHz, DMSO): δ 13.23 (bs, 1H), 9.40 (bs, 1H), 9.01 (bs, 1H), 8.21 (d, J = 8 Hz, 1H), 8.01-7.92 (m, 3H), 7.63-7.58 (m, 3H), 7.41-7.39 (m, 1H), 7.24-7.22 (m, 2H), 7.17-7.16 (m, 2H), 7.09-7.08 (m, 1H), 8.31 (d, J = 8.4 Hz, 1H), 5.26 (q, J = 6.8 Hz, 1H), 4.34 (m, 1H), 3.16-3.07 (m, 2H), 2.82 (m, 1H), 2.61-2.54 (m, 1H), 2.18 (m, 1H), 1.97-1.87 (m, 2H), 1.66 (d, J = 6.8 Hz, 3H); m/z 454.<br>7b: $^1$H NMR (400 MHz, DMSO): δ 13.26 (bs, 1H), 9.48 (bs, 1H), 9.18 (bs, 1H), 8.25 (d, J = 8.4 Hz, 1H), 8.02-7.97 (m, 3H), 7.65-7.59 (m, 4H), 7.43-7.40 (m, 1H), 7.28-7.24 (m, 1H), 7.11-7.09 (m, 2H), 7.46-7.7.01 (m, 1H), 8.59 (d, J = 7.6 Hz, 1H), 5.36 (q, J = 6.4 Hz, 1H), 4.19-4.14 (m, 1H), 3.06 (m, 1H), 2.91-2.87 (m, 1H), 2.76 (m, 1H), 2.68-2.65 (m, 2H), 2.37-2.32 (m, 2H), 1.72 (d, J = 6.4 Hz, 3H); m/z 454.<br>7c: $^1$H NMR (400 MHz, DMSO): δ 13.26 (bs, 1H), 9.48 (bs, 1H), 9.18 (bs, 1H), 8.26 (d, J = 7.6 Hz, 1H), 8.03-8.00 (m, 2H), 7.91 (d, J = 6.8 Hz, 1H), 7.64-7.60 (m, 4H), 7.24 (m, 1H), 7.30-7.25 (m, 1H), 7.11 (m, 2H), 7.03 (m, 1H), 6.60 (d, J = 8 Hz, 1H), 5.37 (q, J = 6.4 Hz, 1H), 4.17-4.15 (m, 1H), 3.09-3.05 (m, 1H), 2.96-2.92 (m, 2H), 2.68-2.61 (m, 2H), 2.33 (m, 1H), 2.22-2.20 (m, 1H), 1.70 (d, J = 6.4 Hz, 3H), m/z 454.1 | |
| 8a, 8b, 8c, 8d | 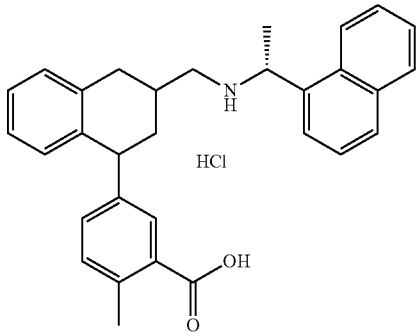 2-Methyl-5-(3-((((R)-1-(naphthalen-1-yl)ethyl)amino)methyl)-1,2,3,4-tetrahydro naphthalen-1-yl)benzoic acid hydrochloride | 8a: $^1$H NMR (400 MHz, DMSO): δ 12.76 (bs, 1H), 9.53 (bs, 1H), 9.06 (bs, 1H), 8.15 (d, J = 8.0 Hz, 1H), 8.01-7.96 (m, 3H), 7.63-7.56 (m, 3H), 7.42 (d, J = 1.6 Hz, 1H), 7.20-7.14 (m, 3H), 7.09-7.03 (m, 2H), 6.81 (d, J = 7.6 Hz, 1H), 5.29-5.24 (m, 1H), 4.28-4.25 (m, 1H), 3.13-3.04 (m, 2H), 2.81 (m, 1H), 2.59-2.55 (m, 1H), 2.46 (s, 3H), 2.22 (m, 1H), 1.94-1.87 (m, 2H), 1.66 (d, J = 6.8 Hz, 3H); m/z 449.85.<br>8b: $^1$H NMR (400 MHz, DMSO): δ 12.81 (bs, 1H), 9.55 (bs, 1H), 9.02 (bs, 1H), 8.27 (d, J = 8.4 Hz, 1H), 8.03-7.98 (m, 2H), 7.93 (d, J = 6.8 Hz, 1H), 7.66-7.58 (m, 4H), 7.24 (s, 2H), 7.10-7.09 (m, 2H), 7.03-6.99 (m, 1H), 6.60 (d, J = 8 Hz, 1H), 5.39-5.37 (m, 1H), 4.12-4.08 (m, 1H), 3.40-3.35 (m, 1H), 3.10 (m, 1H), 2.90-2.87 (m, 1H), 2.77-2.74 (m, 1H), 2.68-2.60 (m, 1H), 2.50 (s, 3H), 2.33-2.24 (m, 2H), 1.71 (d, J = 6.4 Hz, 3H); m/z 449.79.<br>8c: $^1$H NMR (400 MHz, DMSO): δ 12.81 (bs, 1H), 9.57 (bs, 1H), 9.14 (bs, 1H), 8.28 (d, J = 8.4 Hz, 1H), 8.03-7.98 (m, 3H), 7.67-7.58 (m, 4H), 7.24 (S, 2H), 7.10 (d, J = 8.0 Hz, 2H), 7.03-7.00 (m, 1H), 6.61 (d, J = 7.6 Hz, 1H), 5.37 (m, 1H), 4.10-4.06 (m, 1H), 3.06-2.88 (m, 3H), 2.67-2.60 (m, 1H), 2.46 (S, 3H), 2.45-2.35 (m, 3H) 1.67 (d, J = 6.8 Hz, 3H); m/z 450.1<br>8d: $^1$H NMR (400 MHz, DMSO): δ 8.15 (d, J = 9.2 Hz, 1H), 8.01-7.96 (m, 2H), 7.90 (d, J = 8.0 Hz, 1H), 7.63-7.56 (m, 3H), 7.41-7.40 (m, 1H), 7.20-7.14 (m, 3H), 7.10-7.03 (m, 2H), 6.83 (d, J = 8.0 Hz, 1H), 5.30-5.28 (m, 1H), 4.32-4.29 (m, 1H), 3.17-3.12 (m, 1H), 3.02-2.97 (m, 1H), 2.73-2.67 (m, 1H), 2.50-2.46 (m, 4H), 2.32-2.19 (m, 1H), 1.88-1.85 (m, 2H), 1.64 (d, J = 6.8 Hz, 3H); m/z 450.1 | |

TABLE 2-continued

| E. No | Structure | Chemical Name | |
|---|---|---|---|
| 9a, 9b, 9c | 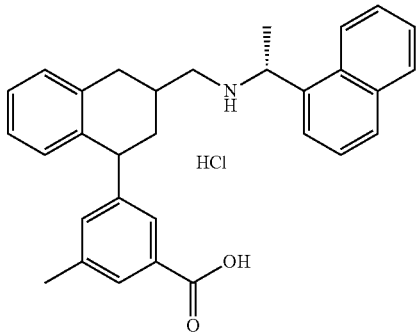 3-Methyl-5-(3-((((R)-1-(naphthalen-1-yl)ethyl) amino)methyl)-1,2,3,4-tetrahydro naphthalen-1-yl)benzoic acid hydrochloride | 9a: ¹H NMR (400 MHz, DMSO): δ 12.83 (bs, 1H), 9.24 (bs, 1H), 8.91 (bs, 1H), 8.16 (d, J = 8.0 Hz, 1H), 8.01-7.96 (m, 2H), 7.88 (d, J = 7.2 Hz, 1H), 7.73-7.56 (m, 4H), 7.27 (s, 1H), 7.17-7.06 (m, 4H), 6.82 (d, J = 7.6 Hz, 1H), 5.28-5.25 (m, 1H), 4.31-4.29 (m, 1H), 3.13-3.08 (m, 2H), 2.83 (m, 1H), 2.62-2.55 (m, 1H), 2.30 (s, 3H), 2.25-2.21 (m, 1H), 1.95-1.87 (m, 2H), 1.65 (d, J = 6.8 Hz, 3H); m/z 450.1<br>9b: ¹H NMR (400 MHz, DMSO): δ 12.86 (bs, 1H), 9.43 (bs, 1H), 9.10 (bs, 1H), 8.27 (d, J = 8.8 Hz, 1H), 8.03-7.96 (m, 2H), 7.95 (d, J = 7.2 Hz, 1H), 7.67-7.58 (m, 4H), 7.52 (s, 1H), 7.27 (s, 1H), 7.11 (d, J = 4.0 Hz, 2H), 7.04-7.00 (m, 1H), 6.61 (d, J = 7.6 Hz, 1H), 5.38-5.36 (m, 1), 4.13-4.09 (m, 1H), 3.05-2.92 (m, 3H), 2.68-2.33 (m, 2H), 2.33-2.21 (m, 5H), 1.70 (d, J = 6.4 Hz, 3H); m/z 450.1<br>9c: ¹H NMR (400 MHz, DMSO): δ 12.87 bs, 1H), 9.61 (bs, 1H), 9.08 (bs, 1H), 8.27 (d, J = 8.8 Hz, 1H), 8.03-7.93 (m, 3H), 7.65-7.58 (m, 4H), 7.52 (s, 1H), 7.25 (s, 1H), 7.10-7.00 (m, 3H), 6.61 (d, J = 8 Hz, 1H), 5.39-5.37 (m, 1), 4.14-4.10 (m, 1H), 3.40-3.09 (m, 2H), 2.90-2.62 (m, 3H), 2.33-2.26 (m, 5H), 1.71 (d, J = 6.8 Hz, 3H); m/z 450.67. | |
| 10a, 10b, 10c | 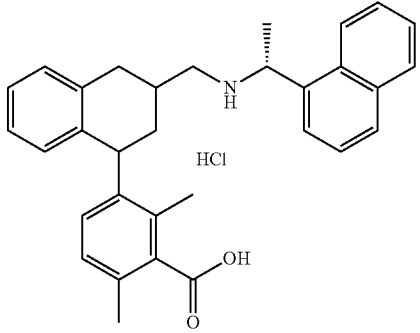 2,6-Dimethyl-3-(3-((((R)-1-(naphthalen-1-yl)ethyl)amino)methyl)-1,2,3,4-tetrahydro naphthalen-1-yl)benzoic acid hydrochloride | 10a: ¹H NMR (400 MHz, DMSO): δ 13.19 (bs, 1H), 9.58 (bs, 1H), 9.17 (bs, 1H), 8.26 (d, J = 8.8 Hz, 1H), 8.03-7.92 (m, 3H), 7.66-7.55 (m, 3H), 7.15-6.98 (m, 4H), 6.90-6.78 (m, 1H), 6.57 (d, J = 7.6 Hz, 1H), 5.36 (q, J = 6.7 Hz, 1H), 4.32-4.30 (m, 1H), 3.29-2.78 (m, 3H), 2.72-2.58 (m, 1H), 2.36-2.33 (m, 3H), 2.18 (s, 5H), 1.86 (m, 1H), 1.72 (d, J = 6.8 Hz, 3H), m/z 468.48<br>10b: ¹H NMR (400 MHz, DMSO): δ 13.20 (bs, 1H), 9.66 (bs, 1H), 9.09 (bs, 1H), 8.27 (d, J = 8.4 Hz, 1H), 8.31-7.96 (m, 3H), 7.66-7.56 (m, 3H), 7.15-7.08 (m, 2H), 7.03-7.00 (m, 2H), 6.82-6.81 (m, 1H), 6.57 (d, J = 7.6 Hz, 1H), 5.38 (q, J = 6.4 Hz, 1H), 4.32-4.31 (m, 1H), 3.12-3.08 (m, 1H), 2.88-2.78 (m, 2H), 2.67-2.60 (m, 1H), 2.33 (s, 3H), 2.17 (s, 5H), 1.80 (m, 1H), 1.68 (d, J = 6.4 Hz, 3H); m/z 463.8<br>10c: ¹H NMR (400 MHz, DMSO): δ 13.19 (bs, 1H), 9.41 (bs, 1H), 9.02 (bs, 1H), 8.18 (d, J = 8.4 Hz, 1H), 8.01-7.94 (m, 3H), 7.63-7.56 (m, 3H), 7.15-7.12 (m, 2H), 7.07-7.03 (m, 1H), 6.87 (d, J = 8 Hz, 1H), 6.76 (d, J = 7.6 Hz, 1H), 6.32 (d, J = 7.6 Hz, 1H), 5.27 (m, 1H), 4.45-4.42 (m, 1H), 3.14-3.06 (m, 3H), 2.83 (m, 1H), 2.34 (s, 3H), 2.22-2.21 (m, 1H), 2.17 (s, 3H), 1.66-1.65 (m, 2H), 1.65 (d, J = 6.4 Hz, 3H); m/z 463.8 | |

Example-11a, 11b

Methyl 2-methyl-4-((3S)-3-((((R)-1-(naphthalen-1-yl)ethyl)amino)methyl)-1,2,3,4-tetrahydronaphthalen-1-yl)benzoate

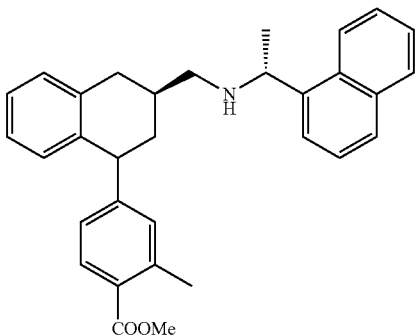 [SMILES: COC(=O)c1ccc(C2C[C@H](CN[C@H](C)c3cccc4ccccc34)Cc3ccccc32)cc1C]

The title compound was prepared by following the similar procedure as described in Step-1 to Step-3 of Example-1 in sequential manner by taking Intermediate-2 and methyl 2-methyl-4-(4,4,5,5-tetramethyl-1,3,2-dioxaborolan-2-yl)benzoate.

The two diastereomers were separated by chiral preparative HPLC [CHIRAL PAK ID, 250 mm×4.6, 5μ; A=n-hexane IPA (90/10% v/v, 0.1% DEA), B=IPA; A:B=90/10% v/v; Flow=1.0 ml/min] Isomer 'a': $t_R$=5.07, Isomer 'b': $t_R$=5.92; m/z, 464.1. ($t_R$ is retention time).

Example-12a, 12b

Methyl 4-methyl-3-((3S)-3-((((R)-1-(naphthalen-1-yl)ethyl)amino)methyl)-1,2,3,4-tetrahydronaphthalen-1-yl)benzoate

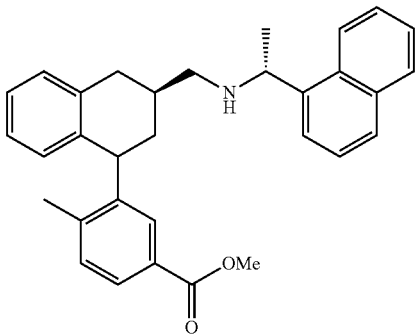 [SMILES: COC(=O)c1ccc(C)c(C2C[C@H](CN[C@H](C)c3cccc4ccccc34)Cc3ccccc32)c1]

The title compound was prepared by following the similar procedure as described in Step-1 to Step-3 of Example-1 in sequential manner by taking Intermediate-2 and methyl 4-methyl-3-(4,4,5,5-tetramethyl-1,3,2-dioxaborolan-2-yl)benzoate.

The two diastereomers were separated by chiral preparative HPLC [CHIRAL PAK ID, 250 mm×4.6, 5μ; A=n-hexane IPA (90/10% v/v, 0.1% DEA), B=IPA; A:B=90/10% v/v; Flow=1.0 ml/min] Isomer 'a': $t_R$=5.76, Isomer 'b': $t_R$=6.70; m/z, 464.48. ($t_R$ is retention time).

Example-13a, 13b

2-Methyl-4-((3S)-3-((((R)-1-(naphthalen-1-yl)ethyl)amino)methyl)-1,2,3,4-tetrahydronaphthalen-1-yl)benzoic acid hydrochloride

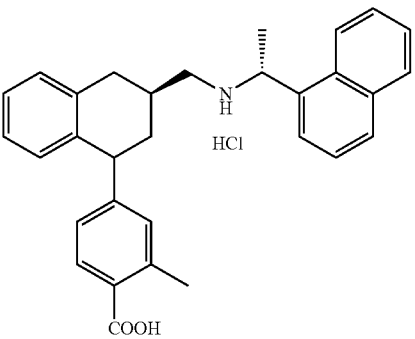 [SMILES: Cc1cc(C2C[C@H](CN[C@H](C)c3cccc4ccccc34)Cc3ccccc32)ccc1C(=O)O ; Cl]

The title compounds of Example-13a,13b were prepared by following the similar ester hydrolysis procedure as described in Example-2a by taking corresponding ester Example-11a and Example-11b. Further, hydrochloride salt of these compounds was prepared by following the similar hydrochloride salt procedure as described in Example-2a.

13a: $^1$H NMR (400 MHz, DMSO): δ 12.70 (bs, 1H), 9.21 (bs, 1H), 8.90 (bs, 1H), 8.16 (d, J=8.0 Hz, 1H), 8.01-7.97 (m, 2H), 7.87 (d, J=6.8 Hz, 1H), 7.72 (d, J=8 Hz, 1H), 7.64-7.57 (m, 3H), 7.19-7.16 (m, 2H), 7.11-7.06 (m, 1H), 6.94 (s, 1H), 6.84-6.79 (m, 2H), 5.29-5.27 (m, 1H), 4.28-4.26 (m, 1H), 3.12-3.07 (m, 2H), 2.83 (m, 1H), 2.58-2.45 (m, 4H), 2.21 (m, 1H), 1.95-1.90 (m, 2H), 1.65 (d, J=6.4 Hz, 3H); m/z 450.1

13b: $^1$H NMR (400 MHz, DMSO): δ 12.73 (bs, 1H), 9.47 (bs, 1H), 8.98 (bs, 1H), 8.27 (d, J=8.4 Hz, 1H), 8.02-7.99 (m, 2H), 7.90 (m, 1H), 7.79 (d, J=8 Hz, 1H), 7.62 (m, 3H), 7.10-7.02 (m, 4H), 6.61 (d, J=6.8 Hz, 1H), 5.39 (m, 1H), 4.98 (m, 1H), 3.11 (m, 1H), 2.91-2.61 (m, 4H), 2.50 (s, 3H), 2.33-2.27 (m, 2H), 1.70 (m, 3H); m/z 450.1.

Example-14a, 14b

4-Methyl-3-((3S)-3-((((R)-1-(naphthalen-1-yl)ethyl)amino)methyl)-1,2,3,4-tetrahydronaphthalen-1-yl)benzoic acid hydrochloride

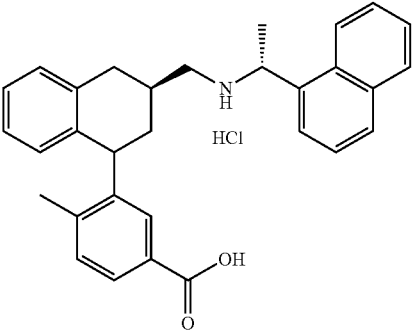 [SMILES: Cc1ccc(C(=O)O)cc1C1C[C@H](CN[C@H](C)c2cccc3ccccc23)Cc2ccccc21 ; Cl]

The title compounds of Example-14a,14b were prepared by following the similar ester hydrolysis procedure as described in Example-2a by taking corresponding ester Example-12a and Example-12b. Further, hydrochloride salt of these compounds was prepared by following the similar hydrochloride salt procedure as described in Example-2a.

14a: ¹H NMR (400 MHz, DMSO): δ 12.77 (bs, 1H), 9.73 (bs, 1H), 9.17 (bs, 1H), 8.27 (d, J=8.4 Hz, 1H), 8.03-7.97 (m, 3H), 7.70-7.57 (m, 4H), 7.47 (m, 1H), 7.33-7.31 (m, 1H), 7.11 (m, 2H), 7.02-6.99 (m, 1H), 6.54 (d, J=7.6 Hz, 1H), 5.40-5.35 (m, 1H), 4.39-4.35 (m, 1H), 3.16-3.09 (m, 1H), 2.91-2.88 (m, 1H), 2.80-2.63 (m, 3H), 2.50 (s, 3H), 2.45-2.29 (m, 2H), 1.73 (d, J=6.8 Hz, 3H); m/z 450.

14b: ¹H NMR (400 MHz, DMSO): δ 12.68 (bs, 1H), 9.23 (bs, 1H), 8.98 (bs, 1H), 8.17 (d, J=7.2 Hz, 1H), 8.01-7.97 (m, 2H), 7.90-7.88 (m, 1H), 7.67-7.60 (m, 4H), 7.33 (m, 1H), 7.18 (s, 2H), 7.06 (m, 2H), 6.80 (d, J=6 Hz, 1H), 5.27 (m, 1H), 4.49 (m, 1H), 3.16-3.12 (m, 2H), 2.82 (m, 1H), 2.67-2.55 (m, 1H), 2.50 (s, 1H), 2.18 (m, 1H), 1.87 (m, 2H), 1.64 (m, 3H); m/z 450.

Example-15a, 15b

Methyl 5-((3S)-3-((((R)-1-(4-fluoro-3-methoxyphenyl)ethyl)amino)methyl)-1,2,3,4-tetra hydronaphthalen-1-yl)-2-methylbenzoate

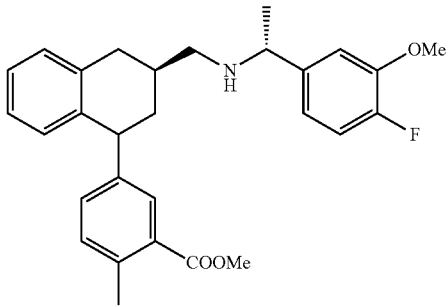 [SMILES: COC(=O)c1cc(C2C[C@H](CN[C@H](C)c3ccc(F)c(OC)c3)Cc3ccccc32)ccc1C]

The title compound was prepared by following the similar procedure as described Step-1 to Step-3 of Example-1 in sequential manner by taking Intermediate-3 and (3-(methoxycarbonyl)-4-methylphenyl)boronic acid.

The two diastereomers were separated by chiral preparative HPLC [CHIRAL PAK ID, 250 mm×4.6, 5µ; A=n-hexane IPA (90/10% v/v, 0.1% DEA), B=IPA; A:B=90/10% v/v; Flow=1.0 ml/min] Isomer 'a': $t_R$=6.05, Isomer 'b': $t_R$=6.62; m/z, 461.9. ($t_R$ is retention time).

Example-16a, 16b 5-((3S)-3-((((R)-1-(4-Fluoro-3-methoxyphenyl)ethyl)amino)methyl)-1,2,3,4-tetrahydronaphthalen-1-yl)-2-methylbenzoic acid hydrochloride

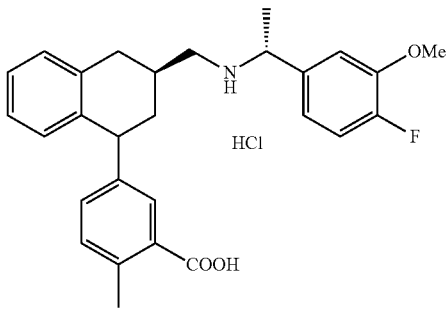 [SMILES: COc1cc([C@@H](C)NC[C@@H]2Cc3ccccc3C(c3ccc(C)c(C(=O)O)c3)C2)ccc1F ; Cl]

The title compounds Example-16a,16b were prepared by following the similar ester hydrolysis procedure as described in Example-2a by taking corresponding ester Example-15a and Example-15b. Further, hydrochloride salt of these compounds was prepared by following the similar hydrochloride salt procedure as described in Example-2a.

16a: ¹H NMR (400 MHz, DMSO): δ 12.77 (bs, 1H), 9.29 (bs, 1H), 9.03 (bs, 1H), 7.51 (dd, J=2, 8.4 Hz, 1H), 7.43 (d, J=1.6 Hz, 1H), 7.25-7.13 (m, 4H), 7.10-7.02 (m, 3H), 6.81 (d, J=7.6 Hz, 1H), 4.29-4.24 (m, 2H), 3.84 (s, 3H), 3.10-3.05 (m, 1H), 2.86-2.84 (m, 1H), 2.67-2.46 (m, 5H), 2.18-2.15 (m, 1H), 1.95-1.87 (m, 2H), 1.57 (d, J=6.4 Hz, 3H); m/z 448.04.

16b: ¹H NMR (400 MHz, DMSO): δ 12.81 (bs, 1H), 9.56 (bs, 1H), 9.21 (bs, 1H), 7.58-7.56 (m, 2H), 7.42-7.21 (m, 3H), 7.15-7.07 (m, 3H), 7.03-6.99 (m, 1H), 6.60 (d, J=7.6 Hz, 1H), 4.40-4.39 (m, 1H), 4.12-4.07 (m, 1H), 3.84 (s, 3H), 2.89-2.86 (m, 2H), 2.69-2.45 (m, 6H), 2.33-2.25 (m, 2H), 1.62 (d, J=6.8 Hz, 3H); m/z 448.04.

Example-17

3-((3S)-3-((((R)-1-(4-Fluoro-3-methoxyphenyl)ethyl)amino)methyl)-1,2,3,4-tetrahydronaphthalen-1-yl)-2,6-dimethylbenzoic acid hydrochloride

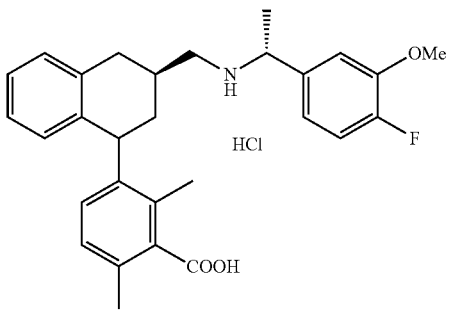 [SMILES: COc1cc([C@@H](C)NC[C@@H]2Cc3ccccc3C(c3ccc(C)c(C(=O)O)c3C)C2)ccc1F ; Cl]

Step-1: Benzyl 3-((R)-3-(((tert-butoxycarbonyl)((R)-1-(4-fluoro-3-methoxyphenyl)ethyl)amino)methyl)-3,4-dihydronaphthalen-1-yl)-2,6-dimethylbenzoate To a solution of Intermediate-3 (2.1 g, 3.75 mmol), benzyl 2,6-dimethyl-3-(4,4,5,5-tetramethyl-1,3,2-dioxaborolan-2-yl)benzoate (1.512 g, 4.13 mmol) and sodium carbonate (1.193 g, 11.26 mmol) in EtOH (10 mL), Toluene (10 mL) and water (5 mL) bubbled nitrogen for 30 min. tetrakis(triphenylphosphine)palladium(0) (0.217 g, 0.188 mmol) was added and again nitrogen was bubbled for 10 min. Reaction was then heated at 65° C. for 1 hr. The resulting solid was removed by filtration through Celite. The filtrate was extracted with ethyl acetate (2×25 mL) and washed with water (15 mL) and brine (15 mL). The organic layer was dried over sodium sulfate, and filtered, after concentration under reduced pressure to give crude compound. The crude compound was purified with silica gel flash column chromatography (Biotage) using eluent 5% EtOAc:hexane to yield benzyl 3-((R)-3-(((tert-butoxycarbonyl)((R)-1-(4-fluoro-3-methoxyphenyl)ethyl)amino)methyl)-3,4-dihydro naphthalen-1-yl)-2,6-dimethylbenzoate (1.3 g, 53.3%) as an oil; m/z-Boc 550.3.

Step-2: 3-((3S)-3-(((tert-butoxycarbonyl)((R)-1-(4-fluoro-3-methoxyphenyl)ethyl)amino)methyl)-1,2,3,4-tetrahydronaphthalen-1-yl)-2,6-dimethylbenzoic acid To a stirred solution of Pd/C (0.130 g, 0.122 mmol) in MeOH (20 mL), step-1 (1.3 g, 2.001 mmol) was added under nitrogen atmosphere. Reaction mixture was stirred overnight under hydrogen balloon pressure. Compound was filtered through celite, concentrated to yield 1.2 g of crude compound. The crude compound was purified by Prep HPLC to get pure title compound. Further diastereomers separated by chiral prep HPLC [CELLULOSE-1, 250 mm×4.6, 5µ; A=n-hexane, 0.2% TFA B=ETOH 100%; A=70/30% V/V; flow rate 1.0 ml/min] to yield title compound (Isomer 'a': $t_R$=3.42, 220 mg, 91.46%); m/z 562.07. ($t_R$ is retention time).

Step-3: 3-((3S)-3-((((R)-1-(4-Fluoro-3-methoxyphenyl)ethyl)amino)methyl)-1,2,3,4-tetrahydronaphthalen-1-yl)-2,6-dimethylbenzoic acid hydrochloride To the stirred solution of step-2 intermediate (220 mg, 0.392 mmol), in DCM (5 mL) was added HCl in methanol (2M) (1.958 mL, 3.92 mmol) at 0° C. and stirred the reaction mixture at RT for 16 h. Solvent was removed under reduced pressure and solid obtained was washed with diethyl ether and n-pentane to yield the title compound as a white solid. (120 mg, 61.5%). $^1$H NMR (400 MHz, DMSO): δ 13.11 (bs, 1H), 9.70 (bs, 1H), 9.27 (bs, 1H), 7.54 (d, J=6.8 Hz, 1H), 7.30-7.25 (m, 1H), 7.12-6.82 (m, 5H), 6.88-6.82 (m, 1H), 6.58-6.55 (m, 1H), 4.39-4.31 (m, 2H), 3.84 (s, 3H), 2.89-2.86 (m, 2H), 2.66-2.49 (m, 5H), 2.33-2.21 (m, 6H), 1.62 (d, J=6.4 Hz, 3H); m/z 462.48.

Example-18a, 18b

Methyl 5-((3S)-3-((((R)-1-(4-fluoronaphthalen-1-yl)ethyl)amino)methyl)-1,2,3,4-tetrahydronaphthalen-1-yl)-2-methylbenzoate

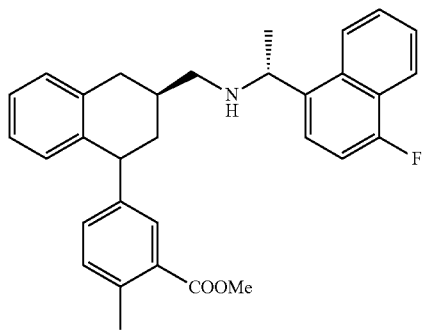 [SMILES: COC(=O)c1cc(C2C[C@H](CN[C@H](C)c3ccc(F)c4ccccc34)Cc3ccccc32)ccc1C]

The title compound was prepared by following the similar procedure as described Step-1 to Step-3 of Example-1 in sequential manner by taking Intermediate-4 and (3-(methoxycarbonyl)-4-methylphenyl)boronic acid.

The two diastereomers were separated by chiral preparative HPLC [CHIRAL PAK IA 250 mm×4.6, 5µ; A=n-hexane: IPA (90:10% v/v, 0.1% DEA), B=IPA; A:B=95/5% V/V; Flow=1.0 ml/min] Isomer 'a': $t_R$=4.71, Isomer 'b': $t_R$=5.56; m/z, 481.67. ($t_R$ is retention time).

Example-19a, 19b 5-((3S)-3-((((R)-1-(4-Fluoronaphthalen-1-yl)ethyl)amino)methyl)-1,2,3,4-tetrahydronaphthalen-1-yl)-2-methylbenzoic acid hydrochloride

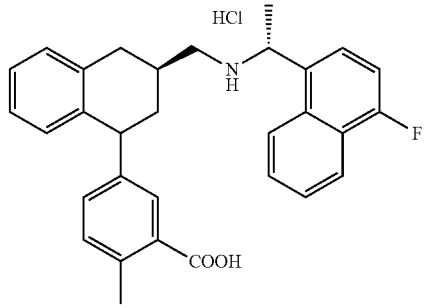 [SMILES: Cc1ccc(C2C[C@H](CN[C@H](C)c3ccc(F)c4ccccc34)Cc3ccccc32)cc1C(=O)O ; Cl]

The title compounds of Example-19a, 19b were prepared by following the similar ester hydrolysis procedure as described in Example-2a by taking Example-18a and Example-18b. Further, hydrochloride salts of these compounds were prepared by following the similar hydrochloride salt procedure as described in Example-2a.

19a: $^1$H NMR (400 MHz, DMSO): δ 12.80 (s, 1H), 9.40 (bs, 1H), 9.10 (bs, 1H), 8.25 (d, J=8.0 Hz, 1H), 8.14-8.12 (m, 1H), 7.96-7.94 (m, 1H), 7.73-7.69 (m, 2H), 7.50-7.45 (m, 1H), 7.41-7.40 (m, 1H), 7.20-7.07 (m, 3H), 7.05-7.03 (m, 2H), 6.82 (d, J=7.6 Hz, 1H), 5.25-5.24 (m, 1H), 4.29-4.28 (m, 1H), 3.12-3.04 (m, 2H), 2.81-2.76 (m, 1H), 2.67-2.54 (m, 1H), 2.51-2.45 (m, 3H), 2.19-2.18 (m, 1H), 1.95-1.89 (m, 2H), 1.65 (d, J=6.4 Hz, 3H); m/z: 467.90

19b: $^1$H NMR (400 MHz, DMSO): δ 12.80 (s, 1H), 9.79 (bs, 1H), 9.16 (bs, 1H), 8.35 (d, J=8.0 Hz, 1H), 8.16-8.13 (m, 1H), 8.03-8.00 (m, 1H), 7.77-7.69 (m, 2H), 7.60-7.59 (m, 1H), 7.51-7.47 (m, 1H), 7.26-7.22 (m, 2H), 7.09-7.08 (m, 2H), 7.02-6.98 (m, 1H), 6.59 (d, J=7.6 Hz, 1H), 5.35-5.34 (m, 1H), 4.11-4.07 (m, 1H), 3.40-3.34 (m, 2H), 3.10-3.06 (m, 1H), 2.90-2.87 (m, 1H), 2.76-2.45 (m, 3H), 2.35-2.26 (m, 3H), 1.71 (d, J=6.4 Hz, 3H); m/z: 467.90

Example-20

Methyl 2-methyl-5-(3-(((R)-1-(naphthalen-1-yl)ethyl)amino)-1,2,3,4-tetrahydronaphthalen-1-yl)benzoate

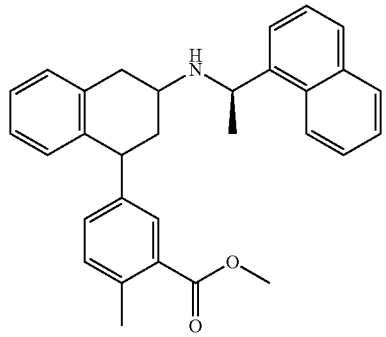 [SMILES: COC(=O)c1cc(C2CC(N[C@H](C)c3cccc4ccccc34)Cc3ccccc32)ccc1C]

The title compound was prepared by following the similar procedure as described in Step-1 to Step-3 of Example-1 in sequential manner by taking Intermediate-5 and (3-(methoxycarbonyl)-4-methylphenyl)boronic acid; m/z: 449.48.

Example-21

Methyl 2-methyl-4-(3-(((R)-1-(naphthalen-1-yl)ethyl)amino)-1,2,3,4-tetrahydronaphthalen-1-yl)benzoate

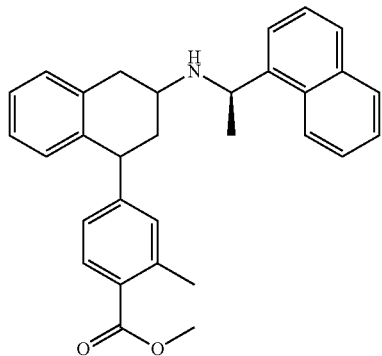 [SMILES: COC(=O)c1ccc(C2CC(N[C@H](C)c3cccc4ccccc34)Cc3ccccc32)cc1C]

The title compound was prepared by following the similar procedure as described in Step-1 to Step-3 of Example-1 in sequential manner by taking Intermediate-5 and methyl 2-methyl-4-(4,4,5,5-tetramethyl-1,3,2-dioxaborolan-2-yl)benzoate; m/z: 449.48

Example-22

2-Methyl-5-(3-(((R)-1-(naphthalen-1-yl)ethyl)amino)-1,2,3,4-tetrahydronaphthalen-1-yl)benzoic acid hydrochloride

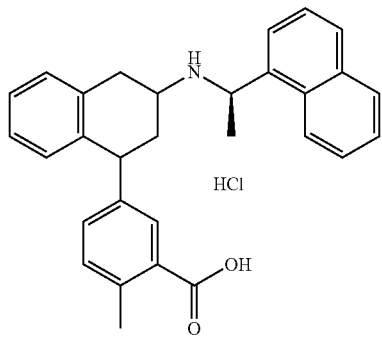 [SMILES: Cc1ccc(C2CC(N[C@H](C)c3cccc4ccccc34)Cc3ccccc32)cc1C(=O)O ; Cl]

The title compound was prepared by following the similar ester hydrolysis procedure as described in Example-2a by taking corresponding ester Example-20. Further, hydrochloride salt was prepared by following the similar hydrochloride salt procedure as described in Example-2a. $^1$H NMR (400 MHz, DMSO): δ 12.88 (s, 1H), 10.20 (bs, 1H), 9.67 (bs, 1H), 8.41 (d, J=8.4 Hz, 1H), 8.13 (d, J=7.2 Hz, 1H), 8.01-7.98 (m, 2H), 7.66-7.57 (m, 4H), 7.29-7.22 (m, 2H), 7.09-7.06 (m, 2H), 7.02-6.98 (m, 1H), 6.52 (d, J=7.6 Hz, 1H), 5.58-5.56 (m, 1H), 4.22-4.18 (m, 1H), 3.48-3.40 (m, 1H), 3.38-3.17 (m, 3H), 2.69-2.66 (m, 2H), 2.08-1.97 (m, 2H), 1.76 (d, J=6.4 Hz, 3H); m/z 436.42.

Example-23

2-Methyl-4-(3-(((R)-1-(naphthalen-1-yl)ethyl)amino)-1,2,3,4-tetrahydronaphthalen-1-yl)benzoic acid hydrochloride

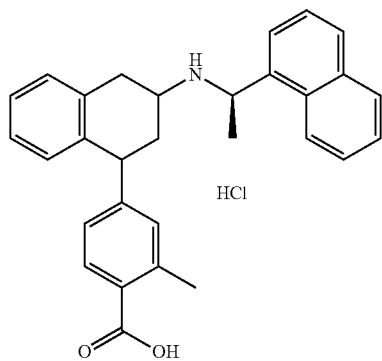 [SMILES: Cc1cc(C2CC(N[C@H](C)c3cccc4ccccc34)Cc3ccccc32)ccc1C(=O)O ; Cl]

The title compound was prepared by following the similar ester hydrolysis procedure as described in Example-2a by taking corresponding ester Example 21. Further, hydrochloride salt was prepared by following the similar hydrochloride salt procedure as described in Example-2a. $^1$H NMR (400 MHz, DMSO): δ 12.76 (s, 1H), 10.24 (bs, 1H), 9.72 (bs, 1H), 8.41 (d, J=8.4 Hz, 1H), 8.14 (d, J=7.2 Hz, 1H), 8.01-7.97 (m, 2H),7.81 (d, J=8.0 Hz, 1H), 7.66-7.57 (m, 3H), 7.10-6.98 (m, 5H), 6.53 (d, J=7.6 Hz, 1H), 5.58-5.56 (m, 1H), 4.20-4.16 (m, 1H), 3.47-3.35 (m, 2H), 3.31-3.19 (m, 3H), 2.66-2.49 (m, 2H), 2.08-1.99 (m, 1H), 1.76 (d, J=6.4 Hz, 3H m/z 436.1

Example-24

Methyl 5-((3S)-3-(2-(((R)-1-(4-fluoronaphthalen-1-yl)ethyl)amino)ethyl)-1,2,3,4-tetrahydronaphthalen-1-yl)-2-methylbenzoate

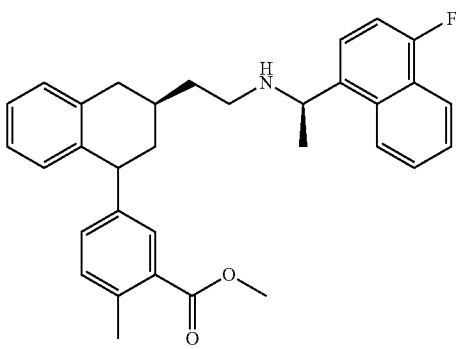 [SMILES: COC(=O)c1cc(C2C[C@H](CCN[C@H](C)c3ccc(F)c4ccccc34)Cc3ccccc32)ccc1C]

The title compound was prepared by following the similar procedure as described in Step-1 to Step-3 of Example-1 in

Example-25

5-((3S)-3-(2-(((R)-1-(4-Fluoronaphthalen-1-yl)ethyl)amino)ethyl)-1,2,3,4-tetrahydronaphthalen-1-yl)-2-methylbenzoic acid hydrochloride

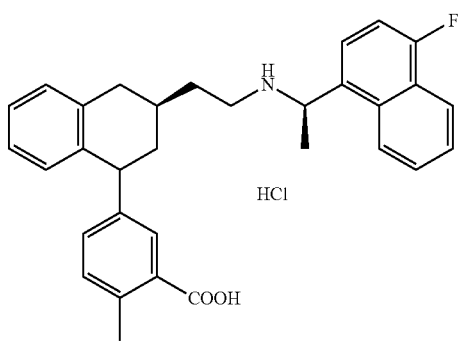 [SMILES: Cc1ccc(C2C[C@H](CCN[C@H](C)c3ccc(F)c4ccccc34)Cc3ccccc32)cc1C(=O)O ; Cl]

The title compound was prepared by following the similar ester hydrolysis procedure as described in Example-2a by taking corresponding ester Example-24 given in Table-11. Further, hydrochloride salt of these compounds was prepared by following the similar hydrochloride salt procedure as described in Example-2a.

$^1$H NMR (400 MHz, DMSO): δ12.80 (bs, 1H), 9.61 (bs, 1H), 9.12 (bs, 1H), 8.33 (d, J=8.4 Hz, 1H), 8.13 (d, J=7.6 Hz, 1H), 7.95 (m, 1H), 7.77-7.69 (m, 2H), 7.58 (S, 1H), 7.53-7.48 (m, 1H), 7.23 (d, J=8.0 Hz, 2H), 7.10 (m, 2H), 6.98-6.96 (m, 1H), 6.56 (d, J=8.0 Hz, 1H), 5.29 (m, 1H), 4.07-4.03 (m, 1H), 3.15 (m, 1H), 2.93-2.81 (m, 2H), 2.60-2.50 (m, 2H), 2.46 (S, 3H), 1.75-1.66 (m, 4H), 1.66 (d, J=6.4 Hz, 3H); m/z 481.6.

Example-26a, 26b

Methyl 2-methyl-5-((3S)-3-(2-(((R)-1-(naphthalen-1-yl)ethyl)amino)ethyl)-1,2,3,4-tetrahydronaphthalen-1-yl)benzoate

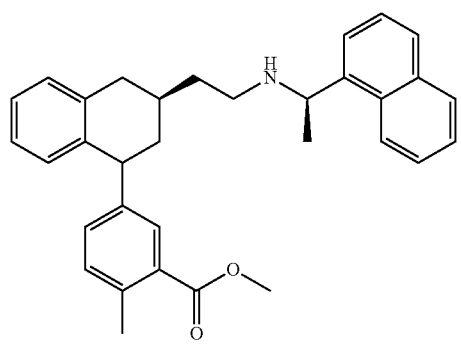 [SMILES: COC(=O)c1cc(C2C[C@H](CCN[C@H](C)c3cccc4ccccc34)Cc3ccccc32)ccc1C]

The title compound was prepared by following the similar procedure as described in Step-1 to Step-3 of Example-1 in sequential manner by taking Intermediate-7 and (3-(methoxycarbonyl)-4-methylphenyl)boronic acid.

The two diastereomers were separated by chiral preparative HPLC [CHIRAL PAK IA 250 mm×4.6, 5μ; A=n-hexane: IPA (90:10% v/v, 0.1% DEA), B=IPA; A:B=95/5% V/V; Flow=1.0 ml/min] Isomer 'a': $t_R$=8.8, Isomer 'b': $t_R$=11.35; m/z, 477.8. ($t_R$ is retention time).

Example-27a, 27b

2-Methyl-5-((3S)-3-(2-(((R)-1-(naphthalen-1-yl)ethyl)amino)ethyl)-1,2,3,4-tetrahydronaphthalen-1-yl)benzoic acid hydrochloride

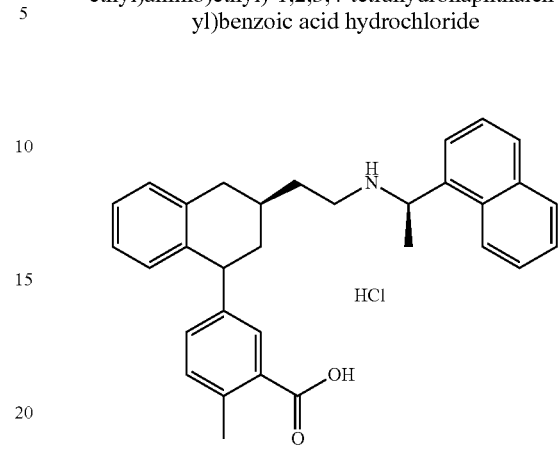

The title compounds of Example-27a, 27b and its isomers were prepared by following the similar ester hydrolysis procedure as described in Example-2a by taking ester compound of Example-26a and Example-26b. Further, hydrochloride salt of these compounds was prepared by following the similar hydrochloride salt procedure as described in Example-2a.

27a: $^1$H NMR (400 MHz, DMSO): δ 12.81 (bs, 1H), 9.87 (bs, 1H), 9.25 (bs, 1H), 8.26 (d, J=8.4 Hz, 1H), 8.03-7.97 (m, 3H), 7.65-7.56 (m, 4H), 7.24-7.19 (m, 2H), 7.10-7.05 (m, 2H), 6.97 (m, 1H), 6.57 (d, J=8.0 Hz, 1H), 5.32 (m, 1H), 4.07-4.03 (m, 1H), 3.15 (m, 1H), 2.97-2.79 (m, 2H), 2.62-2.60 (m, 2H), 2.46 (S, 3H), 1.73-1.71 (m, 4H), 1.68 (d, J=6.4 Hz, 3H); m/z 463.6.

27b: $^1$H NMR (400 MHz, DMSO): δ 12.79 (bs, 1H), 9.73 (bs, 1H), 9.09 (bs, 1H), 8.26 (d, J=8.4 Hz, 1H), 8.02-7.93 (m, 3H), 7.65-7.57 (m, 4H), 7.25-7.21 (m, 2H), 7.08-7.07 (m, 2H), 7.01-6.96 (m, 1H), 6.58 (d, J=7.6 Hz, 1H), 5.33 (m, 1H), 4.10-4.09 (m, 1H), 3.15 (m, 1H), 2.97-2.79 (m, 2H), 2.62-2.60 (m, 2H), 2.49 (S, 3H), 1.73-1.71 (m, 4H), 1.67 (d, J=6.4 Hz, 3H); m/z 463.6

Example-28

Methyl 5-((3S)-3-(3-(((R)-1-(4-fluoronaphthalen-1-yl)ethyl)amino)propyl)-1,2,3,4-tetrahydronaphthalen-1-yl)-2-methylbenzoate

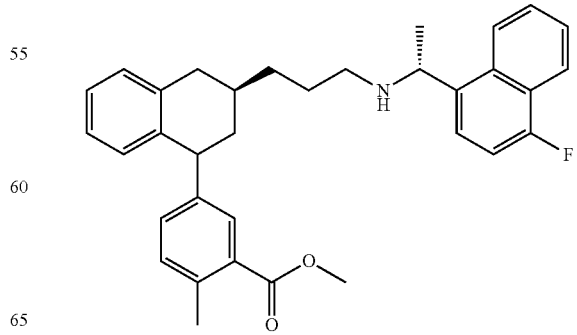

The title compound was prepared by following the similar procedure as described in Step-1 to Step-3 of Example-1 in sequential manner by taking Intermediate-8 and (3-(methoxycarbonyl)-4-methylphenyl)boronic acid; m/z 510.1

Example-29

5-((3S)-3-(3-(((R)-1-(4-fluoronaphthalen-1-yl)ethyl)amino)propyl)-1,2,3,4-tetrahydronaphthalen-1-yl)-2-methylbenzoic acid hydrochloride

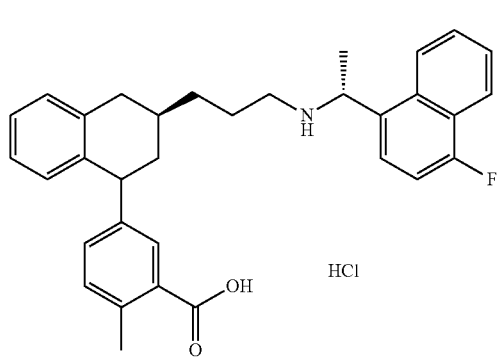 [SMILES: Cc1ccc(C2C[C@H](CCCN[C@H](C)c3ccc(F)c4ccccc34)Cc3ccccc32)cc1C(=O)O ; Cl]

The title compound was prepared by following the similar ester hydrolysis procedure as described in Example-2a by taking corresponding ester compound of Example-28. Further, hydrochloride salt was prepared by following the similar hydrochloride salt procedure as described in Example-2a.

$^1$H NMR (400 MHz, DMSO): δ 12.80 (bs, 1H), 9.46 (bs, 1H), 9.04 (bs, 1H), 8.28 (d, J=8 Hz, 1H), 8.12 (d, J=7.6 Hz, 1H), 7.79-7.68 (m, 3H), 7.55 (m, 1H), 7.49-7.44 (m, 1H), 7.25-7.20 (m, 2H), 7.09-7.07 (m, 2H), 6.99-6.95 (m, 1H), 6.55 (d, J=7.6 Hz, 1H), 5.28 (q, J=6.8 Hz, 1H), 4.06-4.02 (m, 1H), 3.14-2.97 (m, 1H), 2.84-2.77 (m, 2H), 2.47 (s, 3H), 1.98-1.96 (m, 1H), 1.71-1.68 (m, 3H), 1.64 (d, J=6.8 Hz, 3H), 1.43-1.30 (m, 3H), 1.21 (m, 1H); m/z 496.49

Example-30

Methyl 2-methyl-5-((3R)-3-(3-(((R)-1-(naphthalen-1-yl)ethyl)amino)propyl)-1,2,3,4-tetrahydronaphthalen-1-yl)benzoate

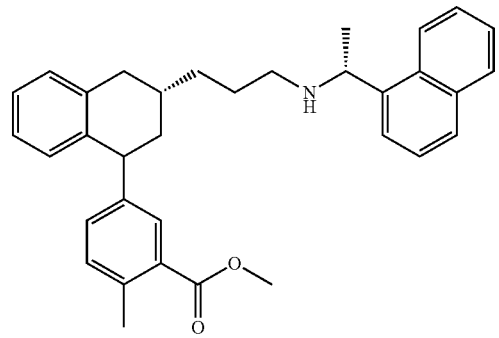 [SMILES: COC(=O)c1cc(C2C[C@@H](CCCN[C@H](C)c3cccc4ccccc34)Cc3ccccc32)ccc1C]

The title compound was prepared by following the similar procedure as described in Step-1 to Step-3 of Example-1 in sequential manner by taking Intermediate-9 and (3-(methoxycarbonyl)-4-methylphenyl)boronic acid; m/z 492.0.

Example-31

2-Methyl-5-((3R)-3-(3-(((R)-1-(naphthalen-1-yl)ethyl)amino)propyl)-1,2,3,4-tetrahydronaphthalen-1-yl)benzoic acid hydrochloride

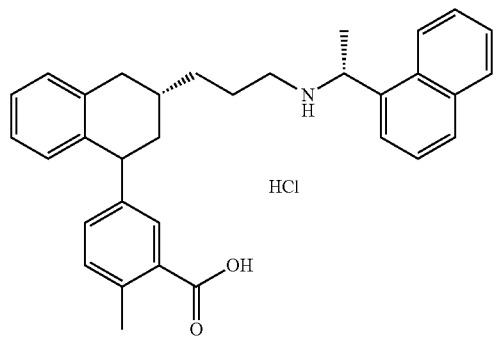 [SMILES: Cc1ccc(C2C[C@@H](CCCN[C@H](C)c3cccc4ccccc34)Cc3ccccc32)cc1C(=O)O ; Cl]

The title compound was prepared by following the similar ester hydrolysis procedure as described in Example-2a by taking corresponding Example-30. Further, hydrochloride salt was prepared by following the similar hydrochloride salt procedure as described in Example-2a $^1$H NMR (400 MHz, DMSO): δ 12.80 (bs, 1H), 9.74 (bs, 1H), 9.16 (bs, 1H), 8.27 (d, J=8.4 Hz, 1H), 8.02-7.95 (m, 3H), 7.64-7.7.56 (m, 4H), 7.25-7.20 (m, 2H), 7.07 (d, J=8 Hz, 2H), 7.00-6.96 (m, 1H), 6.57 (d, J=7.6 Hz, 1H), 5.31 (q, J=6.8 Hz, 1H), 4.08-4.07 (m, 1H), 2.98 (m, 1H), 2.81-2.78 (m, 2H), 2.45 (s, 3H), 1.98-1.96 (m, 1H), 1.77-1.75 (m, 3H), 1.67 (d, J=6.8 Hz, 3H), 1.41-1.23 (m, 3H), 1.10-1.07 (m, 1H); m/z 477.7.

Example-32

Methyl 5-((3S)-3-(3-(((R)-1-(4-fluoro-3-methoxyphenyl)ethyl)amino)propyl)-1,2,3,4-tetrahydronaphthalen-1-yl)-2-methylbenzoate

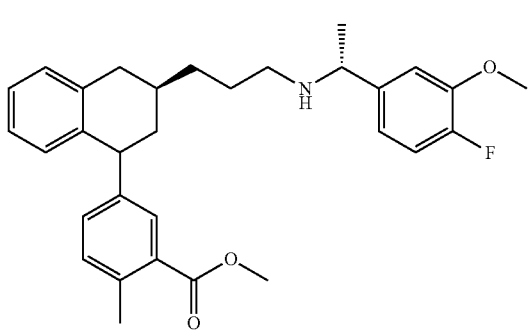 [SMILES: COC(=O)c1cc(C2C[C@H](CCCN[C@H](C)c3ccc(F)c(OC)c3)Cc3ccccc32)ccc1C]

The title compound was prepared by following the similar procedure as described in Step-1 to Step-3 of Example-1 in sequential manner by taking Intermediate-10 and (3-(methoxycarbonyl)-4-methylphenyl)boronic acid; m/z 490.

Example-33

5-((3S)-3-(3-(((R)-1-(4-Fluoro-3-methoxyphenyl)ethyl)amino)propyl)-1,2,3,4-tetrahydronaphthalen-1-yl)-2-methylbenzoic acid hydrochloride

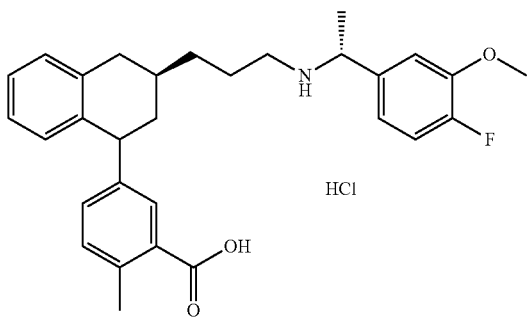 [SMILES: COc1cc([C@@H](C)NCCC[C@@H]2Cc3ccccc3C(c3ccc(C)c(C(=O)O)c3)C2)ccc1F ; Cl]

The title compound was prepared by following the similar ester hydrolysis procedure as described in Example-2a by taking corresponding Example-32. Further, hydrochloride salt was prepared by following the similar hydrochloride salt procedure as described in Example-2a. $^1$H NMR (400 MHz, DMSO): δ 12.79 (bs, 1H), 9.51 (bs, 1H), 9.24 (bs, 1H), 7.59 (m, 1H), 7.57-7.54 (m, 1H), 7.28-7.23 (m, 3H), 7.11-7.06 (m, 3H), 7.00-6.96 (m, 1H), 6.58-6.55 (m, 1H), 4.35 (m, 1H), 4.10-4.06 (m, 1H), 3.85 (s, 3H), 2.85-2.18 (m, 2H), 2.67-2.56 (m, 2H), 2.02-2.00 (m, 1H), 1.75-1.72 (m, 3H), 1.57 (d, J=6.8 Hz, 3H), 1.47-1.40 (m, 1H), 1.36-1.31 (m, 2H), 1.27-1.23 (m, 2H), 1.10-1.02 (m, 1H); m/z 476.48

Similarly, the below examples 34 to 56 given in Table-3 can also be prepared by following the similar procedure as described in herein above.

TABLE 3

| Ex. No. | Name |
|---|---|
| 34 | 2-Methyl-3-(3-((((R)-1-(naphthalen-1-yl)ethyl)amino)methyl)-1,2,3,4-tetrahydronaphthalen-1-yl)benzoic acid hydrochloride |
| 35 | 2,4-Dimethyl-5-(3-((((R)-1-(naphthalen-1-yl)ethyl)amino)methyl)-1,2,3,4-tetrahydronaphthalen-1-yl)benzoic acid hydrochloride |
| 36 | 2-Fluoro-3-(3-((((R)-1-(naphthalen-1-yl)ethyl)amino)methyl)-1,2,3,4-tetrahydronaphthalen-1-yl)benzoic acid hydrochloride |
| 37 | 4-Fluoro-3-(3-((((R)-1-(naphthalen-1-yl)ethyl)amino)methyl)-1,2,3,4-tetrahydronaphthalen-1-yl)benzoic acid hydrochloride |
| 38 | 2,3-Dimethyl-5-(3-((((R)-1-(naphthalen-1-yl)ethyl)amino)methyl)-1,2,3,4-tetrahydronaphthalen-1-yl)benzoic acid hydrochloride |
| 39 | 2-(3-(3-((((R)-1-(naphthalen-1-yl)ethyl)amino)methyl)-1,2,3,4-tetrahydronaphthalen-1-yl)benzamido)acetic acid hydrochloride |
| 40 | 2-Fluoro-5-(3-(2-(((R)-1-(naphthalen-1-yl)ethyl)amino)ethyl)-1,2,3,4-tetrahydronaphthalen-1-yl)benzoic acid hydrochloride |
| 41 | 3-Methyl-5-(3-(2-(((R)-1-(naphthalen-1-yl)ethyl)amino)ethyl)-1,2,3,4-tetrahydronaphthalen-1-yl)benzoic acid hydrochloride |
| 42 | 2,6-Dimethyl-3-(3-(2-(((R)-1-(naphthalen-1-yl)ethyl)amino) ethyl)-1,2,3,4-tetrahydro naphthalen-1-yl)benzoic acid hydrochloride |
| 43 | 2-Methyl-3-(3-(2-(((R)-1-(naphthalen-1-yl)ethyl)amino)ethyl)-1,2,3,4-tetrahydronaphthalen-1-yl)benzoic acid hydrochloride |
| 44 | 4-Methyl-3-(3-(2-(((R)-1-(naphthalen-1-yl)ethyl)amino)ethyl)-1,2,3,4-tetrahydronaphthalen-1-yl)benzoic acid hydrochloride |
| 45 | 2,4-Dimethyl-5-(3-(2-(((R)-1-(naphthalen-1-yl)ethyl)amino)ethyl)-1,2,3,4-tetrahydronaphthalen-1-yl)benzoic acid hydrochloride |
| 46 | 2-Methyl-4-(3-(2-(((R)-1-(naphthalen-1-yl)ethyl)amino)ethyl)-1,2,3,4-tetrahydronaphthalen-1-yl)benzoic acid hydrochloride |

TABLE 3-continued

| Ex. No. | Name |
|---|---|
| 47 | 5-(3-(2-(((R)-1-(4-Fluoro-3-methoxyphenyl)ethyl)amino)ethyl)-1,2,3,4-tetrahydronaphthalen-1-yl)-2-methylbenzoic acid hydrochloride |
| 48 | 2,3-Dimethyl-5-(3-(2-(((R)-1-(naphthalen-1-yl)ethyl)amino)ethyl)-1,2,3,4-tetrahydronaphthalen-1-yl)benzoic acid hydrochloride |
| 49 | 3-Methyl-5-(3-(3-(((R)-1-(naphthalen-1-yl)ethyl)amino)propyl)-1,2,3,4-tetrahydronaphthalen-1-yl)benzoic acid hydrochloride |
| 50 | 2,6-Dimethyl-3-(3-(3-(((R)-1-(naphthalen-1-yl)ethyl)amino)propyl)-1,2,3,4-tetrahydronaphthalen-1-yl)benzoic acid hydrochloride |
| 51 | 2-Methyl-3-(3-(3-(((R)-1-(naphthalen-1-yl)ethyl)amino)propyl)-1,2,3,4-tetrahydronaphthalen-1-yl)benzoic acid hydrochloride |
| 52 | 4-Methyl-3-(3-(3-(((R)-1-(naphthalen-1-yl)ethyl)amino)propyl)-1,2,3,4-tetrahydronaphthalen-1-yl)benzoic acid hydrochloride |
| 53 | 2,4-Dimethyl-5-(3-(3-(((R)-1-(naphthalen-1-yl)ethyl)amino)propyl)-1,2,3,4-tetrahydronaphthalen-1-yl)benzoic acid hydrochloride |
| 54 | 2-Methyl-4-(3-(3-(((R)-1-(naphthalen-1-yl)ethyl)amino)propyl)-1,2,3,4-tetrahydronaphthalen-1-yl)benzoic acid hydrochloride |
| 55 | 5-(3-(3-(((R)-1-(4-Fluoro-3-methoxyphenyl)ethyl)amino)propy1)-1,2,3,4-tetrahydronaphthalen-1-yl)-2-methylbenzoic acid hydrochloride |
| 56 | 2,3-Dimethyl-5-(3-(3-(((R)-1-(naphthalen-1-yl)ethyl)amino)propyl)-1,2,3,4-tetrahydronaphthalen-1-yl)benzoic acid hydrochloride |

Example-57a, 57b

Methyl 2-methyl-5-(3-((((R)-1-(naphthalen-1-yl)ethyl)amino)methyl)-3,4-dihydroquinolin-1(2H)-yl)benzoate

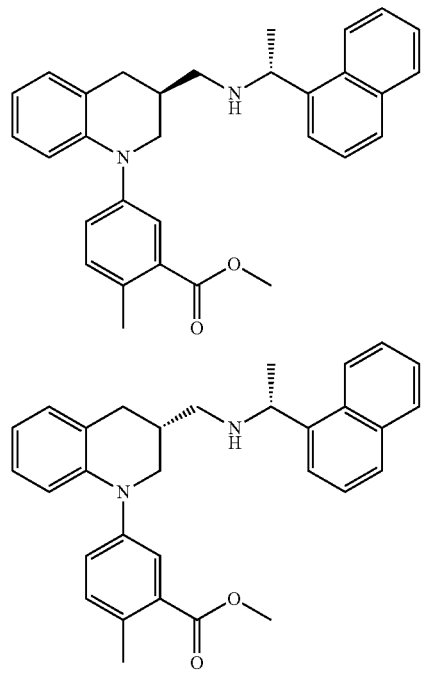

To a suspension of Intermediate-14a (400 mg, 1.264 mmol) in dry toluene (10 mL) under nitrogen atmosphere in sealed tube, methyl 5-bromo-2-methylbenzoate (347 mg, 1.517 mmol) and cesium carbonate (618 mg, 1.896 mmol) was added. The reaction mixture was stirred for 10 minutes under nitrogen atmosphere at RT. To this reaction mixture tris (dibenzylideneacetone)dipalladium (0) (57.9 mg, 0.063 mmol) and bis(tri-t-butylphosphine)palladium (0) (64.6 mg, 0.126 mmol) were added and stirred for another 20 minutes under nitrogen atmosphere. The reaction mixture was heated to reflux and maintained overnight. After completion of reaction, solvent was removed and the resultant crude compound was purified by flash chromatography by using 20% ethyl acetate in hexane to get isomer-1a (RT-8.61) 180 mg, isomer-1b (RT-9.72) 80 mg. m/z-465.1;

Example-57a: $^1$H NMR (400 MHz, DMSO-$d_6$): δ 8.17 (d, J=8 Hz, 1H), 7.88-7.86 (m, 1H), 7.77-7.74 (m, 2H), 7.66-7.63 (m, 1H), 7.50-7.43 (m, 3H), 7.27-7.21 (m, 2H), 7.02 (d, J=7.2 Hz, 1H), 6.93-6.90 (m, 2H), 6.71-6.64 (m, 1H), 4.60 (m, 1H), 3.89 (s, 3H), 3.83-3.79 (m, 1H), 3.36-3.31 (m, 1H), 2.95-2.91 (m, 1H), 2.73-2.68 (m, 1H), 2.59-2.53 (m, 5H), 1.52 (d, J=6.8 Hz, 3H).

Similarly, Example-57b was prepared by following the similar procedure as described in Example-57a by taking Intermediate-14b.

$^1$HNMR (400 MHz, DMSO-$d_6$): δ 8.16 (d, J=9.2 Hz, 1H), 7.88-7.86 (m, 1H), 7.76-7.73 (m, 2H), 7.63 (d, J=7.2 Hz, 1H), 7.50-7.44 (m, 5H), 7.25-7.20 (m, 1H), 7.05 (d, J=7.6 Hz, 1H), 6.93-6.91 (m, 1H), 6.73-6.64 (m, 1H), 4.61-4.56 (m, 1H), 3.87 (s, 3H), 3.71-3.66 (m, 1H), 3.50-3.34 (m, 1H), 3.69-3.62 (m, 1H), 2.69-2.53 (m, 6H), 1.62 (d, J=6.8 Hz, 3H).

The below Examples-58 to 68 given Table-4 were prepared by following the similar procedures as described in Example-57a,57b by taking any of corresponding intermediates 14a, 14b, 16, 17, 18, 23, 28 and 29 with appropriately substituted halo phenyl ester.

The below Examples-58,59 and 62 given Table-4 were prepared by following the similar procedures as described in Example-57a,57b by taking any of corresponding intermediates 14a,14b.

Further, two diastereomers of Example-60 was separated by using following chiral preparative HPLC method. Column: CELLULOSE 1, 250×4.6 5 u; Mobile Phase: A: Hexane/IPA (95:5% v/v, 0.1% DEA) B=MEOH_ETOH 1:1 A:B=95/5% V/V Further, two diastereomers of Example-61, 64 to 66 were separated by using following chiral preparative HPLC method. Column: CHIRAL PAK IA, 250 mm×4.65µ; Mobile Phase: A=n-hexane: IPA (90:10% v/v, 0.1% DEA), B=IPA, A=100%.

Further two diastereomers of Example-67 was separated by using chiral preparative HPLC method. Column: CHIRAL IB 250×4.6 5 u; Mobile Phase: A=(n-Hexane/IPA, 90/10, 0.1% DEA), B=IPA A:B=85/15% V/V.

Further two diastereomer of Example-63 and 68 were separated by using chiral preparative HPLC method. Column: CHIRAL CEL OJ-H 250×4.6 MM; Column: Mobile Phase: methanol_0.1% DEA_90_10% ACN.

TABLE 4

| Ex. No. | Structure | Mass (m/z) |
|---|---|---|
| 58a, 58b | 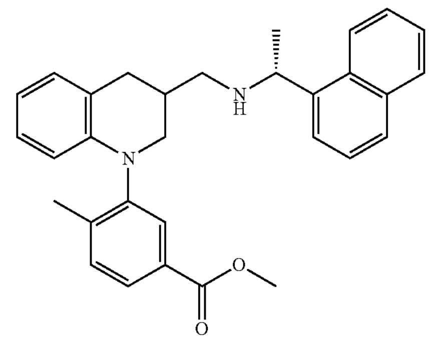 [SMILES: COC(=O)c1ccc(C)c(N2CC(CN[C@H](C)c3cccc4ccccc34)Cc3ccccc32)c1] | 465.42 |
| 59a, 59b | 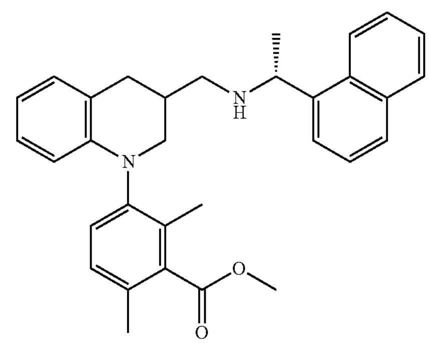 [SMILES: COC(=O)c1c(C)ccc(N2CC(CN[C@H](C)c3cccc4ccccc34)Cc3ccccc32)c1C] | 479 |
| 60a, 60b | 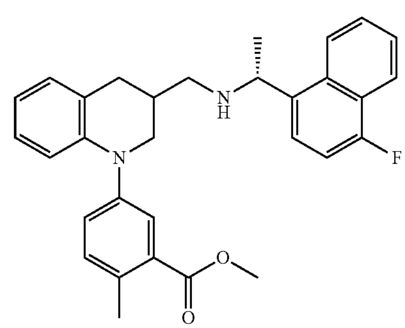 [SMILES: COC(=O)c1cc(N2CC(CN[C@H](C)c3ccc(F)c4ccccc34)Cc3ccccc32)ccc1C] | 483.11 |
| 61a, 61b | 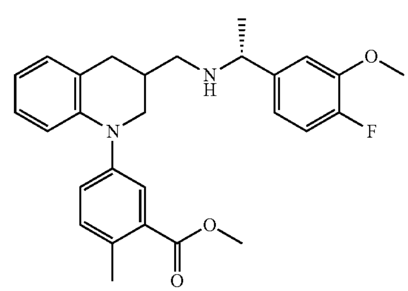 [SMILES: COC(=O)c1cc(N2CC(CN[C@H](C)c3ccc(F)c(OC)c3)Cc3ccccc32)ccc1C] | 463.1 |

TABLE 4-continued
| Ex. No. | Structure | Mass (m/z) |
|---|---|---|
| 62a, 62b | 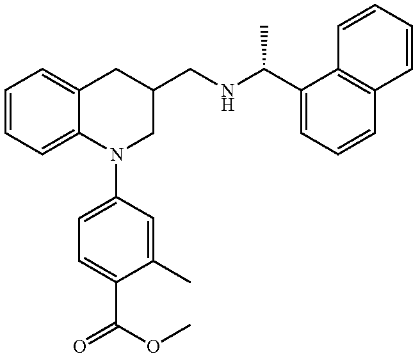 [SMILES: COC(=O)c1ccc(N2CC(CN[C@H](C)c3cccc4ccccc34)Cc3ccccc32)cc1C] | 465.42 |
| 63a, 63b | 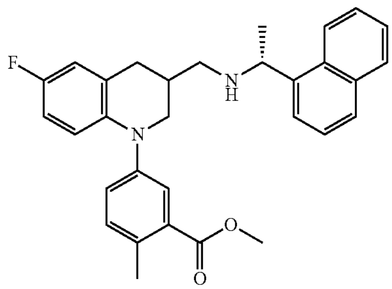 [SMILES: COC(=O)c1cc(N2CC(CN[C@H](C)c3cccc4ccccc34)Cc3cc(F)ccc32)ccc1C] | 483 |
| 64a, 64b | 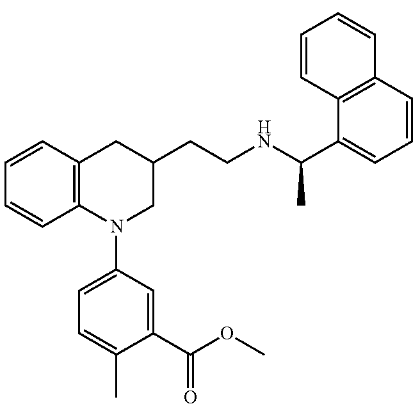 [SMILES: COC(=O)c1cc(N2CC(CCN[C@H](C)c3cccc4ccccc34)Cc3ccccc32)ccc1C] | 478.8 |
| 65a, 65b | 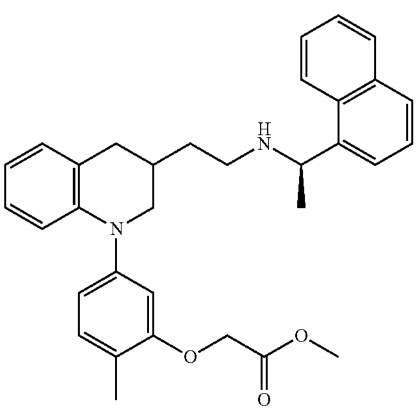 [SMILES: COC(=O)COc1cc(N2CC(CCN[C@H](C)c3cccc4ccccc34)Cc3ccccc32)ccc1C] | 509.56 |
| 66a, 66b | | 493 |
| 67a, 67b | | 496.7 |
| 68a, 68b | | 523.57 |
Example-69a,69b
2-Methyl-5-(3-((((R)-1-(naphthalen-1-yl)ethyl)amino)methyl)-3,4-dihydroquinolin-1(2H)-yl)benzoic acid hydrochloride
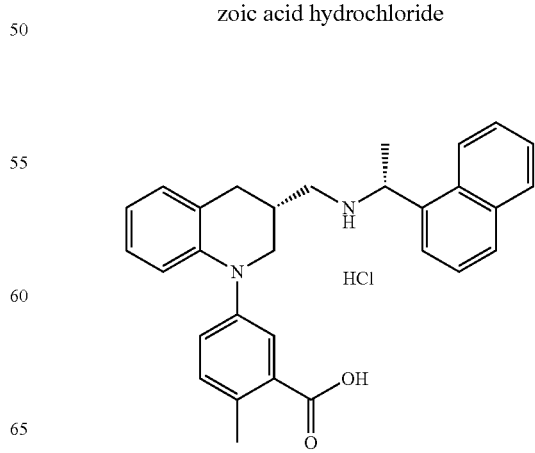

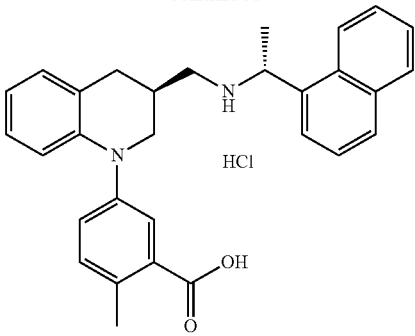

To a mixture of Example-57a (180 mg, 0.387 mmol) in tetrahydrofuran (5 mL), water (1 mL) MeOH (2 mL), LiOH (46.4 mg, 1.937 mmol) was added. The reaction mixture was heated to 80° C. and maintained for 5 h. The progress of reaction was monitored by TLC.

After completion of reaction mixture was distilled off under vacuum. The reaction mixture was cooled to 0° C. and acidified with dilute HCl solution [pH=3 to 4]. The product was extracted with Ethyl acetate, and the organic layer washed with water followed by brine solution, dried over anhydrous sodium sulfate and concentrated under vacuum to get solid compound. To this free base compound etheral HCl (2 mL) was added and stirred for 10 minutes. The solvent was removed to get solid material; then washed with n-pentane (2 mL) and dried under vacuum to get the desired compound of Example-69a (90 mg, 51.6% yield).

m/z-450.7; $^1$HNMR (400 MHz, DMSO-$d_6$): δ12.9 (bs, 1H), 9.78 (bs, 1H), 9.30 (bs, 1H), 8.16 (d, J=9.2 Hz, 1H), 8.0-7.96 (m, 3H), 7.62-7.56 (m, 4H), 7.29-7.24 (m, 2H), 7.00 (d, J=6.8 Hz, 1H), 6.91-6.87 (m, 1H), 6.68-6.64 (m, 1H), 6.53 (d, J=8.4 Hz, 1H), 5.36-5.31 (m, 1H), 4.61-4.56 (m, 1H), 3.71-3.66 (m, 1H), 3.50-3.34 (m, 1H), 3.62-2.96 (m, 1H), 2.69-2.53 (m, 6H), 1.62 (d, J=6.8 Hz, 3H).

Similarly, Example-69b was prepared by taking Example-57b by following the similar procedure as described above.

m/z-450.7; $^1$H NMR (400 MHz, DMSO-$d_6$): $^1$HNMR (400 MHz, DMSO-$d_6$): δ 13.0 (bs, 1H), 10.05 (bs, 1H), 9.29 (bs, 1H), 8.20 (d, J=8.4 Hz, 1H), 8.03-7.95 (m, 3H), 7.63-7.56 (m, 4H), 7.31-7.24 (m, 2H), 6.98 (d, J=6.8 Hz 1H), 6.89-6.85 (m, 1H), 6.66-6.62 (m, 1H), 6.49 (d, J=8.4 Hz, 1H), 5.34-5.31 (m, 1H), 3.86-3.83 (m, 1H), 3.40-3.29 (m, 4H), 3.16-3.01 (m, 1H), 2.96-2.93 (m, 1H), 2.83-2.80 (m, 1H), 2.67-2.61 (m, 2H), 1.69 (d, J=6.8 Hz, 3H).

The below Examples-70 to 80 given Table-5 were prepared by following the similar procedure as described in Example-69a. Similarly hydrochloride salts were prepared by following the similar procedure as mentioned in Example-69a.

TABLE 5

| Ex. No. | Structure | Ester | Mass (m/z) and $^1$H NMR |
|---|---|---|---|
| 70a, 70b | 4-Methyl-3-(3-((((R)-1-(naphthalen-1-yl)ethyl)amino)methyl-3,4-dihydro quinolin-1(2H)-yl)benzoic acid hydrochloride | 58a, 58b | 70a: m/z-451.1; $^1$HNMR (400 MHz, DMSO-$d_6$): δ 12.97 (bs, 1H), 9.76 (bs, 1H), 9.19 (bs, 1H), 8.16 (d, J = 9.2 Hz, 1H), 8.0-7.97 (m, 3H), 7.80-7.70 (m, 1H), 7.64-6.47 (m, 3H), 7.43-7.41 (m, 1H), 7.00 (d, J = 6.8 Hz 1H), 6.84-6.82 (m, 1H), 6.66-6.57 (m, 1H), 5.86-5.81 (m, 1H), 5.38-5.35 (m, 1H), 5.36-5.31 (m, 1H), 4.61-4.56 (m, 1H), 3.71-3.66 (m, 1H), 3.50-3.34 (m, 1H), 3.62-2.96 (m, 1H), 2.17 (s, 3H), 1.96 (s, 3H), 1.62 (d, J = 6.8 Hz, 3H). 70b; $^1$HNMR (400 MHz, DMSO-$d_6$): δ 12.97 (bs, 1H), 9.61 (bs, 1H), 9.20 (bs, 1H), 8.24 (d, J = 8 Hz, 1H), 8.0-7.99 (m, 3H), 7.97-7.60 (m, 5H), 7.48-7.42 (m, 1H), 6.98 (d, J = 6.8 Hz 1H), 6.87-6.81 (m, 1H), 6.60-6.56 (m, 1H), 5.87-5.83 (m, 1H), 5.37-5.36 (m, 1H), 3.62-3.60 (m, 1H), 3.69-3.64 (m, 1H), 3.50-3.34 (m, 1H), 3.61-2.94 (m, 1H), 2.17 (s, 3H), 1.96 (s, 3H), 1.62 (d, J = 6.8 Hz, 3H). |
| 71a, 71b | 2,6-Dimethyl-3-(3-((((R)-1-(naphthalen-1-yl)ethyl)amino)methyl)-3,4-dihydro quinolin-1(2H)-yl)benzoic acid hydrochloride | 59a, 59b | 71a: m/z 465.36; $^1$HNMR (400 MHz, DMSO-$d_6$): δ 13.14 (bs, 1H), 9.97 (bs, 1H), 9.37 (bs, 1H), 8.22 (d, J = 9.2 Hz, 1H), 8.0-7.87 (m, 3H), 7.63-7.55 (m, 3H), 7.17 (d, J = 8.4 Hz, 1H), 7.08-7.00 (m, 1H), 6.95 (d, J = 7.2 Hz, 1H), 6.83-6.81 (m, 1H), 6.56-6.54 (m, 1H), 5.81-5.79 (m, 1H), 5.36-5.34 (m, 1H), 4.61-4.56 (m, 1H), 3.71-3.66 (m, 1H), 3.50-3.34 (m, 1H), 3.62-2.96 (m, 1H), 2.69-2.53 (m, 6H), 2.28 (s, 3H), 1.62 (d, J = 6.8 Hz, 3H). 71b: m/z 465.3; $^1$HNMR (400 MHz, DMSO-$d_6$): δ 13.14 (bs, 1H), 9.97 (bs, 1H), 9.37 (bs, 1H), 8.22 (d, J = 9.2 Hz, 1H), 8.0-7.87 (m, 3H), 7.63-7.55 (m, 3H), 7.17 (d, J = 8.4 Hz, 1H), 7.08-7.00 (m, 1H), 6.95 (d, J = 7.2 Hz, 1H), 6.83-6.81 (m, 1H), 6.56-6.54 (m, 1H), 5.81-5.79 (m, 1H), 5.36-5.34 (m, 1H), 4.61-4.56 (m, 1H), 3.71-3.66 (m, 1H), 3.50-3.34 (m, 1H), 3.62-2.96 (m, 1H), 2.69-2.53 (m, 6H), 2.28 (s, 3H), 1.62 (d, J = 6.8 Hz, 3H). |

TABLE 5-continued

| Ex. No. | Structure | Ester | Mass (m/z) and ¹H NMR |
|---|---|---|---|
| 72a, 72b | 5-(3-((((R)-1-(4-Fluoro naphthalen-1-yl)ethyl)amino)methyl)-3,4-dihydro quinolin-1(2H)-yl)-2-methylbenzoic acid hydrochloride | 60a, 60b | 72a: m/z 469.1; ¹HNMR (400 MHz, DMSO-d$_6$): δ 12.97 (bs, 1H), 9.80 (bs, 1H), 9.29 (bs, 1H), 8.16 (d, J = 9.2 Hz, 1H), 8.14-8.12 (m, 1H), 8.03-7.0 (m, 1H), 7.72-7.69 (m, 2H), 7.60 (d, J = 2 Hz, 1H), 7.49-7.45 (m, 1H), 7.29-7.25 (m, 2H), 6.99 (d, J = 7.6 Hz, 1H), 6.89-6.87 (m, 1H), 6.68-6.64 (m, 1H), 6.52 (d, J = 8 Hz, 1H), 5.32-5.31 (m, 1H), 4.61-4.56 (m, 1H), 3.71-3.66 (m, 1H), 3.50-3.34 (m, 1H), 3.62-2.96 (m, 1H), 2.69-2.53 (m, 6H), 1.68 (d, J = 6.8 Hz, 3H)<br>72b: ¹HNMR (400 MHz, DMSO-d$_6$): δ 12.96 (bs, 1H), 9.82 (bs, 1H), 9.18 (bs, 1H), 8.29 (d, J = 9.2 Hz, 1H), 8.15-8.12 (m, 1H), 7.97-7.94 (m, 1H), 7.74-7.70 (m, 2H), 7.60 (d, J = 2 Hz, 1H), 7.48-7.45 (m, 1H), 7.31-7.25 (m, 2H), 7.00 (d, J = 7.6 Hz 1H), 6.88-6.87 (m, 1H), 6.67-6.66 (m, 1H), 6.51 (d, J = 8 Hz, 1H), 5.34-5.30 (m, 1H), 3.82-3.80 (m, 1H), 3.30-3.28 (m, 2H), 3.05-2.79 (m, 5H), 2.67-2.58 (m, 2H), 1.68 (d, J = 6.8 Hz, 3H). |
| 73a, 73b | 5-(3-((((R)-1-(4-Fluoro-3-methoxyphenyl)ethyl)amino)methyl)-3,4-dihydroquinolin-1(2H)-yl)-2-methylbenzoic acid hydrochloride | 61a, 61b | 73a: m/z 448.61; ¹HNMR (400 MHz, DMSO-d$_6$): 13.1 (bs, 1H), 9.69 (bs, 1H), 9.42 (bs, 1H), 7.61-7.58 (m, 2H), 7.30-7.20 (m, 3H), 7.11-7.08 (m, 1H), 6.99 (d, J = 7.2 Hz, 1H), 6.91-6.87 (m, 1H), 6.68-6.64 (m, 1H), 6.53 (d, J = 8 Hz, 1H), 4.37-4.33 (m, 2H), 3.84-3.79 (m, 4H), 3.31-3.26 (m, 1H), 2.96-2.87 (m, 2H), 2.61-2.44 (m, 5H), 1.62 (d, J = 6.8 Hz, 3H).<br>73b: ¹HNMR (400 MHz, DMSO-d$_6$): δ 12.96 (bs, 1H), 9.65 (bs, 1H), 9.23 (bs, 1H), 7.60 (d, J = 7.2 Hz, 1H), 7.54-7.51 (m, 1H), 7.29-7.21 (m, 3H), 7.08-7.00 (m, 2H), 6.86-6.87 (m, 1H), 6.68-6.64 (m, 1H), 6.52 (d, J = 8 Hz, 1H), 4.37-4.36 (m, 2H), 3.84-3.84 (m, 4H), 3.28-3.25 (m, 1H), 2.96-2.85 (m, 2H), 2.67-2.55 (m, 5H), 1.62 (d, J = 6.8 Hz, 3H). |
| 74a, 74b | 2-Methyl-4-(3-((((R)-1-(naphthalen-1-yl)ethyl)amino)methyl)-3,4-dihydro quinolin-1(2H)-yl)benzoic acid hydrochloride | 62a, 62b | 74a: m/z 451; ¹H NMR (400 MHz, DMSO-d$_6$): δ 10.13 (bs, 1H), 9.36 (bs, 1H), 8.18 (d, J = 7.6 Hz, 1H), 8.01-7.98 (m, 2H), 7.97-7.95 (m, 2H), 7.63-7.56 (m, 3H), 7.08-6.93 (m, 4H), 6.91-6.77 (m, 2H), 5.33-5.31 (m, 1H), 3.94-3.91 (m, 1H), 3.71-3.66 (m, 1H), 3.50-3.34 (m, 1H), 3.62-2.96 (m, 1H), 2.95-2.77 (m, 1H), 2.69-2.53 (m, 5H), 1.66 (d, J = 6.8 Hz, 3H).<br>74b: ¹HNMR (400 MHz, DMSO-d$_6$): δ 10.13 (bs, 1H), 9.42 (bs, 1H), 8.20 (d, J = 7.6 Hz, 1H), 8.05 (d, J = 7.2 Hz, 1H), 8.01-7.95 (m, 2H), 7.78 (d, J = 8.4 Hz, 1H), 7.61-7.55 (m, 3H), 7.07-6.92 (m, 4H), 6.91 (d, J = 7.6 Hz, 1H), 6.81-6.78 (m, 1H), 5.34-5.29 (m, 1H), 4.19-4.01 (m, 1H), 3.71-3.66 (m, 1H), 3.50-3.44 (m, 1H), 3.62-2.96 (m, 1H), 2.95-2.77 (m, 1H), 2.69-2.53 (m, 5H), 1.62 (d, J = 6.8 Hz, 3H). |

TABLE 5-continued

| Ex. No. | Structure | Ester | Mass (m/z) and ¹H NMR |
|---|---|---|---|
| 75a, 75b | 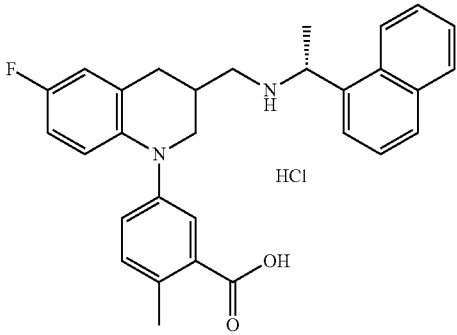<br>5-(6-Fluoro-3-((((R)-1-(naphthalen-1-yl)ethyl)amino)methyl)-3,4-dihydro quinolin-1(2H)-yl)-2-methyl benzoic acid hydrochloride | 63a, 63b | 75a: m/z 469.48; ¹HNMR (400 MHz, DMSO-$d_6$): δ 13.0 (bs, 1H), 9.98 (s, 1H), 9.36 (s, 1H), 8.20 (d, J = 7.6 Hz, 1H), 8.02-7.96 (m, 3H), 7.62-7.57 (m, 4H), 7.27-7.20 (m, 2H), 6.89-6.86 (m, 1H), 6.78-6.73 (m, 1H), 6.55-6.52 (m, 1H), 5.34-5.30 (m, 1H), 3.84-3.81 (m, 1H), 3.29-3.24 (m, 1H), 3.08-3.06 (m, 1H), 2.96-2.80 (m, 2H), 2.66-2.68 (m, 5H), 1.62 (d, J = 6.8 Hz, 3H).<br>75b: ¹HNMR (400 MHz, DMSO-d6): δ 12.93 (bs, 1H), 9.86 (s, 1H), 9.19 (bs, 1H), 8.19 (d, J = 8.0 Hz, 1H), 8.02-7.96 (m, 3H), 7.62-7.56 (m, 4H), 7.30-7.22 (m, 2H), 6.89-6.86 (m, 1H), 6.75-6.73 (m, 1H), 6.53-6.49 (m, 1H), 5.35-5.31 (m, 1H), 3.84-3.79 (m, 1H), 3.31-3.26 (m, 1H), 3.08-3.06 (m, 1H), 2.96-2.80 (m, 2H), 2.66-2.68 (m, 5H), 1.68 (d, J = 6.8 Hz, 3H). |
| 76a, 76b | 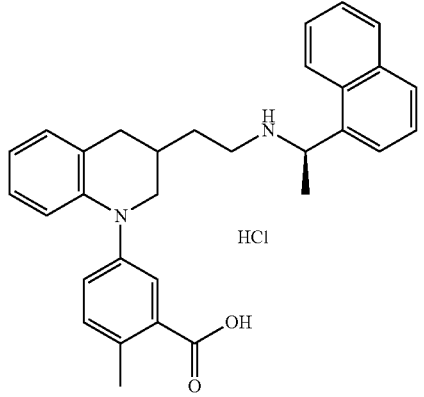<br>2-Methyl-5-(3-(2-(((R)-1-(naphthalen-1-yl)ethyl)amino)ethyl)-3,4-dihydro quinolin-1(2H)-yl)benzoic acid hydrochloride | 64a, 64b | 76a: m/z = 465.42; ¹HNMR (400 MHz, DMSO-d6): δ 12.99 (bs, 1H), 9.45 (bs, 1H), 8.99 (bs, 1H), 8.25 (d, J = 8.8 Hz, 1H), 8.01 (t, J = 7.6 Hz, 2H), 7.85 (d, J = 7.6 Hz, 1H), 7.66-7.58 (m, 4H), 7.31-7.26 (m, 2H), 7.00 (d, J = 7.2 Hz, 1H), 6.89 (d, J = 8 Hz, 1H), 6.66 (t, J = 7.2 Hz, 1H), 6.54 (t, J = 7.6 Hz, 1H), 5.33 (m, 1H), 3.59-3.55 (m, 1H), 3.22-3.19 (m, 2H), 2.93-2.83 (m, 2H), 2.52 (s, 3H), 2.07-1.95 (m, 2H), 1.75-1.73 (m, 2H), 1.67 (d, J = 6.4 Hz, 3H);<br>76b: ¹HNMR (400 MHz, DMSO-d6): δ 12.90 (bs, 1H), 9.52 (bs, 1H), 9.04 (bs, 1H), 8.23 (d, J = 8 Hz, 1H), 8.02 (t, J = 7.6 Hz, 2H), 7.99 (d, J = 7.6 Hz, 1H), 7.64-7.59 (m, 4H), 7.30-7.24 (m, 2H), 7.01 (d, J = 7.2 Hz, 1H), 6.91 (d, J = 8 Hz, 1H), 6.66 (t, J = 7.2 Hz, 1H), 6.54 (t, J = 7.6 Hz, 1H), 5.31 (m, 1H), 3.61 (m, 1H), 3.22-3.19 (m, 2H), 2.93-2.83 (m, 2H), 2.50 (s, 3H), 2.07-1.95 (m, 2H), 1.72-1.71 (m, 2H), 1.67 (d, J = 6.4 Hz, 3H). |
| 77a, 77b | 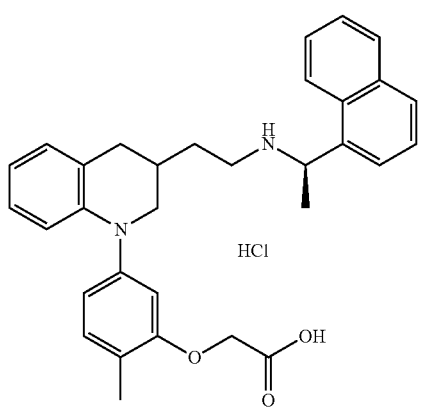<br>2-(2-methyl-5-(3-(2-(((R)-1-(naphthalen-1-yl)ethyl)amino)ethyl)-3,4-dihydroquinolin-1(2H)-yl)phenoxy)acetic acid hydrochloride | 65a, 65b | 77a: m/z = 495.49, ¹HNMR (400 MHz, DMSO-d6): δ 12.99 (bs, 1H), 9.78 (bs, 1H), 9.13 (bs, 1H), 8.24 (d, J = 8.4 Hz, 1H), 8.00 (t, J = 8.8 Hz, 2H), 7.94 (d, J = 7.2 Hz, 1H), 7.66-7.58 (m, 3H), 7.14 (d, J = 7.6 Hz, 1H), 6.96 (d, J = 7.6 Hz, 1H), 6.85 (t, J = 7.2 Hz, 1H), 6.67 (d, J = 8 Hz, 2H), 6.60 (t, J = 7.2 Hz, 1H), 6.52 (d, J = 8 Hz, 1H), 5.31-5.28 (m, 1H), 4.66 (s, 2H), 3.78 (m, 1H), 3.56-3.53 (m, 1H), 3.37-3.36 (m, 2H), 2.89-2.80 (m, 2H), 2.18 (s, 3H), 2.0 6 (m, 1H), 1.76-1.74 (m, 2H), 1.69 (d, J = 6.4 Hz, 3H);<br>77b: ¹HNMR (400 MHz, DMSO-d6): δ 12.98 (bs, 1H), 9.55 (bs, 1H), 9.04 (bs, 1H), 8.24 (d, J = 8 Hz, 1H), 8.00 (t, J = 7.6 Hz, 2H), 7.89 (d, J = 7.2 Hz, 1H), 7.65-7.58 (m, 3H), 7.14 (d, J = 7.6 Hz, 1H), 6.98 (d, J = 6.8 Hz, 1H), 6.85 (t, J = 7.2 Hz, 1H), 6.68 (d, J = 8 Hz, 2H), 6.61 (t, J = 7.2 Hz, 1H), 6.52 (d, J = 8 Hz, 1H), 5.31-5.30 (m, 1H), 4.65 (s, 2H), 3.41-3.36 (m, 2H), 3.20-3.15 (m, 2H), 2.90-2.85 (m, 3H), 2.18 (s, 3H), 1.76-1.74 (m, 2H), 1.69 (d, J = 6.4 Hz, 3H). |

TABLE 5-continued

| Ex. No. | Structure | Ester | Mass (m/z) and ¹H NMR |
|---|---|---|---|
| 78a, 78b | 2-Methyl-5-(3-(3-(((R)-1-(naphthalen-1-yl)ethyl)amino)propyl)-3,4-dihydro quinolin-1(2H)-yl)benzoic acid hydrochloride | 66a, 66b | 78a: m/z = 479.42, ¹HNMR (400 MHz, DMSO-d6): δ 12.90 (bs, 1H), 9.49 (bs, 1H), 9.04 (bs, 1H), 8.26 (d, J = 8 Hz, 1H), 8.03 (dd, J = 7.6 Hz, 1.6 Hz, 1H), 7.89 (d, J = 6.8 Hz, 1H), 7.64-7.58 (m, 3H), 7.29 (d, J = 7.6 Hz, 1H), 7.00 (d, J = 7.2 Hz, 1H), 6.90 (d, J = 6.8 Hz, 1H), 6.67 (t, J = 6.7 Hz, 2H), 6.65 (t, J = 7.2 Hz, 1H), 6.56 (d, J = 8 Hz, 2H), 5.33-5.30 (m, 1H), 3.60 (m, 1H), 3.17 (m, 1H), 3.03 (m, 1H), 2.81-2.80 (m, 1H), 2.68-2.67 (m, 2H), 2.50 (s, 3H), 1.98 (m, 1H), 1.75-1.73 (m, 2H), 1.69 (d, J = 6.4 Hz, 3H), 1.34 (m, 2H); 78b: ¹HNMR (400 MHz, DMSO-d6): δ 12.99 (bs, 1H), 9.84 (bs, 1H), 9.21 (bs, 1H), 8.24 (d, J = 8 Hz, 1H), 8.02-7.97 (m, 3H), 7.63-7.57 (m, 4H), 7.31 (d, J = 9.6 Hz, 2H), 7.01 (t, J = 7.2 Hz, 1H), 6.90 (d, J = 6.8 Hz, 1H), 6.67 (t, J = 6.8 Hz, 1H), 6.56 (d, J = 8.4 Hz, 1H), 5.28-5.27 (m, 1H), 3.58-3.56 (m, 1H), 3.39-3.37 (m, 1H), 3.20-3.15 (m, 1H), 3.03 (m, 1H), 2.85-2.81 (m, 2H), 2.50 (s, 3H), 1.98 (m, 1H), 1.75-1.72 (m, 2H), 1.67 (d, J = 6.4 Hz, 3H), 1.34-1.29 (m, 2H). |
| 79a, 79b | 3-(3-(3-(((R)-1-(4-Fluoro naphthalen-1-yl)ethyl)amino)propyl)-3,4-dihydro quinolin-1(2H)-yl)-2-methyl benzoic acid hydrochloride | 67a, 67b | 79a: m/z = 496.7; ¹HNMR (400 MHz, DMSO-d6): δ 12.99 (bs, 1H), 9.59 (bs, 1H), 9.09 (bs, 1H), 8.34 (d, J = 6.4 Hz, 1H), 8.15 (dd, J = 7.6 Hz, 1.6 Hz, 1H), 7.95-7.91 (m, 1H), 7.76-7.69 (m, 3H), 7.51 (t, J = 8.8 Hz, 1H), 7.38 (d, J = 8.8 Hz, 2H), 6.80 (t, J = 7.6 Hz, 1H), 6.96 (d, J = 7.6 Hz, 1H), 6.55 (t, J = 7.6 Hz, 1H), 5.79 (t, J = 8.4 Hz, 1H), 5.28 (m, 1H), 3.53-3.48 (m, 1H), 3.25-3.20 (m, 2H), 3.08-2.86 (m, 1H), 2.82-2.67 (m, 2H), 2.28-2.24 (m, 3H), 2.12-2.01 (m, 1H), 1.91 (m, 2H), 1.67 (d, J = 6.4 Hz, 3H), 1.36-1.34 (m, 2H); 79b: ¹HNMR (400 MHz, DMSO-d6): δ 12.98 (bs, 1H), 9.29 (bs, 1H), 9.28 (bs, 1H), 8.34 (d, J = 6.4 Hz, 1H), 8.15 (dd, J = 7.6 Hz, 1.6 Hz, 1H), 7.86-7.83 (m, 1H), 7.79-7.71 (m, 3H), 7.52 (t, J = 8.4 Hz, 1H), 7.38 (d, J = 8.8 Hz, 2H), 6.96 (t, J = 7.6 Hz, 1H), 6.80 (d, J = 7.6 Hz, 1H), 6.58 (t, J = 7.6 Hz, 1H), 5.79 (t, J = 8.4 Hz, 1H), 5.30 (m, 2H), 2.82-2.67 (m, 2H), 2.68-2.67 (m, 1H), 2.33-2.32 (m, 1H), 2.28-2.25 (m, 3H), 2.0 (m, 1H), 1.7 (m, 2H), 1.66 (d, J = 6.4 Hz, 3H), 1.36-1.34 (m, 2H), 1.23-1.22 (m, 1H). |

TABLE 5-continued

| Ex. No. | Structure | Ester | Mass (m/z) and $^1$H NMR |
|---|---|---|---|
| 80a, 80b | 2-(2-Methyl-5-(3-(3-(((R)-1-(naphthalen-1-yl)ethyl)amino)propyl)-3,4-dihydro quinolin-1(2H)-yl)phenoxy)acetic acid hydrochloride | 68a, 68b | 80a: m/z = 509.56, $^1$HNMR (400 MHz, DMSO-d6): δ 12.99 (bs, 1H), 9.65 (bs, 1H), 9.12 (bs, 1H), 8.24 (d, J = 8.4 Hz, 1H), 8.02-7.96 (m, 2H), 7.93 (d, J = 6.8 Hz, 1H), 7.65-7.58 (m, 3H), 7.14 (d, J = 7.6 Hz, 1H), 6.97 (d, J = 7.6 Hz, 1H), 6.86 (t, J = 7.2 Hz, 1H), 6.69 (d, J = 8 Hz, 2H), 6.62 (t, J = 7.2 Hz, 1H), 6.54 (d, J = 8 Hz, 1H), 5.31-5.26 (m, 1H), 4.66 (s, 2H), 3.41-3.36 (m, 2H), 3.19-3.17 (m, 1H), 2.86-2.81 (m, 1H), 2.85-2.75 (m, 2H), 2.17 (s, 3H), 1.98 (m, 1H), 1.75-1.73 (m, 2H), 1.69 (d, J = 6.4 Hz, 3H), 1.35-1.28 (m, 2H);<br>80b: $^1$HNMR (400 MHz, DMSO-d6): δ 12.98 (bs, 1H), 9.72 (bs, 1H), 9.12 (bs, 1H), 8.26 (d, J = 8.4 Hz, 1H), 8.03-7.98 (m, 2H), 7.93 (d, J = 6.8 Hz, 1H), 7.66-7.58 (m, 3H), 7.14 (d, J = 7.6 Hz, 1H), 6.95 (d, J = 7.6 Hz, 1H), 6.86 (t, J = 7.2 Hz, 1H), 6.69 (d, J = 8 Hz, 2H), 6.61 (t, J = 7.2 Hz, 1H), 6.53 (d, J = 8 Hz, 1H), 5.31-5.28 (m, 1H), 4.65 (s, 2H), 3.19-3.17 (m, 1H), 2.86-2.81 (m, 1H), 2.84-2.80 (m, 2H), 2.16 (s, 3H), 1.98 (m, 1H), 1.91 (m, 2H), 1.76-1.73 (m, 2H), 1.67 (d, J = 6.4 Hz, 3H) 1.35-1.31 (m, 2H). |

In-Vitro Pharmacological Activity

Certain illustrative compounds within the scope of the invention are screened for CaSR activity according to the procedure given below. The screening of the compounds may also be carried by other methods and procedures known to skilled in the art.

In-vitro assay method of Calcimimetics through modulation of Calcium Sensing Receptor (CaSR):

The ability of the compounds to modulate Calcium sensing receptor is determined by measuring an increase in intracellular calcium $[Ca^{2+}]_i$. Stably transfected HEK293 cells expressing hCaSR_pTriEx-3 hygro vector are developed. Cells are grown overnight on a 96-well plate to 80% confluency in Ham's F12 containing 20% FBS at 37° C., 5% $CO_2$. Subsequently, cells are washed extensively with 20 mM HEPES buffer containing 126 mM $NaCl_2$, 1 mM $MgCl_2$ and 4 mM KCl to remove serum components that might interfere with the assay. Cells are loaded with calcium sensing Fluo4NW dye in HEPES base buffer containing 0.1% BSA and 1mg/ml glucose for 30 minutes to measure changes in intracellular calcium. The activities of the compounds are measured in FLIPR using 0.3 mM $CaCl_2$ in 20 mM HEPES base buffer. The effectiveness of the compound to modulate receptor activity is determined by calculating the $EC_{50}$ responses for that compound in an 8-point assay and plotted using GraphPad Prism 5.

The compounds prepared were tested using the above assay procedure and the results obtained are given below. The $EC_{50}$ (nM) values of few representative compounds are set forth in Table-6.

The in-vitro activity data has been given in Table-6 for representative compounds.

TABLE 6

| Example number | $EC_{50}$ Range |
|---|---|
| 2a, 7a, 7b, 8a, 8b, 10a, 10b, 10c, 13b, 14b, 16a, 17, 19a, 27a, 27b, 29, 31, 69a, 71a, 73a, 75a, 77b, 78b, 79a, 79b | less than 20 nM |
| 2c, 7c, 8d, 9b, 13a, 16b, 19b, 22, 23, 25, 72b, 76b, 80b | between 20.01 to 50.00 nM |
| 2b, 8c, 9c, 14a, 70b, 73b, | between 50.01 to 200 nM |

Thus, the above in-vitro assay method shows that the compounds of the invention were found to exhibit agonistic activity for CaSR, thereby showing utility for treating diseases, disorders associated with the modulation of CaSR.

In-Vivo Activity in CKD Wistar Rats

Animals were fed with 0.75% adenine diet for a period of 28 days for development of chronic kidney disease (CKD). After measurement of plasma PTH on day 28, animals were randomized based on plasma PTH (intact PTH) levels before using them for the study. Overnight fasted animals were bled retro-orbitally to collect basal blood sample (0.5 ml). Rats were dosed orally with vehicle and with test compounds where they Formulated in PEG 300:PG:Captisol (20:15:65). Six to eight animals were used in each group then compounds of the invention were administered at 1 mg/kg dose. Post 2 h oral dosing animals were fed with feed and water ad libitum. Post treatment blood samples were collected by retro-orbital bleeding under light ether anesthesia at different time points for plasma PTH estimation. Plasma PTH was measured using sandwich ELISA kits (Immunotopics, USA). Percentage suppression of plasma PTH was calculated with respect to individual basal untreated values by using the following Formula $$\text{Percent suppression} = \frac{\text{Pre-treated individual value} - \text{Post-treated individual}}{\text{Pre-treated individual value}} \times 100$$

Thus, the above in-vivo method shows that the compounds of the invention were found to exhibit suppress plasma PTH levels, thereby showing utility for treating diseases, disorders associated with the modulation of CaSR.

The invention claimed is:
1. A compound having the Formula (I):

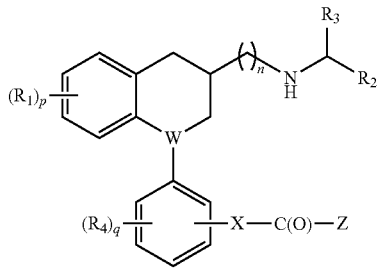

wherein,
W is CH or N;
R$_1$, which may be same or different at each occurrence, is independently selected from halogen, nitro, cyano, substituted or unsubstituted alkyl, substituted or unsubstituted haloalkyl, substituted or unsubstituted cycloalkyl, —C(O)OR$_5$, —(CR$_a$R$_b$)$_r$—C(O)OR$_5$, —O—C(O)OR$_5$, —O(CR$_a$R$_b$)$_r$—C(O)OR$_5$, —NR$_6$R$_7$, —C(O)R$_8$, —C(O)NR$_6$R$_7$, —NR$_6$C(O)R$_8$, —S(O)$_{0-2}$R$_5$, —S(O)$_2$NR$_6$R$_7$ and —NR$_6$S(O)$_2$R$_8$;
R$_2$ is substituted or unsubstituted aryl;
R$_3$ is substituted or unsubstituted alkyl;
R$_4$, which may be same or different at each occurrence, is independently selected from halogen, cyano, substituted or unsubstituted alkyl, substituted or unsubstituted haloalkyl, —OR$_5$, —NR$_6$R$_7$, —C(O)R$_8$, —C(O)NR$_6$R$_7$, —NR$_6$C(O)R$_8$, —S(O)$_{0-2}$R$_5$, —S(O)$_2$NR$_6$R$_7$ and —NR$_5$S(O)$_2$R$_8$;
X is selected from a bond, —(CR$_a$R$_b$)$_r$—, —O—, —NR$_7$—, —O(CR$_a$R$_b$)$_r$—, —C(O)NR$_7$—, —C(O)NR$_7$(CR$_a$R$_b$)$_r$—, —(CR$_a$R$_b$)$_r$cycloalkylene-, cycloalkylene, cycloalkylene-(CR$_a$R$_b$)$_r$— and —O-cycloalkylene;
R$_a$ and R$_b$, which may be same or different at each occurrence, are independently selected from hydrogen, halogen, hydroxy, cyano, substituted or unsubstituted alkyl, substituted or unsubstituted haloalkyl and substituted or unsubstituted cycloalkyl; or R$_a$ and R$_b$, together with the carbon atom to which they are attached, may form a substituted or unsubstituted 3 to 7 membered saturated carbocyclic ring;
Z is —OR$_5$ or —NR$_6$R$_7$;
R$_5$, which may be same or different at each occurrence, is independently selected from hydrogen, substituted or unsubstituted alkyl, substituted or unsubstituted haloalkyl and substituted or unsubstituted aryl;
R$_6$ and R$_7$, which may be same or different at each occurrence, are independently selected from hydrogen, substituted or unsubstituted alkyl, —(CR$_a$R$_b$)$_r$—C(O)OR$_5$, substituted or unsubstituted cycloalkyl, substituted or unsubstituted cycloalkylalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl and substituted or unsubstituted heterocyclylalkyl; or R$_6$ and R$_7$, together with the nitrogen atom to which they are attached, may form a substituted or unsubstituted, saturated or unsaturated 3 to 10 membered cyclic ring, wherein the unsaturated cyclic ring may have one or two double bonds;

R$_8$ is substituted or unsubstituted alkyl or substituted or unsubstituted aryl;
'n' is an integer ranging from 0 to 3, both inclusive;
'p' is an integer ranging from 0 to 3, both inclusive;
'q' is an integer ranging from 0 to 3, both inclusive; and
'r' is an integer ranging from 1 to 3, both inclusive;
or a pharmaceutically acceptable salt thereof.

2. The compound of claim 1 having the Formula (II):

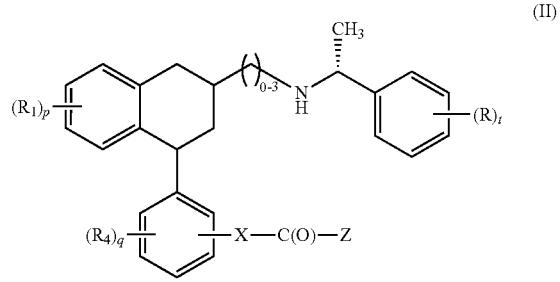

wherein,
R$_1$, R$_4$, X, Z, 'p' and 'q' are as defined in Formula (I);
R, which may be same or different at each occurrence, is independently selected from halogen, hydroxy, substituted or unsubstituted alkyl, substituted or unsubstituted haloalkyl, and substituted or unsubstituted alkoxy; and
't' is an integer ranging from 0 to 3, both inclusive;
or its pharmaceutically acceptable salt thereof.

3. The compound of claim 1 having the Formula (III):

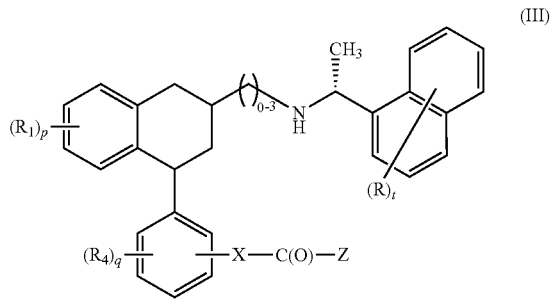

wherein,
R$_1$, R$_4$, X, Z, 'p' and 'q' are as defined in Formula (I);
R, which may be same or different at each occurrence, is independently selected from halogen, hydroxy, substituted or unsubstituted alkyl, substituted or unsubstituted haloalkyl, and substituted or unsubstituted alkoxy; and
't' is an integer ranging from 0 to 3, both inclusive;
or its pharmaceutically acceptable salt thereof.

4. The compound of claim 1 having the Formula (IV):

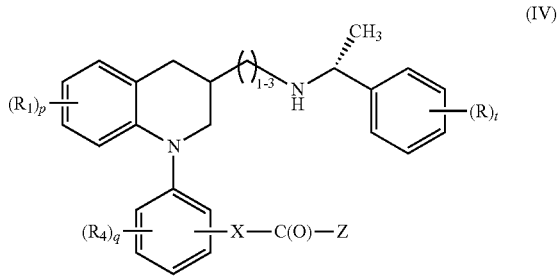

wherein, $R_1$, $R_4$, X, Z, 'p' and 'q' are as defined in Formula (I);

R, which may be same or different at each occurrence, is independently selected from halogen, hydroxy, substituted or unsubstituted alkyl, substituted or unsubstituted haloalkyl, and substituted or unsubstituted alkoxy; and 't' is an integer ranging from 0 to 3, both inclusive;

or its pharmaceutically acceptable salt thereof.

5. The compound of claim 1 having the Formula (V):

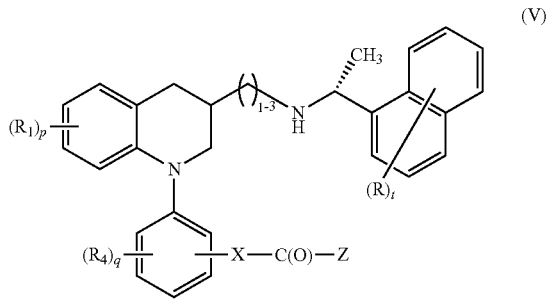

(V)

wherein, $R_1$, $R_4$, X, Z, 'p' and 'q' are as defined in Formula (I);

R, which may be same or different at each occurrence, is independently selected from halogen, hydroxy, substituted or unsubstituted alkyl, substituted or unsubstituted haloalkyl, and substituted or unsubstituted alkoxy; and 't' is an integer ranging from 0 to 3, both inclusive;

or its pharmaceutically acceptable salt thereof.

6. The compound of claim 1 wherein $R_2$ is substituted or unsubstituted phenyl or substituted or unsubstituted naphthyl; wherein the substituents are selected from halogen, hydroxy, substituted or unsubstituted alkyl, substituted or unsubstituted haloalkyl, and substituted or unsubstituted alkoxy.

7. The compound of claim 1, wherein X is bond, —($CR_aR_b)_r$—, —O—, —O($CR_aR_b)_r$—, —C(O)$NR_7$—, —C(O)$NR_7$($CR_aR_b)_r$—, —($CR_aR_b)_r$cycloalkylene-, cycloalkylene, cycloalkylene-($CR_aR_b)_r$— and —O-cycloalkylene; wherein $R_a$ and $R_b$ are independently a hydrogen or substituted or unsubstituted alkyl; $R_7$ is a hydrogen or substituted or unsubstituted alkyl; and 'r' is 1 or 2.

8. The compound of claim 1, wherein Z is —$OR_5$ where $R_5$ is hydrogen or substituted or unsubstituted alkyl.

9. The compound of claim 1 having the Formula (VI)

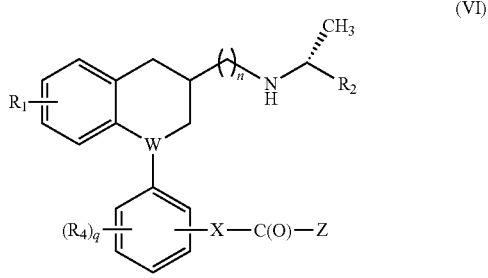

(VI)

wherein,

W is CH or N;

$R_1$ is hydrogen or halogen;

$R_2$ is substituted or unsubstituted aryl wherein the aryl is substituted or unsubstituted phenyl or substituted or unsubstituted naphthyl and the substituents are halogen or substituted or unsubstituted alkoxy;

$R_4$ is halogen, or substituted or unsubstituted alkyl;

X is selected from a bond, —$CR_aR_b$—, —O—$CR_aR_b$— and —C(O)$NR_7$—$CR_aR_b$—;

$R_a$ and $R_b$ are hydrogen, substituted or unsubstituted alkyl;

Z is —$OR_5$ or —$NR_6R_7$;

$R_5$ is hydrogen or substituted or unsubstituted alkyl;

$R_6$ and $R_7$ are independently a hydrogen or substituted or unsubstituted alkyl 'n' is an integer ranging from 0 to 3, both inclusive; and 'q' is an integer ranging from 0 to 2, both inclusive;

or a pharmaceutically acceptable salt thereof.

10. The compound of claim 1, which is selected from:

3-(3-((((R)-1-(Naphthalen-1-yl)ethyl)amino)methyl)-1,2,3,4-tetrahydronaphthalen-1-yl)benzoic acid hydrochloride, 2-Fluoro-5-(3-((((R)-1-(naphthalen-1-yl)ethyl)amino)methyl)-1,2,3,4-tetrahydronaphthalen-1-yl)benzoic acid hydrochloride, 2-Methyl-5-(3-((((R)-1-(naphthalen-1-yl)ethyl)amino)methyl)-1,2,3,4-tetrahydronaphthalen-1-yl)benzoic acid hydrochloride, 3-Methyl-5-(3-((((R)-1-(naphthalen-1-yl)ethyl)amino)methyl)-1,2,3,4-tetrahydronaphthalen-1-yl)benzoic acid hydrochloride, 2,6-Dimethyl-3-(3-((((R)-1-(naphthalen-1-yl)ethyl)amino)methyl)-1,2,3,4-tetrahydronaphthalen-1-yl)benzoic acid hydrochloride, 2-Methyl-4-((3S)-3-((((R)-1-(naphthalen-1-yl)ethyl)amino)methyl)-1,2,3,4-tetrahydronaphthalen-1-yl)benzoic acid hydrochloride, 4-Methyl-3-((3S)-3-((((R)-1-(naphthalen-1-yl)ethyl)amino)methyl)-1,2,3,4-tetrahydronaphthalen-1-yl)benzoic acid hydrochloride, 5-((3S)-3-((((R)-1-(4-Fluoro-3-methoxyphenyl)ethyl)amino)methyl)-1,2,3,4-tetrahydronaphthalen-1-yl)-2-methylbenzoic acid hydrochloride, 3-((3S)-3-((((R)-1-(4-Fluoro-3-methoxyphenyl)ethyl)amino)methyl)-1,2,3,4-tetrahydronaphthalen-1-yl)-2,6-dimethylbenzoic acid hydrochloride, 5-((3S)-3-((((R)-1-(4-Fluoronaphthalen-1-yl)ethyl)amino)methyl)-1,2,3,4-tetrahydronaphthalen-1-yl)-2-methylbenzoic acid hydrochloride, 2-Methyl-5-(3-(((R)-1-(naphthalen-1-yl)ethyl)amino)-1,2,3,4-tetrahydronaphthalen-1-yl)benzoic acid hydrochloride, 2-Methyl-4-(3-(((R)-1-(naphthalen-1-yl)ethyl)amino)-1,2,3,4-tetrahydronaphthalen-1-yl)benzoic acid hydrochloride, 5-((3S)-3-(2-(((R)-1-(4-Fluoronaphthalen-1-yl)ethyl)amino)ethyl)-1,2,3,4-tetrahydronaphthalen-1-yl)-2-methylbenzoic acid hydrochloride, 2-Methyl-5-((3S)-3-(2-(((R)-1-(naphthalen-1-yl)ethyl)amino)ethyl)-1,2,3,4-tetrahydronaphthalen-1-yl)benzoic acid hydrochloride, 5-((3S)-3-(3-(((R)-1-(4-fluoronaphthalen-1-yl)ethyl)amino)propyl)-1,2,3,4-tetrahydronaphthalen-1-yl)-2-methylbenzoic acid hydrochloride, 2-Methyl-5-((3R)-3-(3-(((R)-1-(naphthalen-1-yl)ethyl)amino)propyl)-1,2,3,4-tetrahydronaphthalen-1-yl)benzoic acid hydrochloride, 5-((3S)-3-(3-(((R)-1-(4-Fluoro-3-methoxyphenyl)ethyl)amino)propyl)-1,2,3,4-tetrahydronaphthalen-1-yl)-2-methylbenzoic acid hydrochloride, 2-Methyl-5-(3-((((R)-1-(naphthalen-1-yl)ethyl)amino) methyl)-3,4-dihydroquinolin-1(2H)-yl)benzoic acid hydrochloride, 4-Methyl-3-(3-((((R)-1-(naphthalen-1-yl)ethyl)amino) methyl)-3,4-dihydro quinolin-1(2H)-yl)benzoic acid hydrochloride, 2,6-Dimethyl-3-(3-((((R)-1-(naphthalen-1-yl)ethyl) amino)methyl)-3,4-dihydro quinolin-1(2H)-yl)benzoic acid hydrochloride, 5-(3-((((R)-1-(4-Fluoro naphthalen-1-yl)ethyl)amino) methyl)-3,4-dihydro quinolin-1(2H)-yl)-2-methylbenzoic acid hydrochloride, 5-(3-((((R)-1-(4-Fluoro-3-methoxyphenyl)ethyl)amino) methyl)-3,4-dihydroquinolin-1(2H)-yl)-2-methylbenzoic acid hydrochloride, 2-Methyl-4-(3-((((R)-1-(naphthalen-1-yl)ethyl)amino) methyl)-3,4-dihydro quinolin-1(2H)-yl)benzoic acid hydrochloride, 5-(6-Fluoro-3-((((R)-1-(naphthalen-1-yl)ethyl)amino) methyl)-3,4-dihydro quinolin-1(2H)-yl)-2-methyl benzoic acid hydrochloride, 2-Methyl-5-(3-(2-(((R)-1-(naphthalen-1-yl)ethyl)amino) ethyl)-3,4-dihydro quinolin-1(2H)-yl)benzoic acid hydrochloride, 2-(2-methyl-5-(3-(2-(((R)-1-(naphthalen-1-yl)ethyl) amino)ethyl)-3,4-dihydroquinolin-1(2H)-yl)phenoxy) acetic acid hydrochloride, 2-Methyl-5-(3-(3-(((R)-1-(naphthalen-1-yl)ethyl)amino) propyl)-3,4-dihydro quinolin-1(2H)-yl)benzoic acid hydrochloride, 3-(3-(3-(((R)-1-(4-Fluoro naphthalen-1-yl)ethyl)amino) propyl)-3,4-dihydro quinolin-1(2H)-yl)-2-methyl benzoic acid hydrochloride, 2-(2-Methyl-5-(3-(3-(((R)-1-(naphthalen-1-yl)ethyl) amino) propyl)-3,4-dihydro quinolin-1(2H)-yl)phenoxy) acetic acid hydrochloride, 2-Methyl-3-(3-((((R)-1-(naphthalen-1-yl)ethyl)amino) methyl)-1,2,3,4-tetrahydronaphthalen-1-yl)benzoic acid hydrochloride, 2,4-Dimethyl-5-(3-((((R)-1-(naphthalen-1-yl)ethyl) amino)methyl)-1,2,3,4-tetrahydronaphthalen-1-yl)benzoic acid hydrochloride, 2-Fluoro-3-(3-((((R)-1-(naphthalen-1-yl)ethyl)amino) methyl)-1,2,3,4-tetrahydronaphthalen-1-yl)benzoic acid hydrochloride, 4-Fluoro-3-(3-((((R)-1-(naphthalen-1-yl)ethyl)amino) methyl)-1,2,3,4-tetrahydronaphthalen-1-yl)benzoic acid hydrochloride, 2,3-Dimethyl-5-(3-((((R)-1-(naphthalen-1-yl)ethyl) amino)methyl)-1,2,3,4-tetrahydronaphthalen-1-yl)benzoic acid hydrochloride, 2-(3-(3-((((R)-1-(Naphthalen-1-yl)ethyl)amino)methyl)-1,2,3,4-tetrahydronaphthalen-1-yl)benzamido)acetic acid hydrochloride, 2-Fluoro-5-(3-(2-(((R)-1-(naphthalen-1-yl)ethyl)amino) ethyl)-1,2,3,4-tetrahydronaphthalen-1-yl)benzoic acid hydrochloride, 3-Methyl-5-(3-(2-(((R)-1-(naphthalen-1-yl)ethyl)amino) ethyl)-1,2,3,4-tetrahydronaphthalen-1-yl)benzoic acid hydrochloride, 2,6-Dimethyl-3-(3-(2-(((R)-1-(naphthalen-1-yl)ethyl) amino)ethyl)-1,2,3,4-tetrahydronaphthalen-1-yl)benzoic acid hydrochloride, 2-Methyl-3-(3-(2-(((R)-1-(naphthalen-1-yl)ethyl)amino) ethyl)-1,2,3,4-tetrahydronaphthalen-1-yl)benzoic acid hydrochloride, 4-Methyl-3-(3-(2-(((R)-1-(naphthalen-1-yl)ethyl)amino) ethyl)-1,2,3,4-tetrahydronaphthalen-1-yl)benzoic acid hydrochloride, 2,4-Dimethyl-5-(3-(2-(((R)-1-(naphthalen-1-yl)ethyl) amino)ethyl)-1,2,3,4-tetrahydronaphthalen-1-yl)benzoic acid hydrochloride, 2-Methyl-4-(3-(2-(((R)-1-(naphthalen-1-yl)ethyl)amino) ethyl)-1,2,3,4-tetrahydronaphthalen-1-yl)benzoic acid hydrochloride, 5-(3-(2-(((R)-1-(4-Fluoro-3-methoxyphenyl)ethyl) amino)ethyl)-1,2,3,4-tetrahydronaphthalen-1-yl)-2-methylbenzoic acid hydrochloride, 2,3-Dimethyl-5-(3-(2-(((R)-1-(naphthalen-1-yl)ethyl) amino)ethyl)-1,2,3,4-tetrahydronaphthalen-1-yl)benzoic acid hydrochloride, 3-Methyl-5-(3-(3-(((R)-1-(naphthalen-1-yl)ethyl)amino) propyl)-1,2,3,4-tetrahydronaphthalen-1-yl)benzoic acid hydrochloride, 2,6-Dimethyl-3-(3-(3-(((R)-1-(naphthalen-1-yl)ethyl) amino)propyl)-1,2,3,4-tetrahydronaphthalen-1-yl)benzoic acid hydrochloride, 2-Methyl-3-(3-(3-(((R)-1-(naphthalen-1-yl)ethyl)amino) propyl)-1,2,3,4-tetrahydronaphthalen-1-yl)benzoic acid hydrochloride, 4-Methyl-3-(3-(3-(((R)-1-(naphthalen-1-yl)ethyl)amino) propyl)-1,2,3,4-tetrahydronaphthalen-1-yl)benzoic acid hydrochloride, 2,4-Dimethyl-5-(3-(3-(((R)-1-(naphthalen-1-yl)ethyl) amino)propyl)-1,2,3,4-tetrahydronaphthalen-1-yl)benzoic acid hydrochloride, 2-Methyl-4-(3-(3-(((R)-1-(naphthalen-1-yl)ethyl)amino) propyl)-1,2,3,4-tetrahydronaphthalen-1-yl)benzoic acid hydrochloride, 5-(3-(3-(((R)-1-(4-Fluoro-3-methoxyphenyl)ethyl) amino)propyl)-1,2,3,4-tetrahydronaphthalen-1-yl)-2-methylbenzoic acid hydrochloride, 2,3-Dimethyl-5-(3-(3-(((R)-1-(naphthalen-1-yl)ethyl) amino)propyl)-1,2,3,4-tetrahydronaphthalen-1-yl)benzoic acid hydrochloride, a pharmaceutically acceptable salt thereof, or a stereoisomer thereof.

11. A pharmaceutical composition comprising one or more compounds of Formula (I) according to claim 1, and one or more pharmaceutically acceptable excipients.

12. A method of treating, managing and/or lessening the diseases or disorders, syndromes or conditions associated with the modulation of calcium sensing receptor (CaSR) in a subject in need thereof wherein the method comprises administering to the subject a therapeutically effective amount of a compound of claim 1 or a pharmaceutically acceptable salt thereof.

13. The method of claim 12, wherein the diseases, disorders, syndromes or conditions associated with the modulation of calcium sensing receptor (CaSR) are selected from hyperparathyroidism, chronic renal failure (with or without dialysis), chronic kidney disease (with or without dialysis) and their complications.

14. The method of claim 13, wherein hyperparathyroidism is primary hyperparathyroidism, secondary hyperparathyroidism or tertiary hyperparathyroidism.

15. The method of claim 12, wherein the diseases, disorders, syndromes or conditions associated with the modulation of CaSR receptors are selected from the group consisting of parathyroid adenoma, parathyroid hyperplasia, parathyroid carcinoma, vascular & valvular calcification, abnormal calcium homeostasis, hypercalcemia, abnormal phosphorous homeostasis, hypophosphatemia, bone related diseases or complications arising due to hyperparathyroidism, chronic kidney disease or parathyroid carcinoma, bone loss post renal transplantation, osteitis fibrosa cystica, adynamic bone disease, renal bone diseases, cardiovascular complications arising due to hyperparathyroidism or chronic kidney disease, certain malignancies in which $(Ca^{2+})_e$ ions are abnormally high, cardiac, renal or intestinal dysfunctions, podocyte-related diseases, abnormal intestinal motility, diarrhea, augmenting gastrin or gastric acid secretion to directly or indirectly benefit in atrophic gastritis or to improve absorption of pharmacological compounds, drugs or supplements from gastro-intestinal tract by augmenting gastric acidity.

16. A process for the preparation of compound of Formula (Ia):

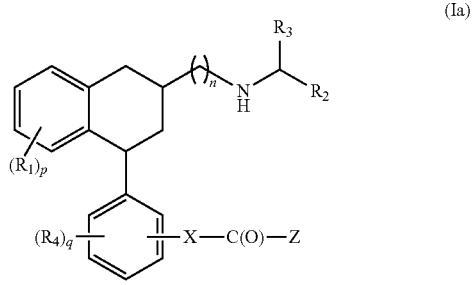

wherein, $R_1$, $R_2$, $R_3$, $R_4$, X, 'p' and 'q' are as defined in herein above;

$R_1$, which may be same or different at each occurrence, is independently selected from halogen, nitro, cyano, substituted or unsubstituted alkyl, substituted or unsubstituted haloalkyl, substituted or unsubstituted cycloalkyl, —C(O)OR$_5$, —(CR$_a$R$_b$)$_r$—C(O)OR$_5$, —O—C(O)OR$_5$, —O(CR$_a$R$_b$)$_r$—C(O)OR$_5$, —NR$_6$R$_7$, —C(O)R$_8$, —C(O)NR$_6$R$_7$, —NR$_6$C(O)R$_8$, —S(O)$_{0-2}$R$_5$, —S(O)$_2$NR$_6$R$_7$ and —NR$_6$S(O)$_2$R$_8$;

$R_2$ is substituted or unsubstituted aryl;

$R_3$ is substituted or unsubstituted alkyl;

$R_4$, which may be same or different at each occurrence, is independently selected from halogen, cyano, substituted or unsubstituted alkyl, substituted or unsubstituted haloalkyl, —OR$_5$, —NR$_6$R$_7$, —C(O)R$_8$, —C(O)NR$_6$R$_7$, —NR$_6$C(O)R$_8$, —S(O)$_{0-2}$R$_5$, —S(O)$_2$NR$_6$R$_7$ and —NR$_5$S(O)$_2$R$_8$;

X is selected from a bond, —(CR$_a$R$_b$)$_r$—, —O—, —NR$_7$—, —O(CR$_a$R$_b$)$_r$—, —C(O)NR$_7$—, —C(O)NR$_7$(CR$_a$R$_b$)$_r$—, —(CR$_a$R$_b$)$_r$cycloalkylene-, cycloalkylene, cycloalkylene-(CR$_a$R$_b$)$_r$— and —O-cycloalkylene;

$R_a$ and $R_b$, which may be same or different at each occurrence, are independently selected from hydrogen, halogen, hydroxy, cyano, substituted or unsubstituted alkyl, substituted or unsubstituted haloalkyl and substituted or unsubstituted cycloalkyl; or $R_a$ and $R_b$, together with the carbon atom to which they are attached, may form a substituted or unsubstituted 3 to 7 membered saturated carbocyclic ring;

$R_5$, which may be same or different at each occurrence, is independently selected from hydrogen, substituted or unsubstituted alkyl, substituted or unsubstituted haloalkyl and substituted or unsubstituted aryl;

$R_6$ and $R_7$, which may be same or different at each occurrence are independently selected from hydrogen, substituted or unsubstituted alkyl, —(CR$_a$R$_b$)$_r$—C(O)OR$_5$, substituted or unsubstituted cycloalkyl, substituted or unsubstituted cycloalkylalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl and substituted or unsubstituted heterocycloalkyl or $R_6$ and $R_7$, together with the nitrogen atom to which they are attached, may form a substituted or unsubstituted, saturated or unsaturated 3 to 10 membered cyclic ring, wherein the unsaturated cyclic ring may have one or two double bonds;

$R_8$ is substituted or unsubstituted alkyl or substituted or unsubstituted aryl;

'p' is an integer ranging from 0 to 3, both inclusive;

'q' is an integer ranging from 0 to 3, both inclusive; and

'r' is an integer ranging from 1 to 3, both inclusive;

or a pharmaceutically acceptable salt thereof;

the process comprising the steps:

a) converting a keto group in Formula (6a, 6b, 6c) where 'n' is 1, 2, or 3, into enol-triflate using 1,1,1-trifluoro-N-phenyl-N-((trifluoromethyl)sulfonyl)methane sulfonamide in presence of potassium bis(trimethylsilyl)amide (KHMDS) to give compound of Formula (20);

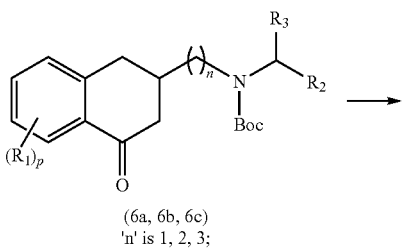

(6a, 6b, 6c)
'n' is 1, 2, 3;

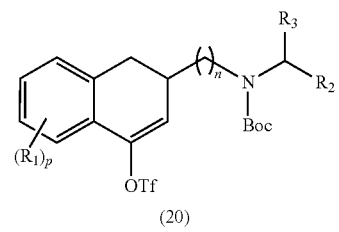

(20)

b) coupling of enol-triflate of compound of Formula (20) with suitable aryl boronic acids or aryl boronic ester in presence of a base and tetrakis(triphenylphosphine)palladium(0) to give compound of Formula (21);

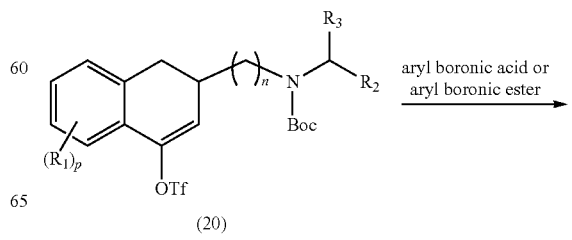

(20)

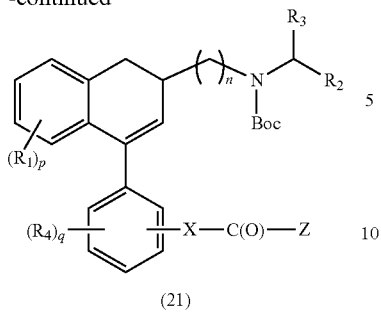
(21)
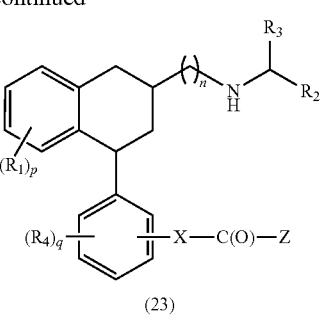
(23)
c) reducing a compound of Formula (21) using palladium on carbon (10%) to give compound of Formula (22);
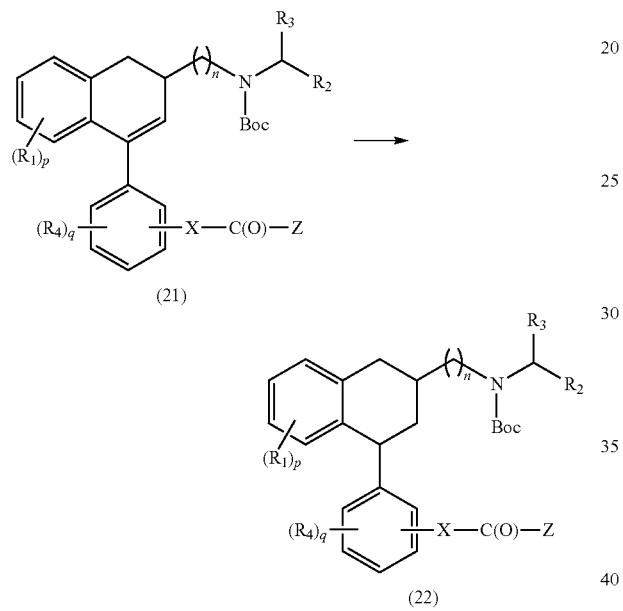
d) deprotecting a Boc functional group using HCl in suitable solvent to get compound of Formula (23)
e) hydrolyzing an ester group of compound of Formula (23) (when Z is —O-alkyl or O-benzyl) using base to afford corresponding acid compound of Formula (Ia)
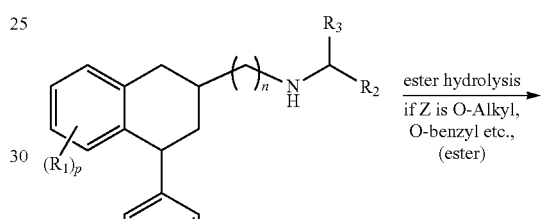
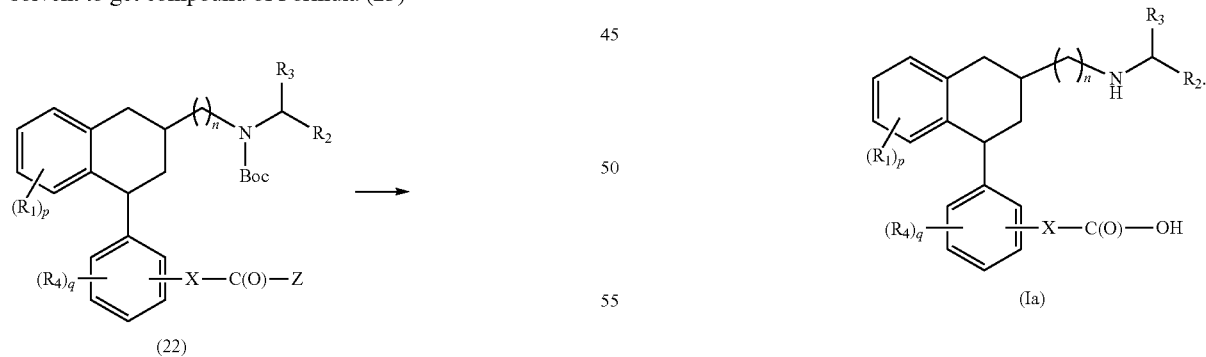
* * * * *